United States Patent [19]
Weiss

[11] Patent Number: 5,981,279
[45] Date of Patent: Nov. 9, 1999

[54] COMPOSITIONS AND METHODS TO REGULATE CALMODULIN GENE EXPRESSION, AND USES THEREOF FOR INFLUENCING CELL GROWTH AND DIFFERENTIATION

[75] Inventor: Benjamin Weiss, Wynnewood, Pa.

[73] Assignee: Allegheny University of the Health Sciences, Philadelphia, Pa.

[21] Appl. No.: 08/748,104

[22] Filed: Nov. 8, 1996

Related U.S. Application Data

[60] Provisional application No. 60/006,423, Nov. 9, 1995.

[51] Int. Cl.$^6$ ...................................................... C12N 5/10
[52] U.S. Cl. ...................... 435/375; 435/91.1; 435/320.1; 435/377; 435/455; 424/450; 514/44; 536/24.5; 536/23.1; 536/23.3; 536/23.31; 536/23.33
[58] Field of Search ................................ 435/91.1, 172.1, 435/172.3, 320.1, 375, 377, 455; 424/450; 514/44; 536/24.5, 23, 23.3, 23.31, 23.33

[56] References Cited

PUBLICATIONS

Hait, W., et al., (1988), Cancer Investigation 6(5): 499–511.
Rasmussen, C., et al., (1989), The EMBO Journal 8: 73–82.
Lu, K.P., et al., (1993), Journal Cell Biology 121: 621–630.
Nojima, H., (1989), J. Mol. Biol. 208: 269–282.
Takeda, T., et al., (1987), Proc. Natl. Acad. Sci. USA 84: 3580–3584.
Liu, T., et al., (1992), Mol. Biol. of the Cell. 3: 1403–1413.
Colomer, J., et al., (1994), J. of Cell Physiol. 159: 542–550.
Christenson, M., et al., (1993), J. of Cell Physiol. 154: 343–349.
Bai, G., et al., (1992), Biochem Biophys. Acta 1130: 189–196.
Hait, W., et al., (1994), Anticancer Res. 14: 1711–1722.
Zhou, L.W., et al. (1985), Journ. Neurochem. 44: 1657–1662.
Cimino, M., et al. (1990), Dev. Brain. Res. 54: 43–49.
Roberts–Lewis, J.M. et al., (1990) SYNAPSE 5: 247–254.
Bai, G., et al., (1991), J. of Cell Physol. 149: 414–421.
Zhang, S.P., et al., (1993), Neuroscience 55: 571–582.
Natsukari, et al., (1995) Neurochem Int. 26: 465–476.
Davidkova, G., et al., (1996), Neuroscience, 75: 1003–1019.
Zhang, S.P. (1994), Soc. Neurosci. 20: 2316.
Solomon et al. (Clinical Res. vol. 41, 4, 800A, 1993).
E. Uhlmann et al. Chem. Rev. 90(4) 543–84, '90.
J. Milligan et al. J. Med. Chem. 36(14) 1923–37, '93.
C. Stein et al. Science 261: 1004–12, '93.
R. Stull et al. Pharm. Res. 12(4) 465–83, '95.
W. James Antivir. Chem. & Chemother. 2(4) 191–214, '91.
S. Orkin et al. NIH Report on Gene Therapy, '95.
T. Friedman et al. Scientific Amer. pp. 96–101, Jun. '97.
G. Davidkova et al. FASEB J. 9(3), p. A382 (Abstract), Mar. 1995.
R. Hinrichsen et al. P.N.A.S. 89: 8601–5, '92.
S. Solomon et al. B.B.R.C. 210(3) 9210–30, May 1995.
A. Thierry et al. Nucl. Acids Res. 20(21) 5691–98, '92.
E. Wagner et al. P.N.A.S. 87: 3410–4, '90.

*Primary Examiner*—Bruce R. Campell
*Assistant Examiner*—Dave Trong Nguyen
*Attorney, Agent, or Firm*—Dann, Dorfman, Herrell and Skillman

[57] ABSTRACT

Constructs encoding calmodulin antisense molecules are disclosed. These constructs may be used to advantage to inhibit proliferation of malignant cells. The invention further comprises monoclonal antibody studded liposomes to facilitate cell-type specific delivery of the antisense calmodulin constructs. To enhance cell-type specific expression of calmodulin antisense sequences, cell-type specific promoters are employed to drive expression of the antisense molecules in targeted tissues.

19 Claims, 21 Drawing Sheets

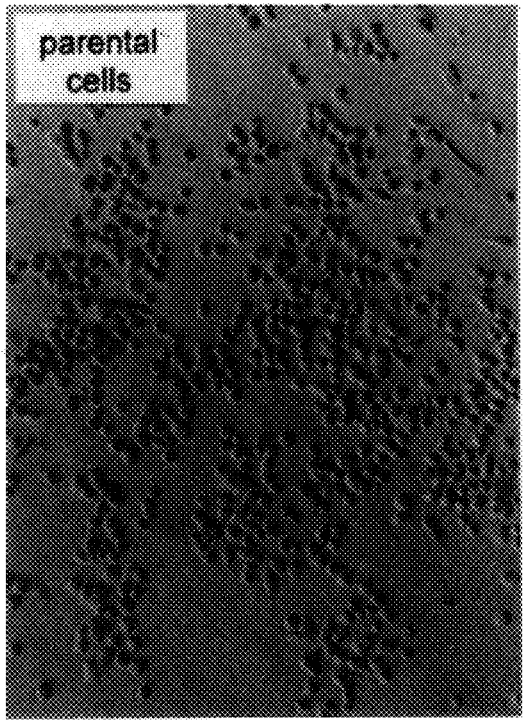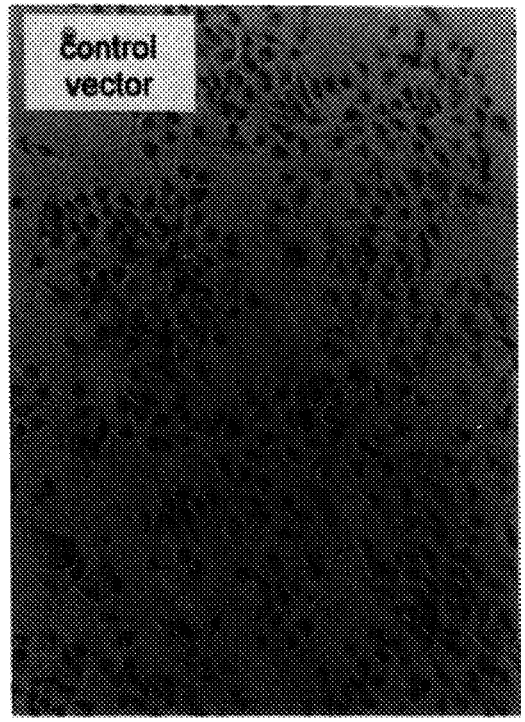
FIG. 2A  FIG. 2B
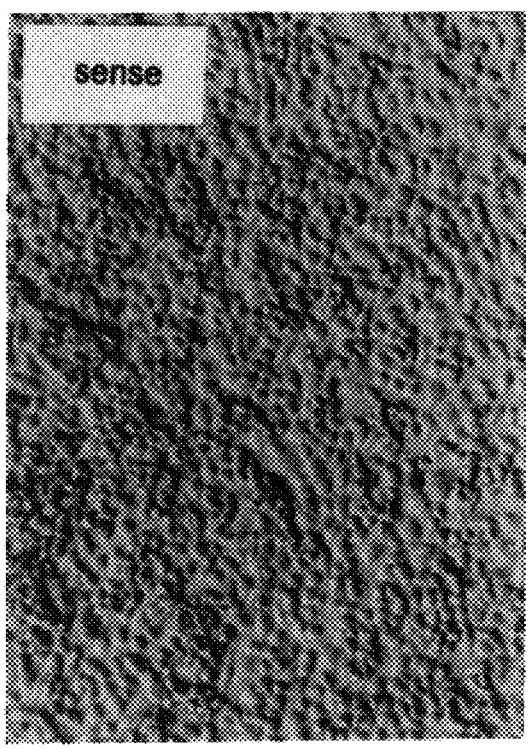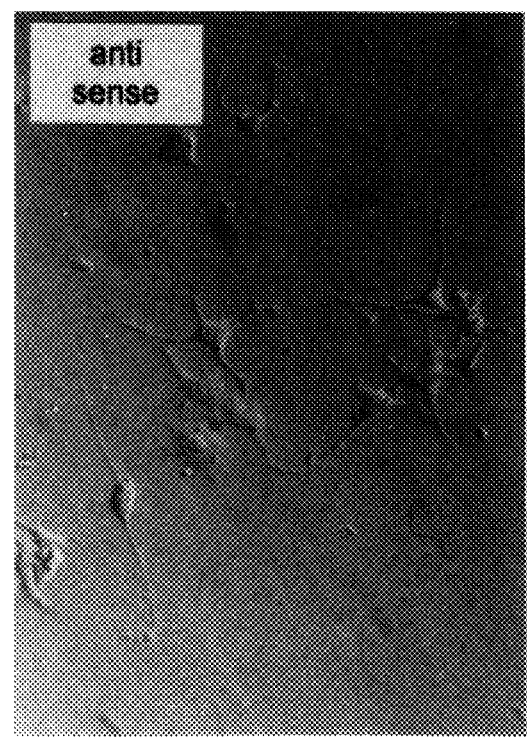
FIG. 2C  FIG. 2D

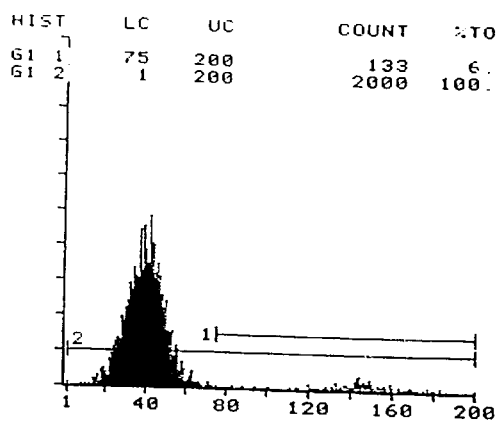
Fig. 19A A431(-MoAb)
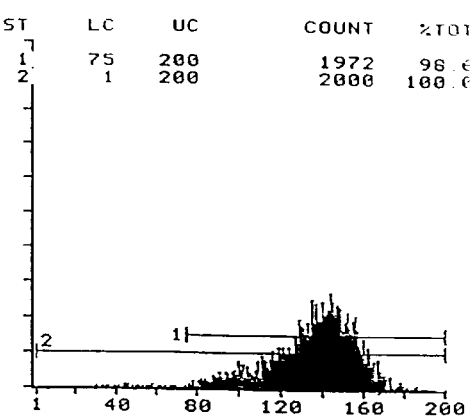
Fig. 19B A431(+MoAb)
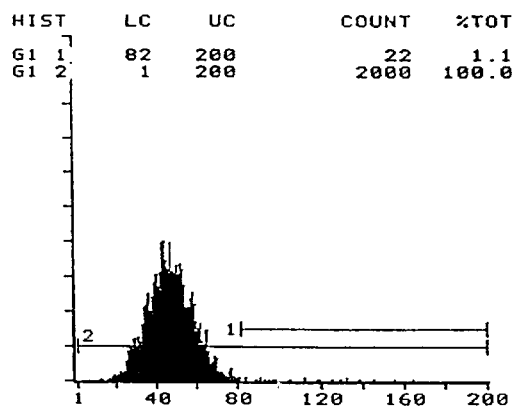
Fig. 19C U-87 MG(-MoAb)
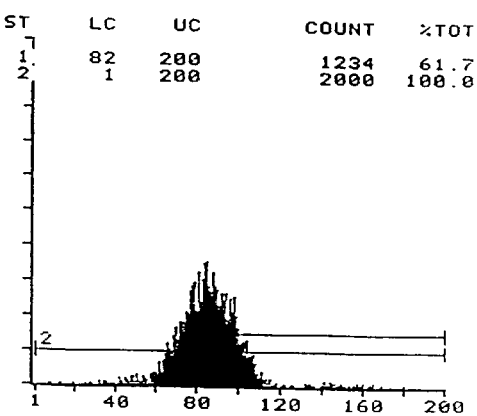
Fig. 19D U-87 MG(+MoAb)
NUMBER OF CELLS
RELATIVE FLUORESCENCE INTENSITY

```
                         SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:1:

CTGATCAGCCATGGTGCGAG                                              20

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iv) ANTI-SENSE: YES
```

(xi) SEQUENCE DESCRIPTION: SEQ ID NO:2:

ATGGTGCGAGCGAAGGAAGG                                              20

(2) INFORMATION FOR SEQ ID NO:3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:3:

TTGGTCAGCCATGCTGCAAG                                              20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:4:

GCCATGCTGCAAGGGCTACC                                              20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:5:

CTGGTCAGCCATGGCGAGGC                                              20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:6:

GCCATGGCGAGGCACGTATC                    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:7:

GCCGAATTCCATGAGGCTTA                    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:8:

GCAAGGACAGGGAGGGTTAG                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:9:

CTCTATCACGGGAGCACCGG                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (xi) SEQUENCE DESCRIPTION: SEQ ID NO:10:

GACAGGCGAGTCCAGTCGTC                    20

COMPOSITIONS AND METHODS TO REGULATE CALMODULIN GENE EXPRESSION, AND USES THEREOF FOR INFLUENCING CELL GROWTH AND DIFFERENTIATION

This application claims priority under 35 U.S.C. §119(e) from U.S. Provisional Application 60/006,423, filed Nov. 9, 1995.

Pursuant to 35 U.S.C. §202 (c), it is hereby acknowledged that the U.S. Government has certain rights in the invention described herein, which was made in part with funds from the National Institutes of Health, Grant Numbers NS30724 and MH 42148.

FIELD OF THE INVENTION

The present invention relates to novel compositions and methodology important for the regulation of cell growth and differentiation. Specifically, the invention provides selected sense and antisense vectors and oligonucleotides (hereinafter "oligos" or "oligomers"), and methods of use thereof, for inhibiting or augmenting intracellular calmodulin levels, thereby either inhibiting proliferation and inducing differentiation in cells or enhancing cell growth.

The sections below describe the invention in greater detail, including the background and significance of the invention and the experimental evidence supporting the invention. Several publications are referenced in this application (in superscript arabic numerals). Full citations for these references are found at the end of the specification. These publications are incorporated herein by reference.

BACKGROUND OF THE INVENTION

Calmodulin is an ubiquitous $Ca^{2+}$-binding regulatory protein that mediates the action of $Ca^{2+}$ in a diverse array of biological events including cell division, microtubular depolymerization and polymerization, cyclic nucleotide metabolism, $Ca^{2+}$ transport, and protein phosphorylation [6,8,31,38,43,72]. The involvement of calmodulin in various nerve cell processes, together with its abundant distribution in brain tissue[75], suggests that calmodulin plays an important role in the growth and differentiation of nerve cells.

The notion that calmodulin is a regulator of cell growth was initially suggested by studies showing that calmodulin antagonists inhibited cell division in vitro by blocking cell-cycle progression at the G1/S boundary and during G2/M[6,15,60]. Consistent with such results are the findings that calmodulin levels are altered during the various phases of the cell cycle[7,42,60] and that calmodulin increases DNA synthesis in a variety of cells [2,24,41,42]. Using eukaryotic expression vectors to produce sense or antisense calmodulin RNA, it was demonstrated that increases or decreases in the intracellular levels of calmodulin result in increases and decreases, respectively, in the rates of proliferation of mouse C127 cells[53,54]. The role of calmodulin in cell growth is also supported by the findings of elevated levels of calmodulin in certain transformed cell types[12,32,66,69].

Although there is evidence for the participation of calmodulin in cell differentiation, its role has not been precisely defined. Treatment of leukemic HL-60 cells with calmodulin antagonists resulted in an increase in cellular differentiation[67]. On the other hand, the levels of calmodulin were found to increase during nerve growth factor (NGF) - induced differentiation of PC12 cells[4].

Structural studies have revealed that the amino acid sequence of calmodulin is remarkably conserved among species[50]. In the rat genome, calmodulin is encoded by three genes expressing five transcripts, each of which encodes an identical protein, the sequence variations in the coding regions being within the limits of codon degeneracy [47,48,50,63]. These calmodulin mRNAs are heterogeneously distributed both in the newborns[11,70] and adult rat brain[18,56] and have been shown to change during ontogeny in a pattern which is paralleled by similar changes in the biological activity of calmodulin[11], indicating that calmodulin is involved in neuronal development.

Using the PC12 clonal cell line[21] as an in vitro model for investigating neuronal development, it was demonstrated that PC12 cells express, in varying levels, all five calmodulin gene transcripts[4]. Differentiation of PC12 cells induced by NGF or dibutyryl cyclic AMP was accompanied by characteristic and distinct changes in the levels of the various calmodulin mRNAs, demonstrating that the calmodulin genes can be differentially regulated[34]. Other studies showed that the multiple calmodulin transcripts have distinct subcellular distributions, some being found both in the cell bodies and neurites and others found only in the cell bodies[74]. Since the cellular location of calmodulin will determine its functional activity, these results suggested that the regulation of the levels of particular calmodulin mRNAs in different subcellular compartments may, in turn, be one means for controlling the different functional activities for calmodulin in nerve cells. However, it has not yet been determined if calmodulin gene expression plays a causal role in differentiation.

SUMMARY OF THE INVENTION

The present invention provides methodology to promote cell growth or induce differentiation in targeted cell types by augmenting or inhibiting the expression of calmodulin. As noted previously, many cancer cells express elevated levels of calmodulin. Cancer cells or transformed cells often have a dedifferentiated phenotype and therefore grow in an unregulated fashion. Therapeutic agents that cause these cells to differentiate via the modulation of calmodulin levels by the administration of antisense calmodulin constructs would be a beneficial addition to the arsenal of drugs used for chemotherapy.

Calmodulin stimulates at least five different protein kinases and a single protein phosphatase, calcineurin, highly active in brain, and can thereby modulate the activities of the many substrates of these proteins. Thus few, if any, neuronal functions escape the control of Ca+ and calmodulin. Therefore, upregulating the levels of calmodulin in neurons may be beneficial in neurodegenerative disorders and in the aging process. For example, one of the microtubule associated proteins, tau protein, becomes abnormally hyperphosphorylated with aging. This protein is a major constituent of the neurofibrillary tangles in Alzheimers disease, the most common form of senile dementia. It has been shown that calcineurin is involved in the dephosphorylation of abnormal phosphorylation sites in tau. Increasing levels of calmodulin and thereby the activity of calcineurin may decrease the formation of these neurofibrillary tangles in Alzheimers disease.

According to one aspect of the present invention, a method is provided for inducing differentiation in a de-differentiated cell type. The method comprises providing an antisense oligonucleotide capable of binding to an expression controlling sequence of a nucleic acid encoding calmodulin. The antisense oligonucleotide is administered to the cell under conditions whereby the oligonucleotide enters the cell and binds specifically to the expression controlling sequence of the nucleic acid encoding calmodulin, in an amount sufficient to inhibit the production of calmodulin and induce differentiation of the targeted cell type.

According to another aspect of the present invention, a composition is provided that is useful for inhibiting expression of a pre-determined calmodulin gene in a living organism. The compound comprises an oligonucleotide analog capable of entering a cell containing the targeted calmodulin gene and binding specifically to an expression-controlling sequence of the gene, or mRNA encoded by the gene, in an amount sufficient to inhibit production of calmodulin encoded by the gene. The composition is useful for inducing differentiation in de-differentiated cells, such as tumor cells.

According to another aspect of the present invention, a method is provided for treating a pathological condition related to abnormally high expression of calmodulin in neuronal cells. The compound is comprised of calmodulin antisense oligomers in a suitable carrier, that will target the desired neuronal cell types and thereby inhibit deregulated cell growth.

According to another aspect of the invention, compositions and methods are provided to effect long-term augmentation or inhibition of calmodulin production in a selected cell type, thereby enhancing growth or inducing differentiation, respectively. These aspects involve transforming the cell type with an expression vector containing nucleic acids that either encode calmodulin or encode antisense RNA molecules capable of inhibiting endogenous calmodulin gene expression. To further enhance the specificity of the calmodulin constructs of the invention, the dominant calmodulin transcript expressed in targeted cell types will be identified. Corresponding antisense calmodulin constructs will then be synthesized and delivered to cells to inhibit cellular proliferation.

The antisense oligonucleotides or vectors producing calmodulin antisense RNA will be targeted to the specific calmodulin mRNAs transcribed from the different calmodulin genes. Since the different calmodulin mRNAs are present in varying abundance in different cell types and are found in different proportions in different parts of the cell, they may have different functions in the cell. By specifically inhibiting the different calmodulin mRNAs with antisense oligomers targeted to the different calmodulin mRNAs, the functions of specific cell types may be altered in a selective manner. Tissue specific targeting of the calmodulin constructs of the invention will be achieved using antibody-studded liposomes. Tissue specific expression of the constructs will be achieved by operably linking the calmodulin sequences of the invention to tissue-specific promoters.

In preferred embodiments of the present invention, the antisense oligomer is an oligonucleotide analog having improved stability and membrane permeability as compared to the unmodified oligonucleotide. The antisense oligonucleotide analog is capable of crossing a biological membrane in order to enter cells and thereafter bind specifically with the selected nucleic acid sequence. The selected nucleic acid sequence preferably comprises a translation start site of mRNA encoding calmodulin. The biologically compatible medium is preferably formulated to enhance the lipophilicity and membrane-permeability of the antisense oligonucleotide.

BRIEF DESCRIPTION OF THE DRAWINGS

FIGS. 2A–2D: Effect of transfection with calmodulin sense and calmodulin antisense expression vectors on the morphology and growth of Geneticin-resistant colonies. PC12 cells were stably transfected with the different expression constructs as described in the examples. The photomicrographs show representative parental cells (A), Geneticin-resistant colonies from PC12 cells transfected with control vector (B), calmodulin sense (C), or calmodulin antisense (D) expression vectors. The cells were viewed with a light microscope equipped with Hoffman modulation optics. Scale bar, 100 μm.

FIG. 3A: Northern analysis showing the specificity of the digoxigenin-labeled calmodulin gene I oligonucleotide probe. Total cellular RNA (5 μg) from untransfected PC12 cells was processed for Northern analysis according to the procedure described in the examples. The RNA was incubated with the digoxigenin-labeled calmodulin gene I oligonucleotide probe (25 pmol/ml) for 16 hours at 42° C. The probe hybridized to two transcripts of molecular sizes 1.7 and 4.1 kb, determined by comparison with a standard RNA ladder (Gibco). FIG. 3B: Changes in the levels of calmodulin gene I mRNA as determined by slot-blot analysis. PC12 cells were transiently transfected with a full-length calmodulin gene I (CaM Sense) or control (Control Vector) expression vectors and subjected to slot-blot analysis. The blotted RNA samples (10 and 2.5 μg) were hybridized to a digoxigenin-labeled calmodulin gene I oligonucleotide probe (CaM Gene I) for 16 hours at 42° C. (top panel). The amount of mRNA was compared to the hybridization of a digoxigenin-labeled cyclophilin probe (Cyclophilin) for 16 hours, 55° C. (bottom panel), used as a control. The chemiluminescent signals were detected by exposure of the blots to an X-ray film for 30 minutes, and the autoradiographic density was quantified using the DUMAS. Shown are the results from a representative of three separate transfection experiments (n=3).

Untransfected parental PC12 cells and cells stably transfected with control vector, calmodulin sense or antisense vectors were plated onto collagen-coated 24-well tissue culture dishes at a density of $2\times10^4$ cells/cm$^2$. At days 0, 1, 2, 4 and 8, neurite outgrowth was measured with a differentiation score based on the length of the neurites and the number of neurites per cell[4]. This scoring system varies from 0 (no neurite outgrowth) to a maximum score of 3. Each value was obtained by measuring the differentiation score of at least 100 cells. The data presented are from triplicate experiments with 2 individual clones from each construct. *p<0.01 compared with the values obtained for parental PC12 cells and stable control vector or sense vector-containing cells at the corresponding time points.

Figure 6:
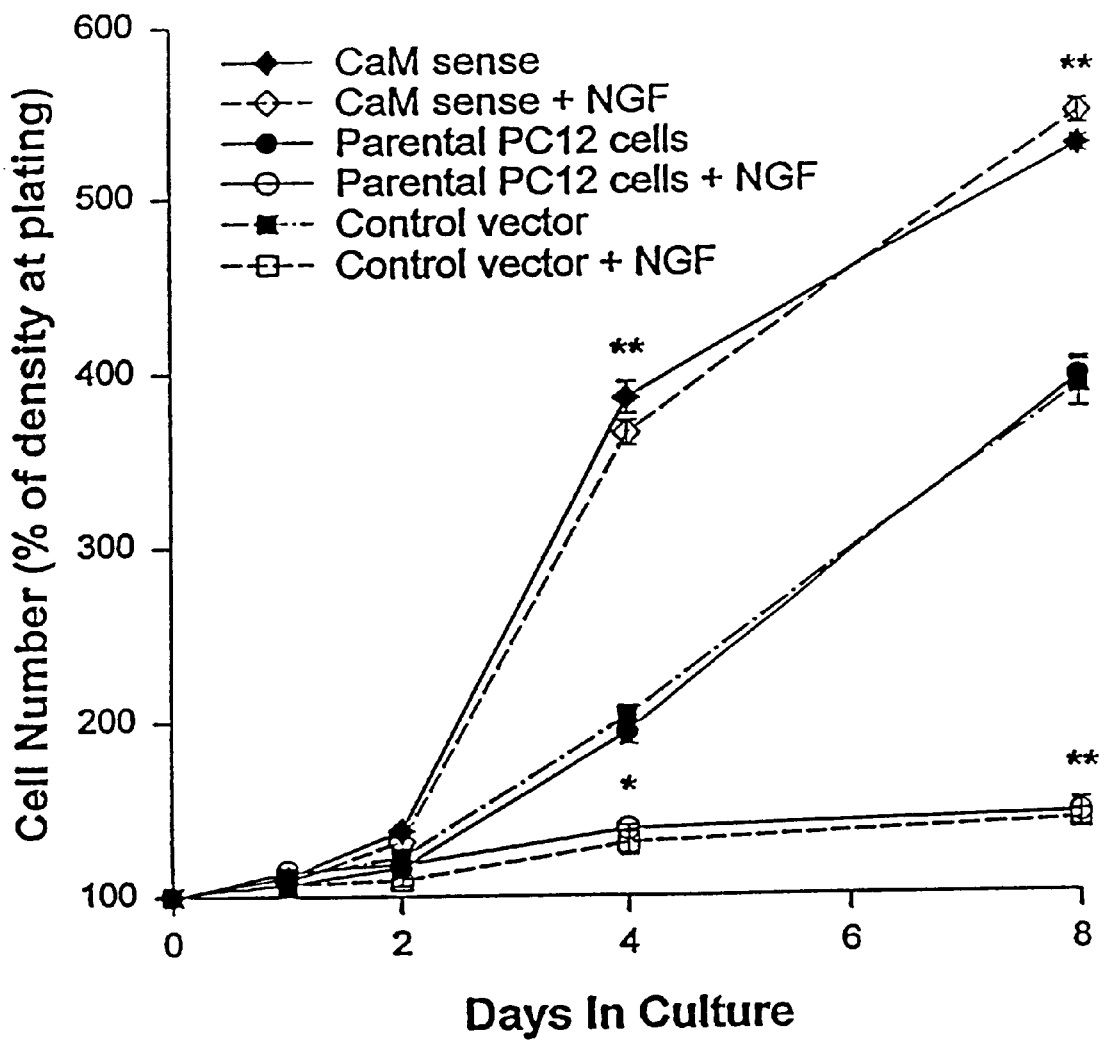

FIG. 6: Effect of overexpression of calmodulin on the proliferation of PC12 cells in response to treatment with NGF. Cell numbers were determined by direct counting of parental PC12 cells and cells stably transfected with control vector or the calmodulin gene I sense constructs cultured in the presence or absence of NGF (50 nM) for 0, 1, 2, 4 and 8 days as described in the examples. The results presented are the means±SEM from values obtained from 2 experiments performed in triplicate using 4 clones, 2 of which contained the calmodulin sense construct and 2 with the control vector. **p<0.01, compared with values from the parental PC12 cells or the cells transfected with the control vector at the corresponding time points.

Figure 7:
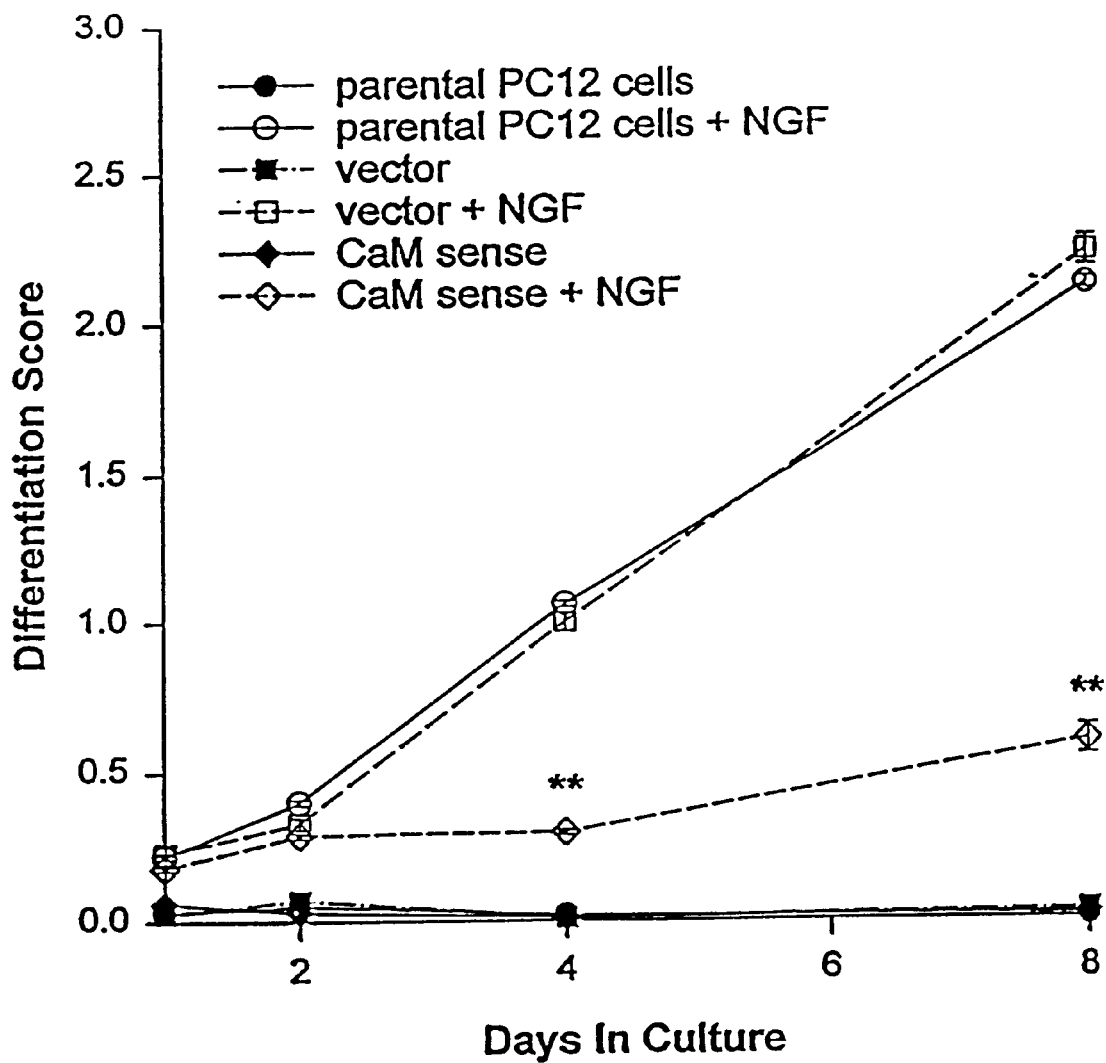

FIG. 7: Quantitative analysis of the effect of stably transfecting PC12 cells with a calmodulin sense vector on the outgrowth of neurites in response to treatment with NGF. Neurite outgrowth was measured from parental PC12 cells and cells stably transfected with control or with calmodulin sense vectors, cultured in the presence or absence of NGF (50 nM) for 0, 1, 2, 4 and 8 days, using a differentiation score based on the length of the neurites and the number of neurites per cell. This scoring system varies from 0 (no neurite outgrowth) to a maximum score of 3. It should be noted that in plates which contained cells that had a rapid rate of proliferation some of the cells were too close together to accurately determine their extent of neurite outgrowth. In such cases, only those fields in which the cells were sufficiently isolated from each other were used to assess their differentiation score. Each value is the mean±SEM of the differentiation score of at least 100 cells, combined from two experiments using 4 clones, 2 clones from a given construct. ** p<0.01 compared with the values from the parental cells incubated with NGF or with cells transfected with the control vector and incubated with NGF at the corresponding time points.

Figure 8:
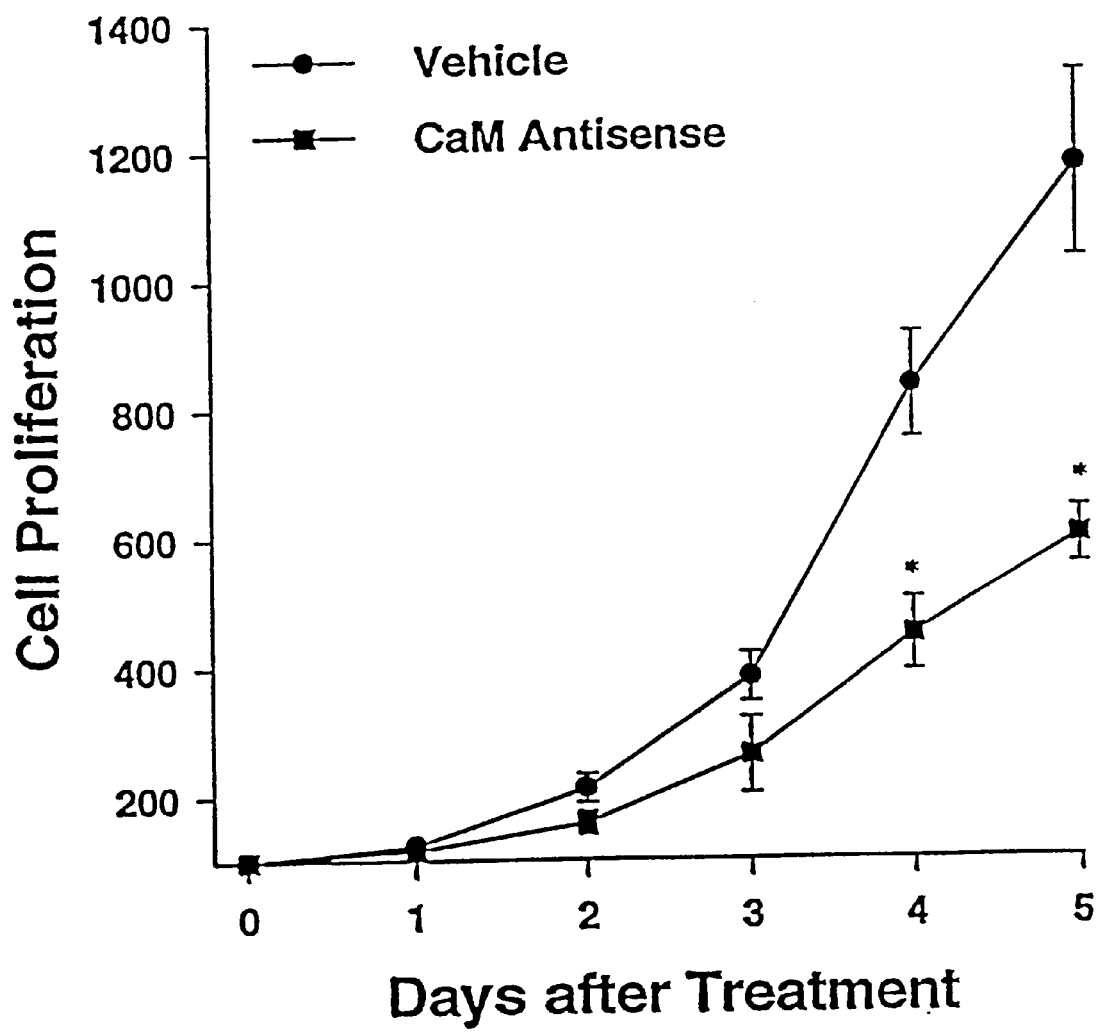

FIG. 8: Effect of calmodulin antisense oligos on the proliferation of PC12 Cells. PC12 cells were incubated with vehicle or with 4 $\mu$M each of the three calmodulin antisense 20-mers (12 $\mu$M total), and the number of cells was counted every day over a 5-day period. Each point represents the mean value from 3 samples. The data were analyzed by a two-way ANOVA followed by a Newman-Keuls t test. Calmodulin antisense oligos significantly inhibited the proliferation of PC12 cells after 4 and 5 days of treatment. * p<0.01 compared with vehicle.

Figure 9:
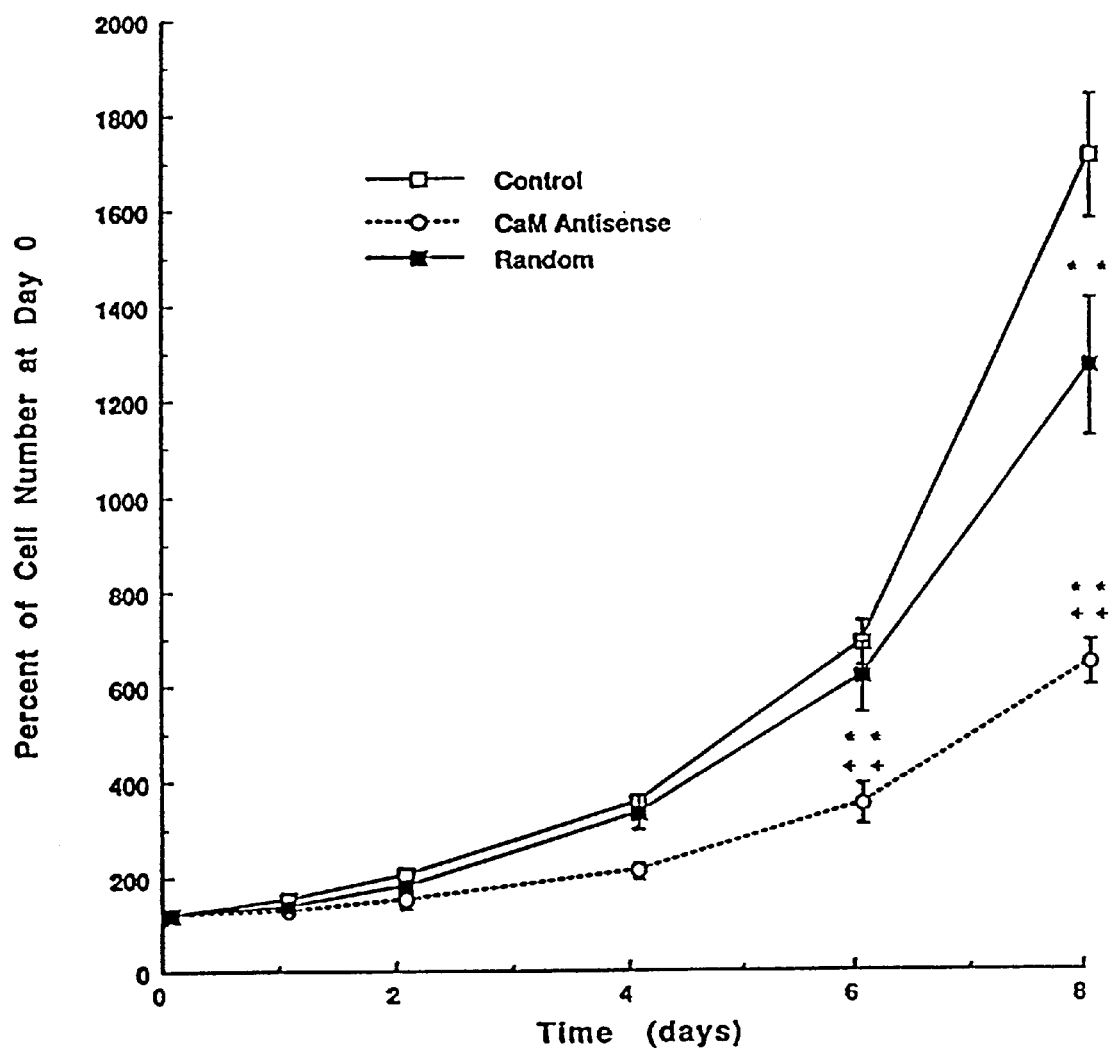

FIG. 9: Effect of calmodulin antisense oligodeoxynucleotides on the proliferation of PC12 Cells. PC12 cells were plated onto 24-well collagen coated plates with medium (DMEM+10% FBS+5% HS) one day before the calmodulin antisense and random oligodeoxynucleotides were added. Each well contained approximately 15,000 cells. After 24 hours, the medium was removed and defined medium (DMEM+N-2 supplement) containing 1.0 $\mu$M each of the three calmodulin antisense or random oligodeoxynucleotides was added to each well. Four days later, the cells were subcultured in a 96-well collagen-coated plate in medium (DMEM+10% FBS+5% HS), each well contained about 3,000 cells. One day after subculturing the cells, the medium was removed and defined medium containing the antisense or random oligos (at the same concentration as above) was added to each well. The day on which the medium was changed after subculturing the cells was considered to be day 0. The cell number in two selected fields from each well was determined on days 0,1,2,4,6 and 8.

Figure 10:
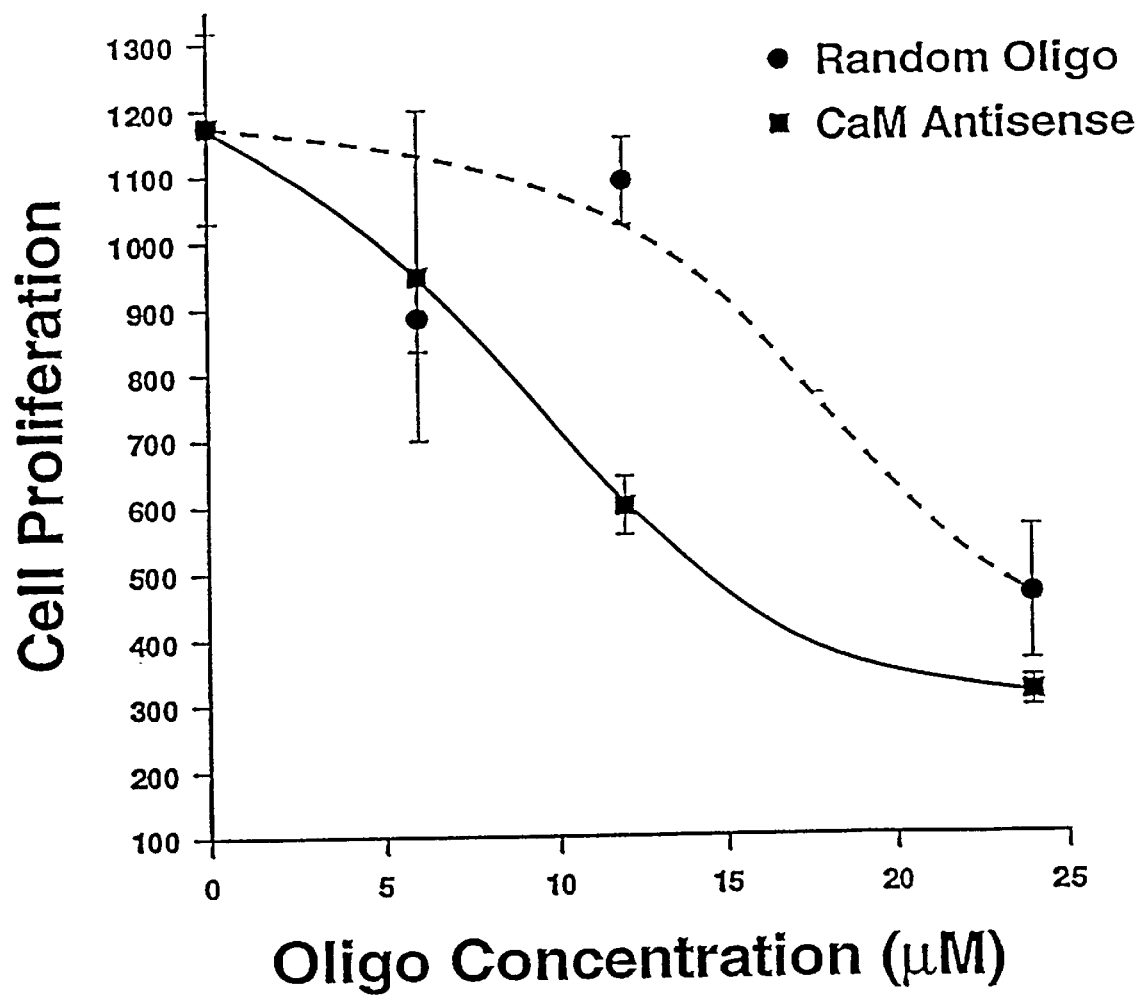

FIG. 10: Effect of varying concentrations of calmodulin antisense oligonucleotides on the proliferation of PC12 Cells. PC12 cells were incubated for 5 days with the 3 calmodulin antisense 20-mers at the indicated total concentration. Each point represents the mean value from 3 samples. Calmodulin antisense oligos inhibited the proliferation of PC12 cells in a dose-dependent manner. Curves are optimum sigmoid fits for typical dose-response functions.

FIGS. 11A, 11B, and 11C: Effect of individual calmodulin gene antisense oligonucleotides on the proliferation of PC12 Cells. PC12 cells were plated onto 96-well collagen-coated plates with medium (DMEM+10% FBS+5% HS) one day before the calmodulin antisense and random oligonucleotides were added, each well containing approximately 3,000 cells. After 24 hours, the medium was removed and defined medium (DMEM+N-2 supplement) containing varying concentrations of calmodulin antisense or random oligodeoxynucleotides was added. The day on which the calmodulin antisense and random oligodeoxynucleotide-containing medium was added was considered to be day zero. Cell numbers in two selected fields from each well were determined on day 0 and day 4. FIG. 11A, antisense to calmodulin gene I; FIG. 11B, antisense to calmodulin gene II; FIG. 11C, antisense to calmodulin gene III.

FIG. 12 (panels A, B, C, and D): Distribution of calmodulin in hippocampal cells. Hippocampi were dissected from embryonic day (E)18 Sprague-Dawley rat fetuses. The hippocampal neurons were cultured on poly-L-lysine pre-coated glass coverslips for 3 to 5 days in dishes containing cortical glia. (These studies were performed in collaboration with Dr. Itzhak Fisher at the Medical College of Pennsylvania.) For the calmodulin distribution studies (A), the cells were fixed in 4% paraformaldehyde and permeabilized with 0.1% Triton X-100 in PBS. The cells were sequentially incubated with a mouse anti-calmodulin MoAb (Sigma) and peroxidase-conjugated goat anti-mouse IgG (Sigma). The peroxidase was detected using an AEC staining kit. For the calmodulin MRNA distribution studies, the cells were fixed in 4% paraformaldehyde, followed by in situ hybridization with $^{35}$S-labelled oligonucleotide probes specific for the mRNAs from calmodulin gene I (B), calmodulin gene II (C) or calmodulin gene III (D) and emulsion-based autoradiography. Calmodulin immunoreactivity was observed in the hippocampal cell bodies (A 1, arrowhead), dendrites and growth cones (A 1, arrow). The calmodulin mRNAs were found in the cell bodies but not in the dendrites (arrowheads, FIG. B, gene 1; C, gene II; D, gene III).

Figure 13:
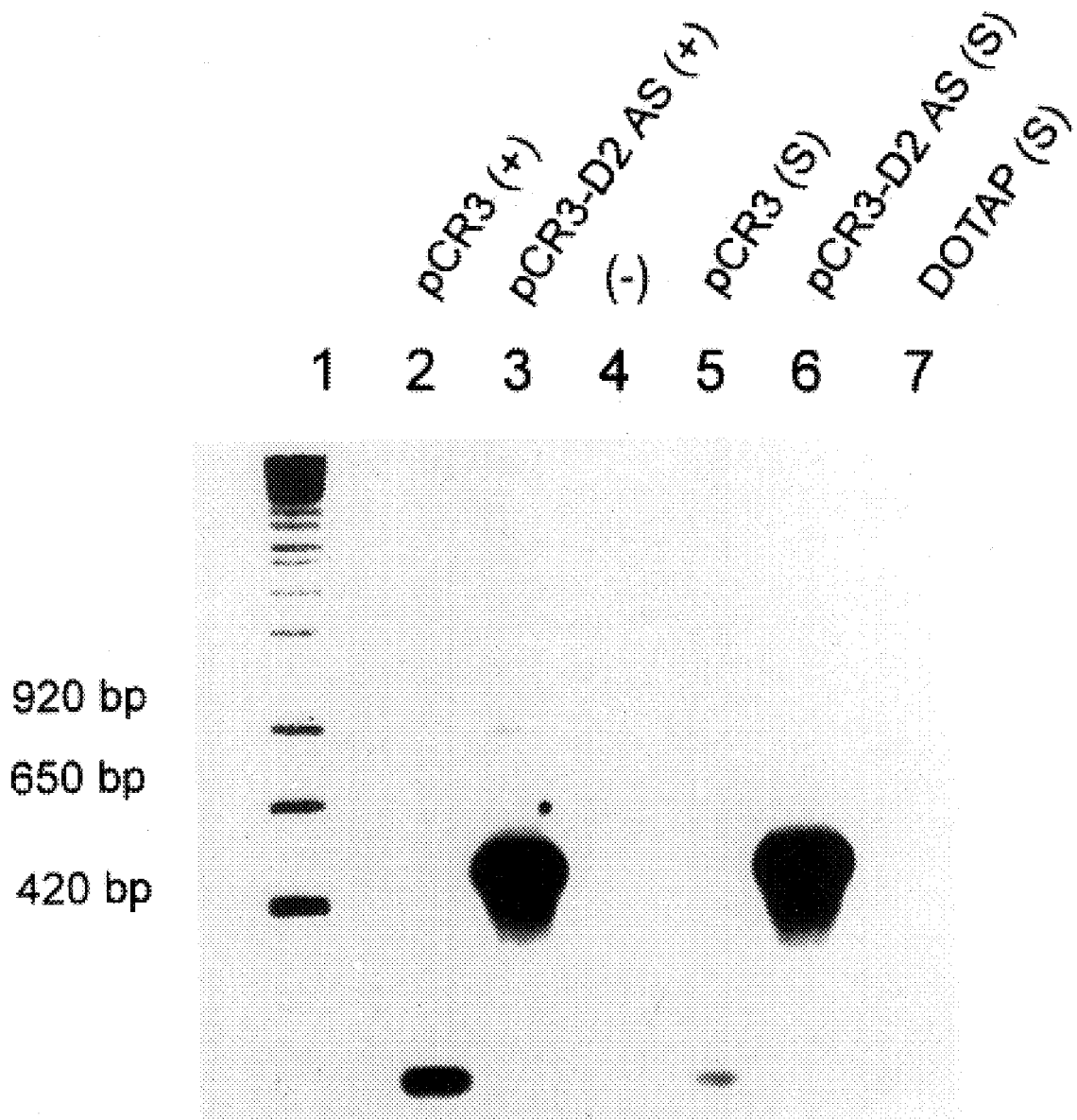

FIG. 13: Uptake of a $D_2$ antisense RNA expression vector in mouse brain. Mice were given single intrastriatal injections of either a $D_2$ antisense vector complexed with DOTAP (25 $\mu$g DNA and 10 $\mu$g DOTAP), an empty pCR3 vector complexed with DOTAP (25 $\mu$g DNA and 10 $\mu$g DOTAP) or DOTAP alone (10 $\mu$g), all in artificial cerebrospinal fluid. Six days later, genomic DNA was extracted from the injected striata by digestion with proteinase K/SDS according to standard methodology[135]. The DNA samples were subjected to PCR with T7 and SP6 primers, specific for sites flanking the vector polylinker, using [$^{32}$P]-dCTP for radioactive detection. $D_2$ antisense vector or empty vector purified from *E. coli* served as positive controls. The PCR products were electrophoresed on a 2% agarose gel and exposed to an x-ray film. The autoradiogram shows the resultant PCR products: Lane 1, $^{35}$S-labelled DNA molecular size ladder, 22–0.4 kb (the lengths of the smallest fragments are indicated on the left); Lane 2, empty vector control (pCR3(+)); Lane 3, $D_2$ dopamine antisense RNA vector control; Lane 4, negative control without DNA(–); Lane 5, striatal (S) DNA from mice injected with empty vector (pCR3(S)); Lane 6, striatal (S) DNA from mice injected with the $D_2$ dopamine antisense vector (pCR3-$D_2$ AS(S) ); Lane 7, striatal DNA from mice injected with DOTAP alone. The PCR amplification yielded bands of expected size, one corresponding to the size (approximately 180 bp) of the empty vector polylinker (lanes 2 and 5) and one corresponding to the size (approximately 485 bp) of the $D_2$ dopamine antisense insert (lanes 3 and 6).

Figure 14:
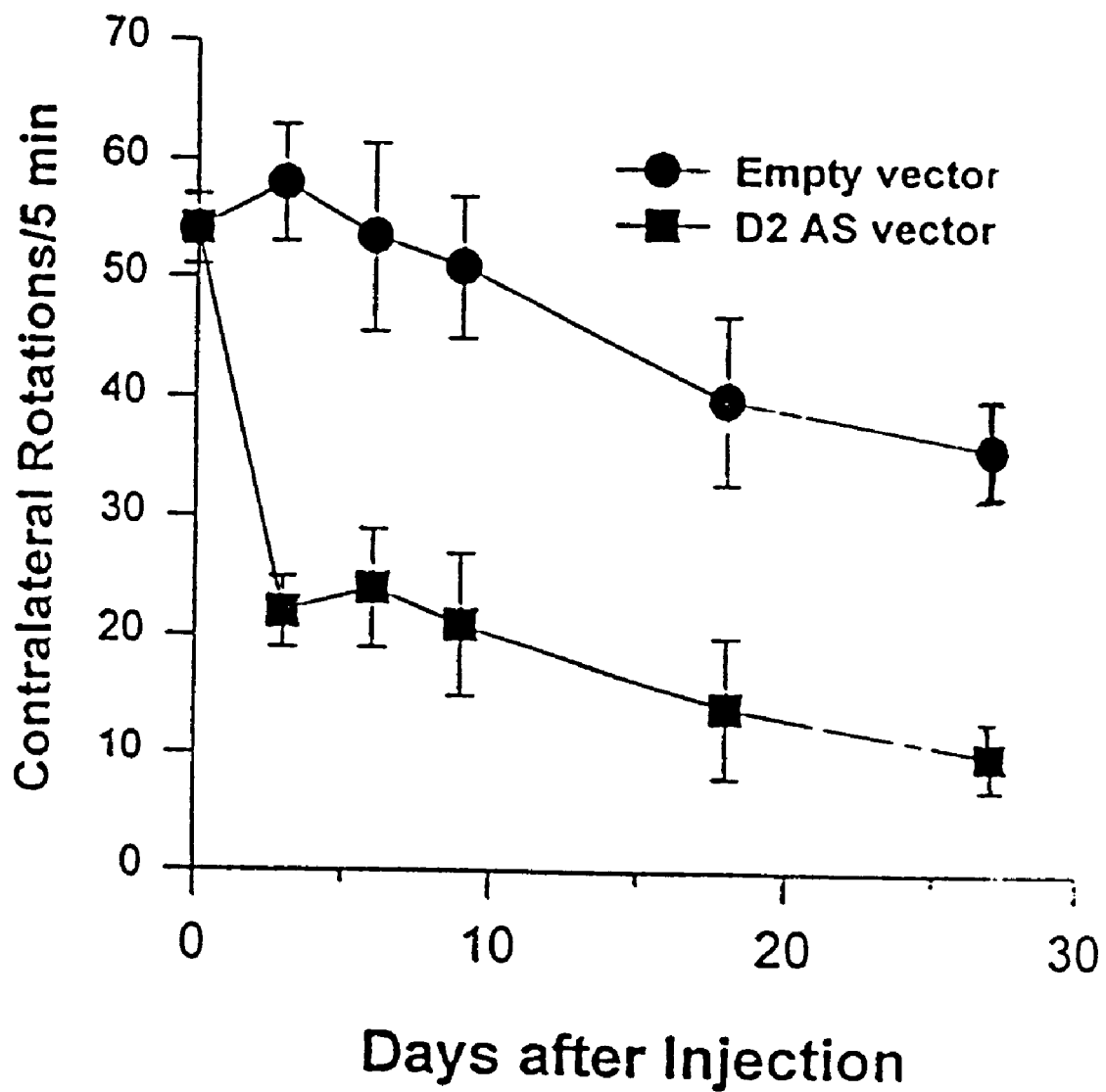

FIG. 14: Effect of a $D_2$ antisense RNA expression vector injected in vivo into mouse brain on $D_2$ dopamine agonist-mediated behavior. Mice with unilateral intrastriatal lesions induced by 6-hydroxydopamine were given a single intrastriatal injection of the $D_2$ antisense RNA expression vector ($D_2$ AS vector) or an empty control vector, as described in the legend to FIG. 13. Contralateral rotational behavior induced by the $D_2$ dopamine receptor agonist quinpirole (5 μmol/kg, s.c.) was measured at various times after the injection of the $D_2$ antisense or control empty vector. Each point represents the mean value from 6 to 8 mice. Statistical analyses were performed by a two-way ANOVA. The results show that quinpirole produces a marked contralateral rotational behavior in animals injected with the empty vector. However, this rotational behavior induced by quinpirole was significantly inhibited after a single intrastriatal injection of the $D_2$ antisense plasmid vector. This inhibitory effect lasted for about one month.

Figure 15:
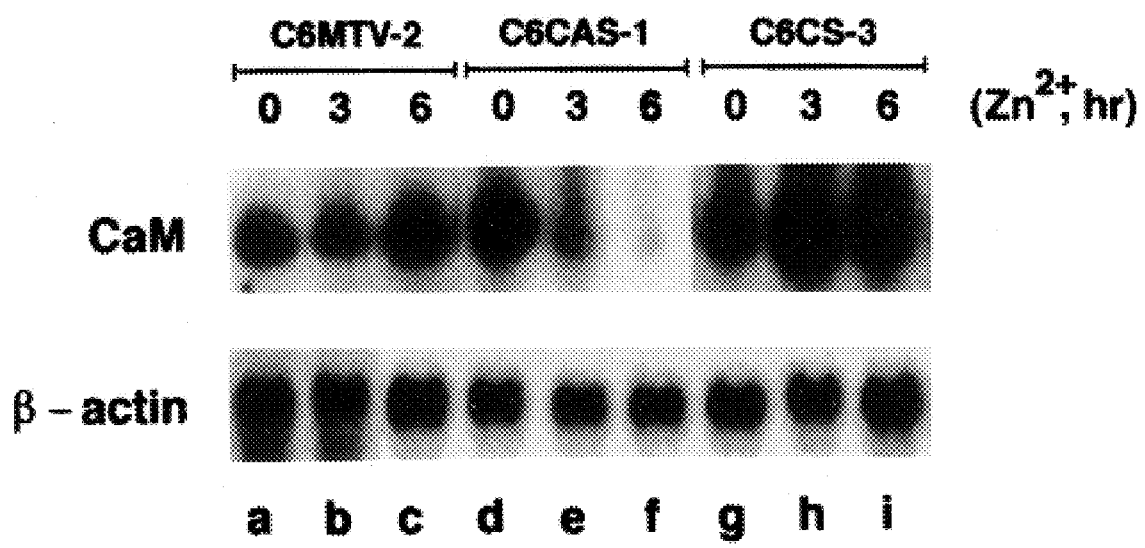

FIG. 15: Changes in the levels of calmodulin mRNA in transfected C6 glioma cells. Representative clones of C6 glioma cells, stably transfected with an empty cloning vector (C6MTV-2), calmodulin antisense (C6AS-I) or sense (C6CS-3) expression vectors, were treated with 60 μM $Zn^{2+}$. At the indicated times (0, 3 or 6 hours), total RNA was isolated, and Northern blot analyses were performed using a $^{32}$P-labeled DNA probe specific for the transcripts from calmodulin gene I. The differences in the RNA loading of the various lanes were normalized using a $^{32}$P-labeled β-actin DNA probe.

Figure 16A:
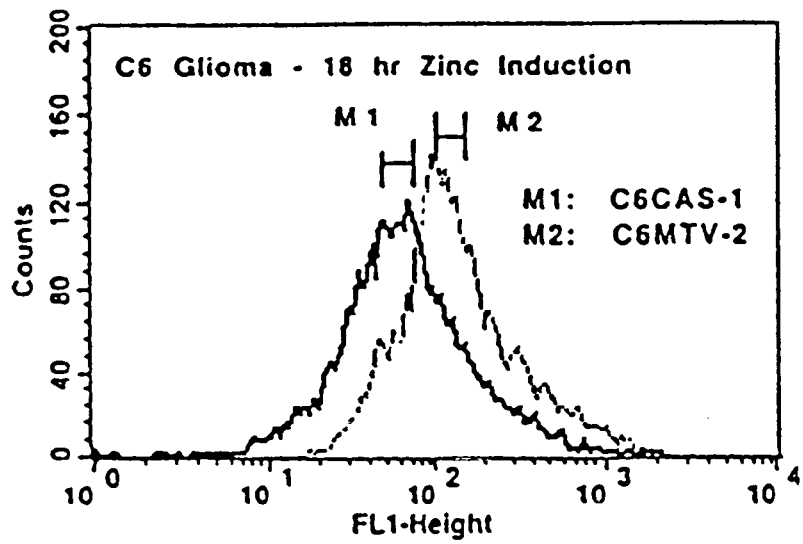
Figure 16B:
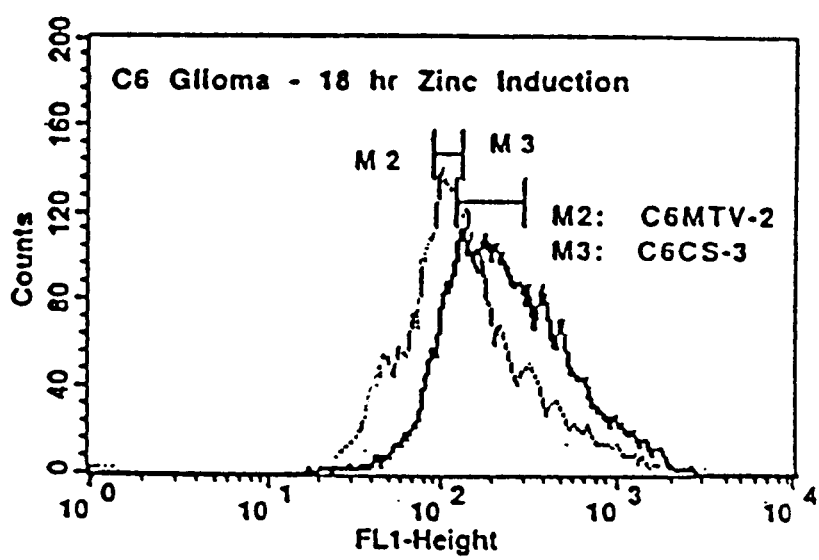

FIG. 16: Changes in the levels of calmodulin in glioma cells due to underexpression or overexpression of calmodulin. The levels of calmodulin in the stably transfected C6 glioma cell clones C6MTV-2 (empty vector), C6CAS-I (calmodulin antisense vector) and C6CS-3 (calmodulin sense vector) were measured by indirect immunofluorescence. Cells were grown in the absence or presence of $Zn^{2+}$ and were sequentially incubated with a mouse anti-calmodulin MoAb (Upstate Biotechnology) and FITC-conjugated rabbit anti-mouse IgG. The fluorescence intensity (FL-I-height) of the individual cells was measured using a Becton Dickinson Scan instrument. The results show that the levels of calmodulin were lower in the calmodulin antisense transfectants, demonstrated by a substantial shift in the peak to lower fluorescent values (compare M1 with M2), and higher in the calmodulin sense transfectants when compared with control cells (compare M2 with M3).

Figure 17:
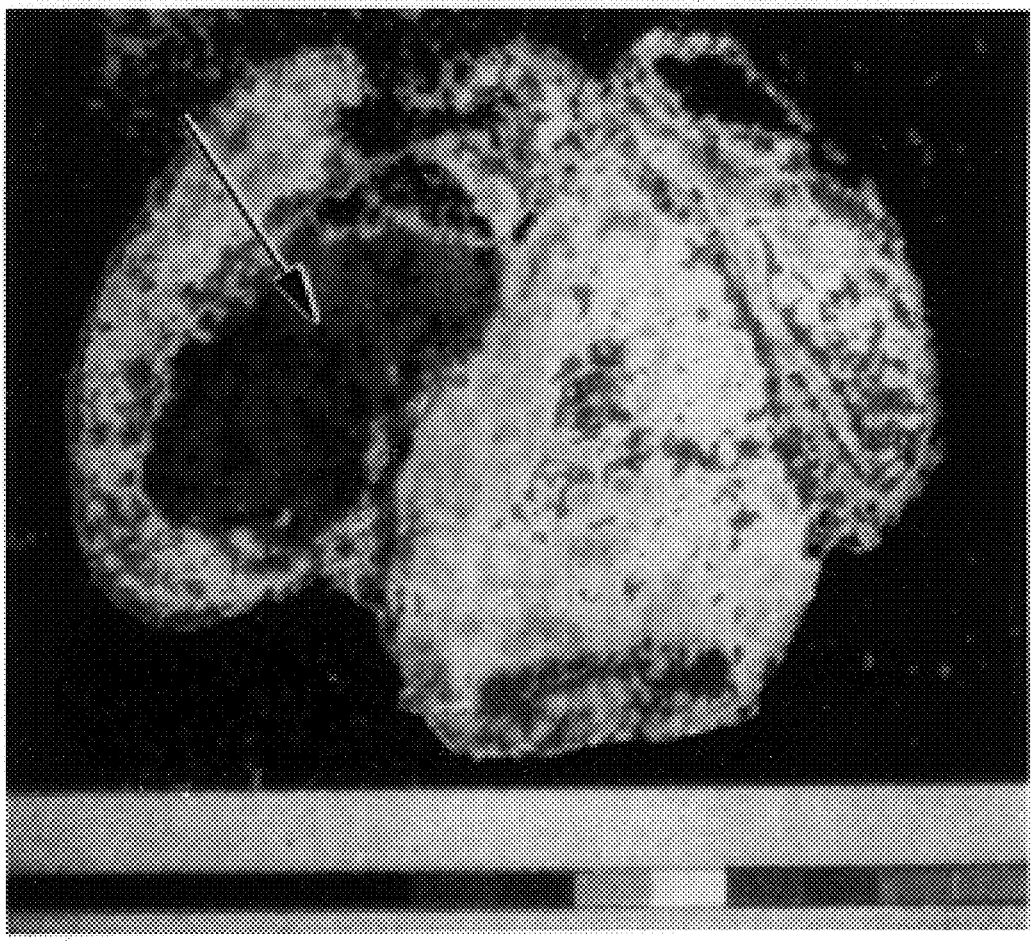

FIG. 17: Increased levels of calmodulin mRNA in rat intracranial glioma tumors. Rat C6 glioma cells (10 μl containing 50,000 cells suspended in 1% agar in PBS) were injected stereotactically into the corpus striatum of male CDF rats. Thirty days later, the brains were removed, sectioned, and processed for in situ hybridization histochemistry using an $^{35}$S-labelled oligonucleotide probe complementary to the transcripts from calmodulin gene I, as described previously[11]. The photograph represents a pseudocolor image of the autoradiogram, obtained using a Drexel University Image Analysis System. There was a significantly higher signal for the transcripts from calmodulin in the tumor tissue (arrow) than in the surrounding brain tissue or in the uninjected striatum.

Figure 18:
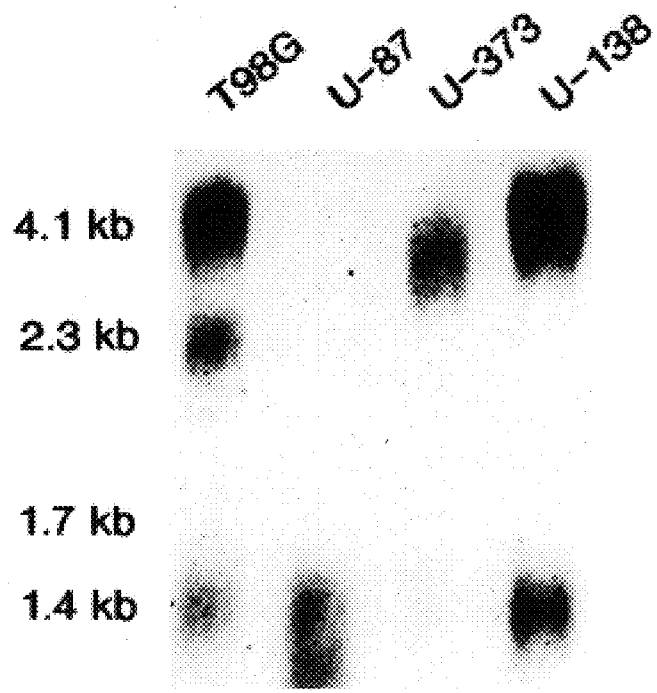

FIG. 18: Relative abundance of the individual calmodulin transcripts in human glioma cell lines. Total cellular RNA was isolated from cultered human glioblastoma cell lines T98G, U-87 MG, U-373 MG and U-138 MG using the Trireagent (Molecular Research Center), and the expression of the individual calmodulin was assayed by Northern blotting. Assignment of each RNA band to one of the calmodulin transcripts (indicated on the left) was made by comparison with an RNA ladder run on the same gel.

FIGS. 19A, 19B, 19C, and 19D: Binding of anti-EGF receptor monoclonal antibody 425 to U-87 MG human glioblastoma cells. The cell line, U-87 MG was chosen for antibody binding analysis based on earlier observations that $^{131}$I-labeled F(ab')$_2$ fragments of MoAb 425 preferentially localize to U-87 MG cell xenografts in nude mice when compared to normal tissues[122]. The binding of MoAb 425 to human squamous cell carcinoma A431 cells, (which were used as the antigen source to produce the monoclonal antibody) was measured as a positive control. MoAb 425 recognizes a cell surface protein epitope which is easily denatured and/or internalized. Therefore, all steps of the indirect immunoflourescent staining were performed at 4° C. without fixation of cells. The cells (A431 or U-87 MG) were trypsinized, harvested, washed, and incubated sequentially with purified primary MoAb 425 (10 μg/ml in assay buffer, consisting of PBS containing 1% BSA) and secondary FITC-labeled goat anti-mouse IgG (Jackson ImmunoResearch; 1:200 dilution in assay buffer). Flow cytometric analysis was performed using an Ortho ICP-22A flow cytometer, and fluorescent histograms were recorded on an Ortho Model 2103 distribution analyzer. Raw data histograms with green fluorescence intensity (in channel units) on the abscissa and percentage of cells with that fluorescent intensity on the ordinate are shown. The histograms illustrate that in the absence of MoAb, most of the cells had a low level of fluorescence (FIGS. 19 A and C) whereas in the presence of MoAb, the cells had high fluorescence intensity, (FIGS. 19 B and D). FIG. 19A: Negative control A431 cells without MoAb 425; FIG. 19B: Binding of MoAb 425 to A431 cells; FIG. 19C: Negative control U-87 MG cells incubated in the absence of MoAb 425; FIG. 19D: Binding of MoAb 425 to U-87 MG cells.

Figure 20:
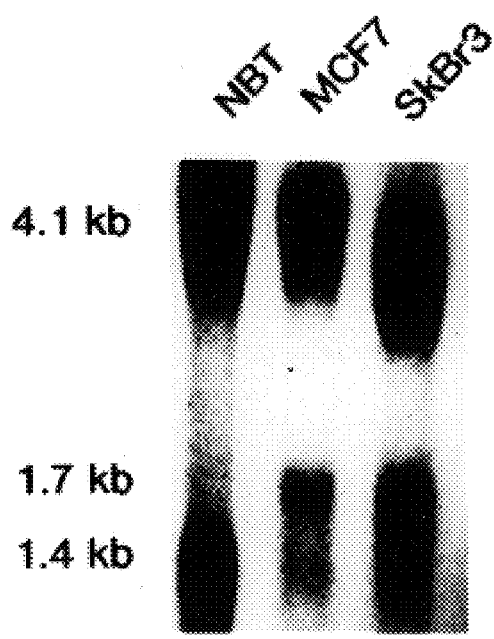

FIG. 20: Relative abundance of the individual calmodulin transcripts in normal and malignant human breast cells. Total cellular RNA was isolated from cultered human breast adenocarcinoma MCF7 and SkBr3 cell lines and from normal breast tissue (NBT) using the Trireagent (Molecular Research Center). The expression of the individual calmodulin was assayed by Northern blotting. Assignment of each RNA band to one of the calmodulin transcripts (indicated on the left) was made by comparison with an RNA ladder run on the same gel.

DETAILED DESCRIPTION OF THE INVENTION

In accordance with the present invention, it has now been discovered that oligonucleotides antisense to the mRNA encoding the three calmodulin genes expressed in PC12 cells inhibit cell proliferation and induce differentiation. The effect of the calmodulin antisense oligonucleotides was demonstrated in tissue culture experiments. The effect of over-expressing and under-expressing calmodulin in cells by transforming them with constructs containing the coding sequence from the rat calmodulin gene I in the sense and antisense orientation has also been determined. Transfection of the model neuronal PC12 cell line with a sense calmodulin gene construct increased the levels of calmodulin and the levels of calmodulin gene I mRNA, whereas transfection of PC12 cells with a calmodulin antisense construct reduced the levels of calmodulin. The major biological consequences of these molecular manipulations were that increased expression of calmodulin in the PC12 cells increased their rate of proliferation, whereas decreased expression of calmodulin inhibited their rate of proliferation. In addition, there was an inverse relationship between the cellular levels of calmodulin and the ability of PC12 cells to extend neurites. Reducing the expression of calmodulin in PC12 cells induced the extension of long viable neurites, whereas cells over expressing calmodulin lost their ability to extend stable neurites in response to treatment with NGF.

A novel observation based on these studies is that decreased levels of calmodulin in PC12 cells caused by transfection with calmodulin antisense vectors, results in spontaneous outgrowth of neuritic processes. The extension of neuritic processes is a hallmark of neuronal differentiation and is characteristically seen when nerve growth factor is added to PC12 cells[22]. The neurite outgrowth seen in the present studies was similar in character to that found upon treatment of PC12 cells with nerve growth factor in that the neurites were long, branched and stable. This is in contrast to the outgrowth obtained upon treatment with cyclic AMP or to the occasional spontaneous outgrowth found with parental PC12 cells, where the neuritic extensions are relatively short, unbranched and unstable[21].

There are several possibilities which may explain why reduced levels of calmodulin induce neurite outgrowth. Alterations of the levels of calmodulin have been shown to cause changes in the organization of microfilaments, intermediate filaments and microtubules and to affect cell morphology[55]. In addition, it has been demonstrated that increased levels of $Ca^{2+}$ and calmodulin cause microtubule depolymerization in vivo[14,26,29,33,71], effects which may be mediated by alterations in protein phosphorylation. Phosphorylation of the carboxy-terminal region of tubulin subunits by calmodulin-dependent protein kinase II has been shown to induce a dramatic conformational change, resulting in tubulin losing its capacity to assemble into microtubules[58,68]. Partially reduced intracellular levels of calmodulin may be accompanied by neurite outgrowth due to the increased stability of tubulin polymers and to the promotion of microtubule assembly. Alternatively, the effect of calmodulin antisense RNA on the morphological differentiation of PC12 cells may be secondary to the inhibition of cell proliferation, although blocking cell proliferation per se was not found to induce neurite outgrowth[20]. Finally, reduced levels of calmodulin may induce the secretion of cell adhesion molecules which, in turn, may induce neurite outgrowth. For example, it has been shown that NGF-induced neurite outgrowth is accompanied by increased secretion of transin[17], neural cell adhesion molecule (N-CAM)[37], and a laminin-binding integrin[57]. However, regardless of the mechanism involved, it is important to note that there was no significant neurite outgrowth in cells transfected with control vector grown under conditions identical to that of the calmodulin antisense transfected cells.

Earlier studies showed that NGF increased calmodulin levels in PC12 cells[4] while inducing neurite outgrowth, whereas in the present experiments decreasing the levels of calmodulin induced neurite outgrowth. This apparent discrepancy may be explained by pointing out that many factors are responsible for neurite outgrowth and that NGF may induce neurite outgrowth by mechanisms independent of calmodulin[5,28]. It is possible that NGF may be involved in one or more of the other aspects of differentiation of cells into neurons, such as in the biosynthesis of neurotransmitters and synaptic transmission[19].

The antisense calmodulin constructs of the invention may also be used in treatment of malignancy. Identification of the dominant calmodulin transcript in tumor cells will provide relevant antisense targets. Encapsulating the antisense calmodulin molecules of the invention in antibody-studded liposomes will facilitate cell-type specific targeting. Finally, operably linking the antisense calmodulin sequences to a tissue-specific promoter will facilitate tissue-specific expression and inhibition of proliferation in malignant cells.

Preparation of Oligonucleotides and Expression Vectors

Antisense oligos targeted to any known nucleotide sequence can be prepared by oligonucleotide synthesis according to known methods. Synthesis of oligonucleotides via phosphorothioate chemistry is preferred, since it is an efficient method for preparing oligodeoxynucleotides, as well as being adapted to many commercial oligonucleotide synthesizers.

Selection of a suitable antisense sequence depends on knowledge of the nucleotide sequence of the target MRNA, or gene from which the mRNA is transcribed. Although targeting of mRNA is preferred and exemplified in the description below, it will be appreciated by those skilled in the art that other forms of nucleic acid, such as pre-mRNA or genomic DNA, may also be targeted. Nucleotide sequence information is available for each of the three known calmodulin genes expressed in the rat. With respect to the oligos, the term "substantially the same as" is used herein to refer to various specific nucleotide sequences and variants thereof that would occur in a human population. Additionally, the term "substantially the same as" refers to oligomer sequences that may not be perfectly matched to a target sequence, but the mismatches do not materially affect the ability of the oligo to hybridize with its target sequence under the conditions described.

For maximum selectivity, target sequences on calmodulin mRNAs of a selected calmodulin gene should be non-homologous to corresponding regions of mRNAs encoding other calmodulin genes. For example, oligomers antisense to regions encoding the calcium binding domains on calmodulin may not be suitable because of the high conservation of nucleotide sequences in those regions. Antisense oligomers would be likely to bind to mRNAs encoding more than one calmodulin gene if such a target were chosen.

Antisense oligos should, however, be targeted to regions of the selected MRNA that encompass sequences critical for expression of the calmodulin protein. Such sequences would include, but are not limited to, translation start sites or other known ribosome binding sites on a mature mRNA. Additionally, splice sites and/or polyadenylation signals of a pre-mRNA will provide suitable targets, as well as transcriptional start sites on DNA encoding calmodulin mRNA molecules.

In a preferred embodiment, the translation start site of a mature mRNA encoding a calmodulin gene is selected as the target sequence. Also, antisense molecules will be designed that also contain sequences that are specific for the 5' unique untranslated regions of the individual calmodulin transcripts. This should facilitate the selective targeting of a specific calmodulin transcript.

Synthetic antisense oligomers should be of sufficient length to hybridize to the target nucleotide sequence and exert the desired effect, e.g., blocking translation of an mRNA molecule. However, it should be noted that smaller oligomers are likely to be more efficiently taken up by cells in vivo, such that a greater number of antisense oligomers may be delivered to the location of the target mRNA. Preferably, antisense oligomers should be at least 15 nucleotides long, to achieve adequate specificity. In a preferred embodiment, a 20-mer antisense molecule is utilized. In one preferred embodiment, this oligomer encompasses the translation start site of MRNA encoding the rat calmodulin gene I. In alternative preferred embodiments, antisense oligomers targeting the unique 5' untranslated sequences of specific calmodulin genes may also be utilized alone or in combination.

Antisense oligonucleotide sequences of different lengths may also be utilized to advantage in the present invention. Also, antisense oligomers may be targeted to other sites on RNA, and even DNA encoding the various calmodulin genes as discussed earlier.

Small oligonucleotides such as those described above are highly susceptible to degradation by assorted nucleases. Moreover, such molecules may be unable to enter cells because of insufficient membrane permeability. For these reasons, practitioners skilled in the art generally synthesize oligos that are modified in various ways to increase stability and membrane permeability. The use of modified antisense oligomers is preferred in the present invention. The term "antisense oligonucleotide analog" refers to such modified oligomers as discussed hereinbelow.

Several methods of modifying oligomers are known in the art. For example, methylphosphonate oligonucleotide analogs may be synthesized wherein the negative charge on the inter-nucleotide phosphate bridge is eliminated by replacing the negatively charged phosphate oxygen with a methyl group. Another common modification, which is utilized in a preferred embodiment of the present invention, is the synthesis of oligodeoxynucleotide phosphorothioates. In these analogs, one of the phosphate oxygen atoms not involved in the phosphate bridge is replaced by a sulphur atom, resulting in the negative charge being distributed asymmetrically and located mainly on the sulphur atoms. When compared to unmodified oligos, oligonucleotide phosphorothioates are improved with respect to stability to nucleases, retention of solubility in water and stability to base-catalyzed hydrolysis.

Other modifications of oligos to produce stable, membrane permeable oligo analogs are commonly known in the art. For a review see Cohen, J. S. (ed.) *Oligodeoxynucleotides: Antisense Inhibitors of Gene Expression,* CRC Press, Inc., Boca Raton, Fla. (1989). In addition, modified oligoribonucleotides may be utilized in the present invention. However, oligodeoxynucleotides are preferred due to their enhanced stability, ease of manufacture and the variety of methods available for analog synthesis.

Additionally, 2'-0-methyl (ribose-modified) oligos are suitable for the practice of the invention. The 2'-O-methyl sugar modification can be associated with any of the backbone linkages, including phosphorothioates, and the modification can be limited to the ends of the oligonucleotide.

Still other modifications of the oligonucleotides may include coupling sequences that code for RNase H to the antisense oligomer. This enzyme (RNase H) will then hydrolyze the hybrid formed by the oligo and the specific targeted mRNA. Alkylating derivatives of oligomers and derivatives containing lipophilic groups can also be used. Alkylating derivatives form covalent bonds with the MRNA, thereby inhibiting their ability to translate proteins. Lipophilic derivatives of oligomers will increase their membrane permeability, thus enhancing penetration into tissue. Besides targeting the mRNAs, other antisense molecules can target the DNA, forming triple DNA helices (DNA triplexes). Another strategy is to administer sense DNA strands which will bind to specific regulator cis or trans active protein elements on the DNA molecule.

Deoxynucleotide dithioates (phosphorodithioate DNA) may also be utilized in this invention. These compounds which have nucleoside-$OPS_2P$ nucleoside linkages, are phosphorous achiral, anionic and are similar to natural DNA. They form duplexes with unmodified complementary DNA. They also activate RNAse H and are resistant to nucleases, making them potentially useful as therapeutic agents. One such compound has been shown to inhibit HIV-1 reverse transcriptase.

The oligomers of the present invention and the full-length vectors may be incorporated into a variety of viral vectors. For rapidly dividing cells, vectors may be inserted into certain retroviruses. For neuronal cells that have extremely long half-lives, a neurotropic herpes simplex based viral vector may be employed. Alternatively, the calmodulin sequences of the present invention may be incorporated into adenoviruses or adeno associated virus.

The use of antibody-studded liposomes to achieve cell type specific delivery of the calmodulin antisense oligos and vectors are contemplated for use in the present invention. These antibodies will be selected based upon the cell-type to be targeted. For example, the epidermal growth factor receptor is known to be overexpressed in malignant glioma cells. Efficient targeting of the constructs of the invention will be facilitated by the use of such liposomes.

To achieve cell type specific expression, the calmodulin sequences will be operably linked to cell type specific promoters. For example, the GFAP promoter will be used to express calmodulin antisense constructs in glioma cells.

Administration of Antisense oligonucleotides and Sense or Antisense Expression Vectors Antisense oligomers as described herein are generally administered to a patient as a pharmaceutical preparation. The term "patient" as used herein refers to human or animal subjects.

The pharmaceutical preparation comprising the antisense oligomers of the invention are conveniently formulated for administration with an acceptable medium such as water, buffered saline, ethanol, polyol (for example, glycerol, propylene glycol, liquid polyethylene glycol, and the like), dimethyl sulfoxide (DMSO), oils, detergents, suspending agents or suitable mixtures thereof. The concentration of antisense oligomers in the chosen medium will depend on the hydrophobic or hydrophilic nature of the medium, as well as the length and other properties of the antisense molecule. Solubility limits may be easily determined by one skilled in the art.

As used herein, "biologically acceptable medium" includes any and all solvents, dispersion media and the like which may be appropriate for the desired route of administration or the pharmaceutical preparation, as exemplified in the preceding paragraph. The use of such media for pharmaceutically active substances is known in the art. Except insofar as any conventional media or agent is incompatible with the antisense molecules to be administered, its use in the pharmaceutical preparation is contemplated.

Selection of a suitable pharmaceutical preparation depends upon the method of administration chosen. For example, antisense oligomers to calmodulin or vectors encoding them may be administered for treatment of brain tumors by direct injection into regions of the brain containing the malignant tumor. In this instance, a pharmaceutical composition comprises the antisense molecule dispersed in a medium that is compatible with cerebrospinal fluid. In a preferred embodiment, artificial cerebrospinal fluid (148 mM NaCl, 2.9 mM KCl, 1.6 mM $MgCl_2 \cdot 6\ H_2O$, 1.7 mM $CaCl_2$, 2.2 mM dextrose) is utilized and oligonucleotides antisense to calmodulin mRNA are provided to neuronal tissue by intraventricular injection or by direct injection into the malignant tumor. In alternative embodiments, the pharmaceutical compositions may be administered by direct injection into any solid tumor.

Oligonucleotides antisense to calmodulin MRNA may also be administered parenterally by intravenous injection into the blood stream, or by subcutaneous, intramuscular or intraperitoneal injection. Pharmaceutical preparations for parenteral injection are known in the art. If parenteral injection is selected as a method for administering the antisense oligonucleotides, steps must be taken to ensure that sufficient amounts of the molecules reach their target cells to exert a biological effect. For example, when brain tissues are targeted, the lipophilicity of the antisense molecules, or the pharmaceutical preparation in which they are delivered may have to be increased so that the molecules can cross the blood-brain barrier to arrive at their target locations. Furthermore, the antisense molecules will have to be delivered in a cell-targeting carrier so that sufficient numbers of molecules will reach the target cells. Methods for increasing the lipophilicity of a molecule are known in the art, and include the addition of lipophilic groups to the antisense oligonucleotides.

Several techniques have been used to increase the stability, cellular uptake, and biodistribution of oligonucleotides. Antisense oligomers of the present invention may be encapsulated in a lipophilic targeted carrier such as a liposome. One technique is to use as a carrier for the oligonucleotide is a liposomal preparation containing the cationic lipid N-[1-(2,3-dioleoyl)propyl]-N,N,N-trimethyl ammonium chloride (DOTMA; lipofectin). To further facilitate targeting of the antisense oligonucleotides, antibody-studded liposomes may be utilized. The antibody mediates the targeting of the antisense construct to the desired tissue type and the liposome moiety mediates the membrane fusion event necessary for the construct to enter the target cell.

Vectors containing sense or antisense calmodulin constructs or oligonucleotides may be administered in several ways. Retroviruses are viral vectors which can express foreign genetic material only within dividing cells. They are useful vectors for gene delivery to tumor cells and especially to malignant hematopoietic cells. For transduction of non-dividing cells within the brain, vectors bases upon DNA viruses have been employed: adenoviruses, herpes simplex viruses, and more recently adeno-associated viruses (AAV). Adenoviral vectors are capable of efficiently transferring the exogenous DNA to both proliferating and non-proliferating cells. Once localized in the nucleus, they function in an epi-chromosomal fashion to express the new gene, which means that their expression will eventually wane, and the vectors will have to be readministered in order to maintain the persistent normal expression and function. When the vector is readministered, however, it frequently causes an immune response which prevents it from entering the target cells. AAV may be used to advantage in the treatment of certain pathological conditions as readministration may not be required. AAV has been shown to intergrate at a specific site on chromosome 19. Defective herpes simplex virus (HSV) based vectors are very suitable for the delivery of genes into neurons, because HSV is a naturally neurotropic virus. These vectors at present, however, are often cytotoxic and have the potential to reactivate latent viruses which exist within most adults. Another concern may arise from the fact that viral sequences from the HSV vectors incorporate into the host genome. AAV are suitable for developing viral vectors, because they are nonpathogenic parvoviruses which are incapable of autonomous replication and spread. They are however, relatively small vectors and therefore create a limit on the size of the foreign genetic sequence which they can deliver.

In theory, non-viral plasmid-liposome complexes have many advantages as gene transfer vectors, in that they can be used to transfer expression cassettes of essentially unlimited size, cannot replicate or recombine to form an infectious agent, and may evoke fewer inflammatory or immune responses because they lack proteins. The disadvantage of these vectors is that they are inefficient, requiring that thousands of plasmids be presented to the target cell in order to achieve successful gene transfer. One possibility to increase the efficiency of gene transfer with plasmid vectors is to utilize the endosomolytic properties of adenoviruses. A major part of the plasmid DNA-lipid complexes after in vivo administration are trapped within the endosomal vesicles and cannot reach the nucleus. If the plasmid vector DNA is administered in the form of a molecular conjugate, consisting of the plasmid vector DNA linked to a receptor and adenovirus, a greater proportion can escape the endosome and reach the nucleus.

The problem of insufficient cellular uptake of both plasmid DNA vectors and oligonucleotides can be partially overcome by coupling them to carrier ligands that recognize internalizable receptors on the cell membrane. For example, calmodulin antisense oligomers or a plasmid expression vector can be coupled to a monoclonal antibody against a tumor-associated antigen and thus deliver the calmodulin antisense sequence only to the malignant cells. One suitable monoclonal antibody (MoAb) is MoAb 7.16.4 (IgG2a subclass) which recognizes the c-erb2 ligand found originally on rat neuro/glioblastomas and expressed also by human breast carcinomas with poor prognosis. The phosphorothioate antisense oligomers can be cross-linked to monoclonal antibodies by means of a phosphorothioate-maleimide method. Another possibility of coupling vector DNA or oligomers to monoclonal antibodies in order to enhance cellular uptake and improve the specificity is by the production of antibody targeted liposomes.

A suitable strategy to deliver calmodulin antisense sequences (oligomers or vectors) would be to take advantage of the fact that rapidly dividing cells are transfected with greater efficiency than non-dividing cells. In cases of rapidly proliferating malignant tumors, this would allow the calmodulin antisense sequences to be taken up and exert an effect preferentially in the tumor cells which have elevated levels of calmodulin, but not the normal surrounding cells. This way greater selectivity and safety can be achieved. In order to test this strategy for the delivery of calmodulin antisense sequences, experiments will be performed in vitro on mixed cultures of normal and cancer cell lines which have different rates of proliferation, or in vivo using mouse models with transplanted tumors which have different grades of malignancy.

Oligonucleotides have the advantage over many vector systems for gene delivery that do not incorporate foreign genetic material into the host genome. They, however, do not easily penetrate cell membranes and have a limited half-life in vivo. Therefore, repeated administration will be necessary in order to achieve a therapeutic effect. Oligonucleotides have a great potential as therapeutic agents in cancer if the problems associated with delivery are overcome. The "gene therapy" approach would be more suitable in neurodegenerative disorders where the therapeutic substance would be administered as rarely as possible. This approach would also be suitable for the treatment of intracranial tumors, because multiple administration of the therapeutic substance would be avoided.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation comprising the antisense oligomers may be administered at appropriate intervals, for example, twice a day until the pathological symptoms are reduced or alleviated, after which the dosage may be reduced to a maintenance level. The appropriate interval in a particular case would normally depend on the condition of the patient.

The following examples are provided to describe the invention in further detail. These examples are intended merely to illustrate and not to limit the invention.

EXAMPLES

To examine the fundamental role calmodulin plays in the growth and differentiation of PC12 cells, we have determined the effects of over-expressing and underexpressing calmodulin in these cells by transfecting them with constructs containing the coding sequence from rat calmodulin gene I in the sense and antisense orientation. We have also synthesized oligonucleotide antisense 20-mers for each of the three calmodulin genes expressed in PC12 cells and have assayed their effects on neuronal cell growth and differentiation.

Use of the calmodulin constructs of the invention for the treatment of malignancies is also exemplified herein.

MATERIALS

The enzymes used for the molecular cloning techniques were purchased from New England Biolabs, Inc. (Beverly, Mass.). Agarose was obtained from Sigma Chemical Co. (St. Louis, Mo.). The PC12 cell culture and transfection reagents, including Dulbecco's Modified Eagle Medium (DME), fetal bovine serum (FBS), horse serum, Opti-MEM I medium, Lipofectin Reagent [1:1 liposome formulation of the cationic lipid N-[1-(2,3-dioleoyl)propyl]-N,N,N-trimethylammonium chloride (DOTMA) and dioleoyl phosphatidylethanolamine (DOPE) in membrane-filtered water] and G418 sulfate (Geneticin) were purchased from GIBCO BRL (Gaithersburg, Md.). Purified collagen, Vitrogen 100, was from Celtrix Laboratories (Palo Alto, Calif.). Purified mouse nerve growth factor (NGF) was a generous gift of Dr. Eugene Johnson, Jr. (Washington University School of Medicine, St. Louis, Mo.). Trireagent was acquired from Molecular Research Center (Cincinnati, Ohio), and the DNA purification columns were from QIAGEN (Chatsworth, Calif.). The materials for labeling of the oligonucleotide and DNA probes, employed in the Northern analyses, with digoxigenin-11-dUTP and for detecting them by chemiluminescent techniques were obtained from Boehringer Mannheim (Indianapolis, Ind.). Maximum Strength Nylon Membranes, 0.2 $\mu$m, were purchased from Schleicher & Schuell (Keene, N.H.). All other chemicals were molecular biology grade and were purchased from Sigma Chemical Co.

METHODS

Cell culture

PC12 cells, generously provided by Dr. William Hait (The Cancer Institute of New Jersey, Piscataway, N.J.), were cultured in Dulbecco's Modified Eagle Medium (DME) supplemented with 10% fetal bovine serum, 5% horse serum (complete medium) at 37° C. in a humidified atmosphere with 6% $CO_2$. The medium was changed twice each week. For passaging and subculturing, the cells were mechanically dislodged from the culture vessels using glass beads. The cells were routinely grown in culture flasks without collagen coating. In all experiments the culture dishes were pretreated with 100 mg/ml purified collagen (Vitrogen 100).

Conditioned medium, used during the initial selection with Geneticin, was obtained from high density PC12 cell cultures ($10^6$cells/ $cm^2$), passed through 0.2 $\mu$m filters, and stored at −20° C. as described previously[40].

In the experiments in which the effects of NGF were studied, the cells were plated onto collagen-coated 24-well tissue culture dishes at a density of $2\times10^4$ cells/$cm^2$. After 24 hours, purified mouse NGF was added to the cells at a final concentration of 50 ng/ml in complete medium. The cell culture medium containing NGF was changed every third day.

The human U-87 MG, U- 118 MG and DBTRG-05 glioblastoma cell lines, and the HCN-1A cortical neurons will be cultured in Dulbecco's modified Eagle's medium (DMEM) containing 10% FBS and other supplements as suggested by the American Type Culture Collection. The normal brain glial cell line CHII will be cultured in DMEM containing 10% FBS. The glioblastoma cell lines and the cell-specific monoclonal antibody to the human EGF receptor MoAb 425 will be provided by Dr. Rodeck.

The human breast cancer cell lines (MCF7, SKBr3, T47D) and the nonmalignant immortalized cell lines from normal mammary tissue (184, 184A, 184B) will be obtained from the American Type Culture Collection. The breast cancer cells will be routinely cultured in Dulbecco's modified Eagle's Medium, supplemented with 2 mM 1-glutamine, 1 mg/ml gentamycin, 2.5 $\mu$g/ml fungizone, 10 $\mu$g/ml insulin and 5–10% fetal bovine serum at 37° C. in a humidified atmosphere with 5% $CO_2$. Cell lines 184, 184A and 184B will be routinely cultured in MCDB 170 medium, supplemented with 5 ng/ml epidermal growth factor (EGF), 500 ng/ml hydrocortisone, 10 $\mu$g/ml insulin, 70 $\mu$g/ml bovine pituitary extract, 10 $\mu$M isoproterenol, and 5 $\mu$g/ml transferrin.

Plasmid expression vectors

Figure 1:
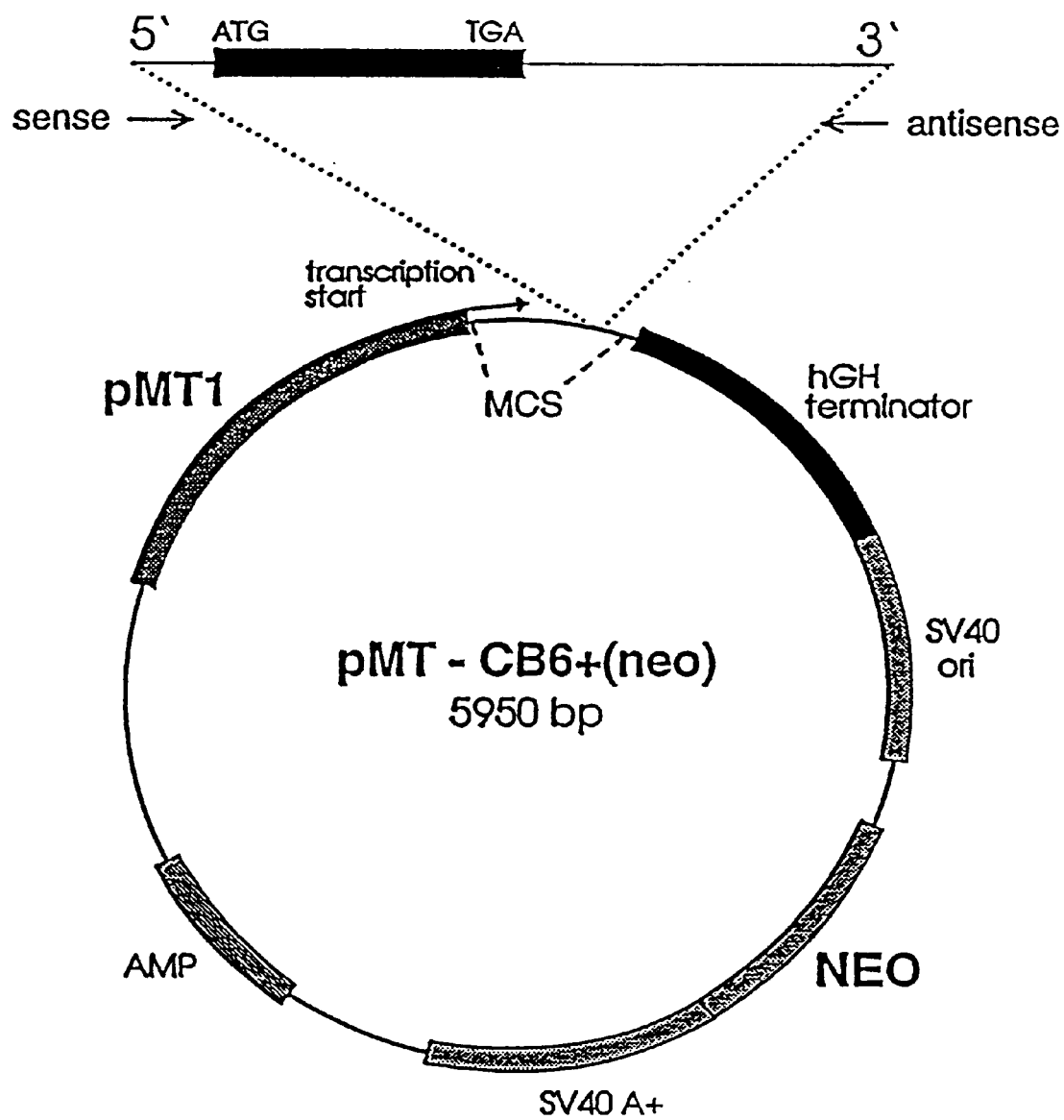
FIG. 1: Schematic representation of the plasmid constructs used for the generation of stable PC12 cell clones. Calmodulin (CaM) antisense and calmodulin sense vectors were prepared by inserting a BamH1-BamH1 restriction fragment from clone pRCM1, which contains the full-length 1.4 kb cDNA from rat CaM gene I, into the BamH1 site of the eukaryotic expression plasmid pMTCB6$^+$(neo). The CaM 0.48 kb coding region is represented by a black rectangle, and the initiation (ATG) and termination (TGA) codons are as indicated. The elements of the eukaryotic expression vector are: pMT1, sheep metallothionein promoter; NEO, neomycin/Geneticin resistance gene; AMP, ampicillin resistance gene; MCS, multiple cloning site; hGH, human growth hormone transcription termination signal; SV40 ori, SV40 origin; SV40 A+, SV40 polyadenylation signal; BamH1, restriction enzyme site in the vector polylinker used for subcloning the CaM CDNA.

Vectors generating rat calmodulin antisense and sense RNA sequences were constructed using standard recombinant DNA techniques[59]. A detailed schematic description of the elements in the cloning vectors is given in FIG. 1. The plasmid pRCM1, harboring a full-length 1.4 kb cDNA from rat calmodulin gene I[49], was generously donated by Dr. Hiroshi Nojima (Osaka University, Osaka, Japan). The eukaryotic expression vector MT-CB6+ (neo) was generously supplied by Dr. Frank Rauscher III (The Wistar Institute, Philadelphia, Pa.). This vector contains a 1.7 kb Pvul - BamH1 fragment from the $Zn^{2+}$-inducible sheep MT-1 promoter[52] and a neomycin-resistance gene for selecting stable transfectants. A BamH1-BamH1 restriction fragment from pRCM1, containing the 1.4 kb calmodulin cDNA was subcloned in the antisense or sense orientation in vector pMT-CB6$^+$ (neo). The orientation of the calmodulin inserts was ascertained by restriction enzyme analysis and nucleic acid sequencing.

The three individual calmodulin genes have distinct sequences in their 5' untranslated regions (UTR)[47]. These sequences are sufficiently different from each other to allow the design of antisense sequences specific for each calmodulin gene. The selective inhibition of the expression of the individual calmodulin genes may be achieved by using vectors producing antisense RNA molecules targeted to these unique sequences. It has already been demonstrated that calmodulin antisense oligodeoxynucleotides targeted to the 5' UTR selectively inhibit the proliferation of PC12 cells. However, although the individual calmodulin genes have distinct 5' UTRs, the individual transcripts derived from the calmodulin genes that encode two transcripts (i.e., calmodulin genes I and III) have identical 5' regions, and therefore, targeting the 5' regions will not distiguish between the two transcripts derived from a single gene. These transcripts do, however, have different 3' UTRs since they are generated by the use of different polyadenylation sites[47,48]. To selectively inhibit these individual transcripts, the unique sequences in the 3' regions will be targeted. The 5' UTR regions of calmodulin genes I, II and III will be amplified by PCR from the plasmids carrying the cDNAs from the respective genes (pRCM1, pRCM3, pRCM4; donated by Dr. Hiroshi Nojima, Osaka University, Japan).

The following portions of the cDNAs from the individual calmodulin genes will be amplified by PCR using sequence-specific primers and will be used to create the calmodulin gene-specific antisense RNAs: CaM gene I (−110 to +5); CaM gene II (−68 to +3); CaM gene III (−96 to +4). The primer sequences were chosen using a primer selection program (Oligo, National Biosciences, Hamel, Minn.). A homology search of the Genbank sequence data base using the Genepro software (Riverside Scientific Enterprises, Bainbridge Island, Wash.) was performed on the 5' UTR from calmodulin genes I, II and III and the individual primers. The 5' UTR from CaM genes I, II and III shared 70% or less overall homology among each other and did not share significant homology (i.e., 80% identity) with any sequence (except the target sequence) from the Genbank database. Primers sets were not utilized if a significant match was seen with any sequence in the database.

The PCR conditions for the three different primer pairs have been determined on the basis of the calculated melting temperature (Tm) for the primer having the lower T, of the pair. The resulting PCR products will be subcloned into the vector pCR3 (Invitrogen). The orientation of the inserts will be verified by nucleic acid sequencing (performed at the Nucleic Acid Facility, Department of Chemistry, University of Pennsylvannia). A calmodulin gene I antisense vectro has already been generated using the above described methodology. All plasmids (with and without inserts) will be purified using Qiagen columns (Chatsworth, Calif.).

The β-galactosidase reporter plasmid CMV-βgal[64], which was used to determine the uptake of the plasmids into PC12 cells, was generously provided by Dr. Frank Rauscher III (The Wistar Institute).

Plasmid DNA used for the transfection experiments was prepared using QIAGEN columns according to the procedure recommended by the manufacturer.

Transfection with expression vectors

PC12 cells were transfected with the various constructs using lipofectin according to the procedure of Muller[44]. Briefly, the cells were seeded onto collagen-coated 100 mm dishes at a density of $4\times10^5$ cells/ml and incubated overnight. Immediately before transfection, the cells were washed three times in serum-free Opti-MEM I medium. Supercoiled plasmid DNA (5 μg/ml) and lipofectin (20 μg/ml) in Opti-MEM medium were mixed in polypropylene tubes and preincubated for 5 minutes at room temperature before being added to the cells. To determine the efficiency with which the PC12 cells took up the plasmid, the cells were cotransfected with 5 μg/ml of the specified calmodulin DNA and 1 μg/ml of the reporter plasmid pCMV β-gal. After incubation for 5 hours at 37° C., Opti-MEM I medium containing 10% fetal bovine serum and 5% horse serum was added to the cell cultures (4 ml/100 mm dish) without removing the transfection medium. After 12 hours, the transfection medium was replaced with complete medium. Selection of stable clones was initiated 48 hours after transfection with 400 μg/ml Geneticin. During the initial isolation of Geneticin—resistant colonies, PC12 cell conditioned medium was added to 10% v/v in complete medium in order to facilitate the growth of the low-density cultures. The stable antisense and sense PC12 cell clones, obtained from the Geneticin-resistant colonies, were maintained in complete Dulbecco's modified Eagle's medium (DMEM), containing 250 μg/ml Geneticin.

In situ staining of cells for β-galactosidase activity

Expression of β-galactosidase was assayed by a histochemical procedure using the substrate X-Gal (5-bromo-4-chloro-3-indolyl-β-D-galactopyranoside) as described elsewhere[36]. The cells were washed twice with phosphate-buffered saline (PBS; 137 mM NaCl, 2.7 mM KCl, 4.3 mM $Na_2HPO_4$, 1.47 mM $KH_2PO_4$), pH 7.1, then fixed for 15 minutes in 0.1 M sodium phosphate, pH 7.0, containing 0.25% glutaraldehyde and 1 mM $MgCl_2$. The cells were washed three times for 10 minutes with PBS, and the samples were incubated with X-Gal solution at 37° C. for 60 minutes. The cells were observed with a light microscope equipped with Hoffman modulation optics. For each sample, a total of 1000 cells were counted. The efficiency with which the cells took up the vector was expressed as the percentage of total cells which were positive for β-galactosidase.

Assays of cell number and neurite outgrowth

To determine the cell number and differentiation score, the cells were seeded in 24-well plates at a density of $5\times10^4$ and $2\times10^4$ cells/cm$^2$, respectively. The cell counts were done by scoring the cell numbers in a given microscopic field at various time periods. Photographs of the cell monolayers were taken periodically for subsequent measurements of neurites. Neurite outgrowth was evaluated using a differentiation score based on the number of neurites per cell and on the relative lengths of the neurites[4]. According to this system, undifferentiated cells yield a score of zero, and the maximum differentiation score is three.

For $Zn^{2+}$ treatment, the cells were incubated with 80 μM $ZnSO_4$ for 6 hours, followed by removal of the medium and addition of complete medium.

RNA extraction and analyses of calmodulin RNA levels By Northern and slot-blot

Total cellular RNA was isolated from cultured cells with Trireagent according to the instructions of the manufacturer. The Trireagent method is a modified version of the single step acid guanidinium isothiocyanate-phenol-chloroform method for RNA extraction[9]. The sizes and the sequences of the oligonucleotide probes specific for the calmodulin gene I and gene II mRNAs are described elsewhere[74]. The calmodulin gene I oligonucleotide probe was 3'-end labeled with digoxigenin-11-dUTP using the Genius 5 oligonucleotide labeling kit and resuspended at a concentration of 5 pmol/ml in 10 mM Tris-HCl, 1 mM EDTA, pH 8. To normalize the poly (A)$^+$ mRNA content in the various total cellular RNA samples, a cyclophilin DNA probe was used. This probe was labeled with DIG-11-dUTP using PCR amplification with SP6 and T7 primers of a 636 bp cyclophilin fragment, subcloned in pGEM3Z[4].

For the Northern blot, total cellular RNA (5 μg) was subjected to electrophoresis on a 1.2% agarose/formaldehyde gel and transferred by capillary blotting to 0.2 μm nylon membranes. For the slot-blot analyses, 10 μg or 2.5 μg of total cellular RNA were resuspended in 120 μl of 5×SSC and 12% formaldehyde in diethylpyrocarbonate (DEPC) - treated water, incubated for 15 minutes at 60° C., and then blotted onto 0.2 μm nylon membranes using a Minifold II slot-blot apparatus (Schleicher and Schuell). The RNA samples subjected to Northern or slot-blotting were fixed onto the membranes by baking at 80° C. for 2 hours. Prehybridization for the detection of calmodulin gene I was performed at 42° C. in 5×SSC, 0.02% sodium dodecyl sulfate, 0.1% N-laurylsarcosine, 2% blocking reagent for nucleic acid hybridization and 20 mM sodium maleate, pH 7.5. Hybridization with the calmodulin oligonucleotide probes was carried out at 42° C. for 16 hours. Prehybridization and hybridization with the cyclophilin probe were carried out at 55° C. in a solution of 5×SSC, 0.4% SDS, 0.1% N-laurylsarcosine, 2% blocking reagent, and 50% formamide in 20 mM sodium maleate, pH 7.5. The filters were then washed twice in 2×SSC containing 0.1% SDS for 5 minutes at room temperature, followed by two 15 minutes washes (the last wash being done at 50° C. for the calmodulin gene I probe and at 65° C. for the cyclophilin probe) in 0.5×SSC containing 0.1% SDS. The membranes were rinsed briefly in 0.1 M maleic acid, 0.15 M NaCl and 0.3% Tween 20 (washing buffer) and were blocked for 1 hour at room temperature with 1% blocking reagent, 0.1 M maleic acid and 0.15 M NaCl. The blots were subsequently incubated for 30 minutes at room temperature with an alkaline phosphatase - conjugated anti-digoxigenin antibody (Boehringer), washed thoroughly in washing buffer, equilibrated in 0.1 M Tris-HCl containing 0.1 M NaCl, pH 9.5, and treated with the chemiluminescence substrate Lumigen PPD (Boehringer). The blots were then exposed to an X-ray film (Kodak, Rochester, N.Y.). The optical density of the autoradiograms was quantified using the Drexel University Image Analysis System (DUMAS)[16].

Immunofluorescent assay for calmodulin

Calmodulin levels were estimated with an indirect immunofluorescent assay according to a modification of the procedure of Natsukari et al[45]. PC12 cells were cultured for 24 hours in multi-chamber slides (NUNC, Roskilde, Denmark) precoated with 100 μg/ml collagen. The cells were rinsed in PBS, pH 7.4, and fixed with PBS containing 3% paraformaldehyde and 0.25% glutaraldehyde for 45 minutes at room temperature. The samples were washed in 0.05% Tween in PBS, and the nonspecific protein-binding sites were blocked by treatment with 2% bovine serum albumin (BSA) in PBS for 1 hour at 37° C. Following three 10 minute washes in PBS-Tween, the cells were incubated for 1 hour at 37° C. with a primary mouse anti-calmodulin monoclonal antibody, Clone 6D4 (Sigma), diluted 1:120 in PBS-Tween. The slides were then washed in PBS and incubated for 1 hour at 37° C. with a secondary FITC-conjugated rabbit anti-mouse IgG antibody (Sigma) diluted 1:120 in PBS-Tween. The samples were washed in PBS, mounted with Slow Fade Medium (Molecular Probes, Inc., Eugene, Ore.) and observed with a Leitz Diaplan fluorescence microscope. Photographs were taken with a Leitz Orthomat E automatic microscopic camera. Calmodulin levels in individual cells were quantified by imaging the film using a Nikon model XC-77 CCD video camera and determining the fluorescence intensity associated with each cell using the DUMAS[16]. The results are expressed as OD values based on the gray scale level. Pseudocolor images were generated using the DUMAS for illustration.

Antisense Oligodeoxynucleotides

Based on the cDNA sequences for the three calmodulin genes expressed in PC12 cells, a set of 20-mer phosphorothioate oligodeoxynucleotides were designed and synthesized. The antisense oligos were targeted to the areas of the respective calmodulin CDNA sequences bridging the initiation codons. As a controls, a series of random oligo sequences of similar size were also synthesized and assayed.

Treatment of PC12 Cells with antisense oligomers specific for calmodulin

Figure 11:
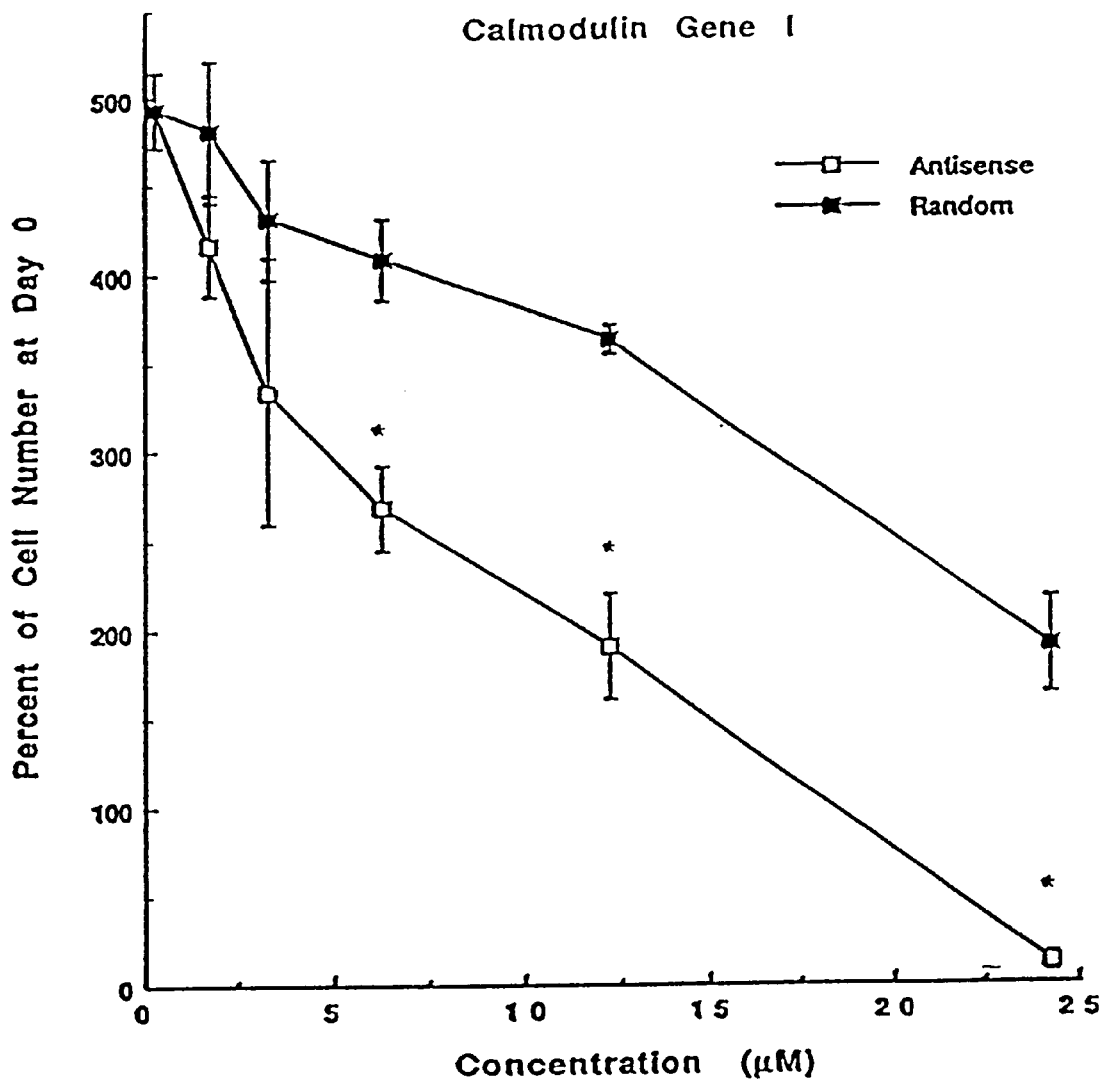
Figure 11:
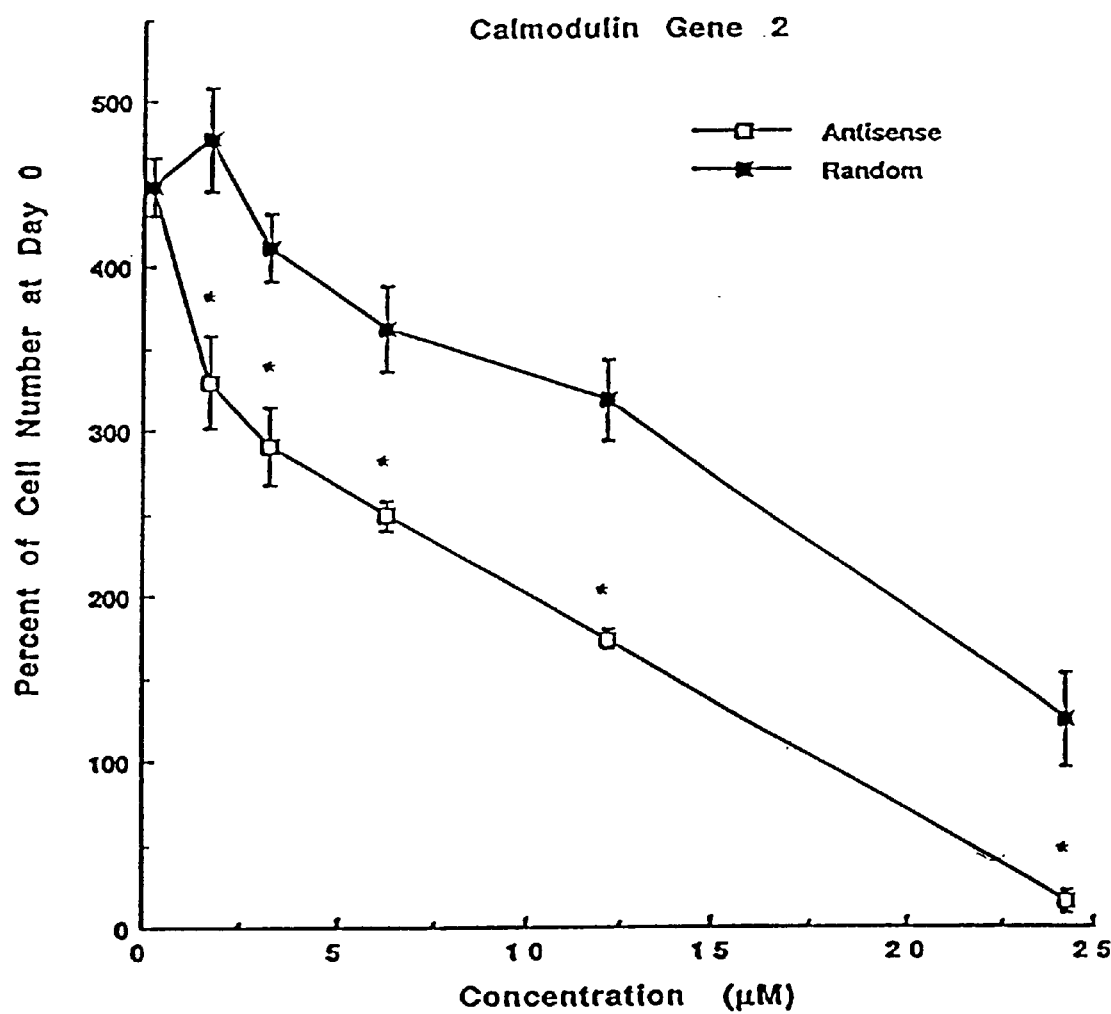
Figure 11:
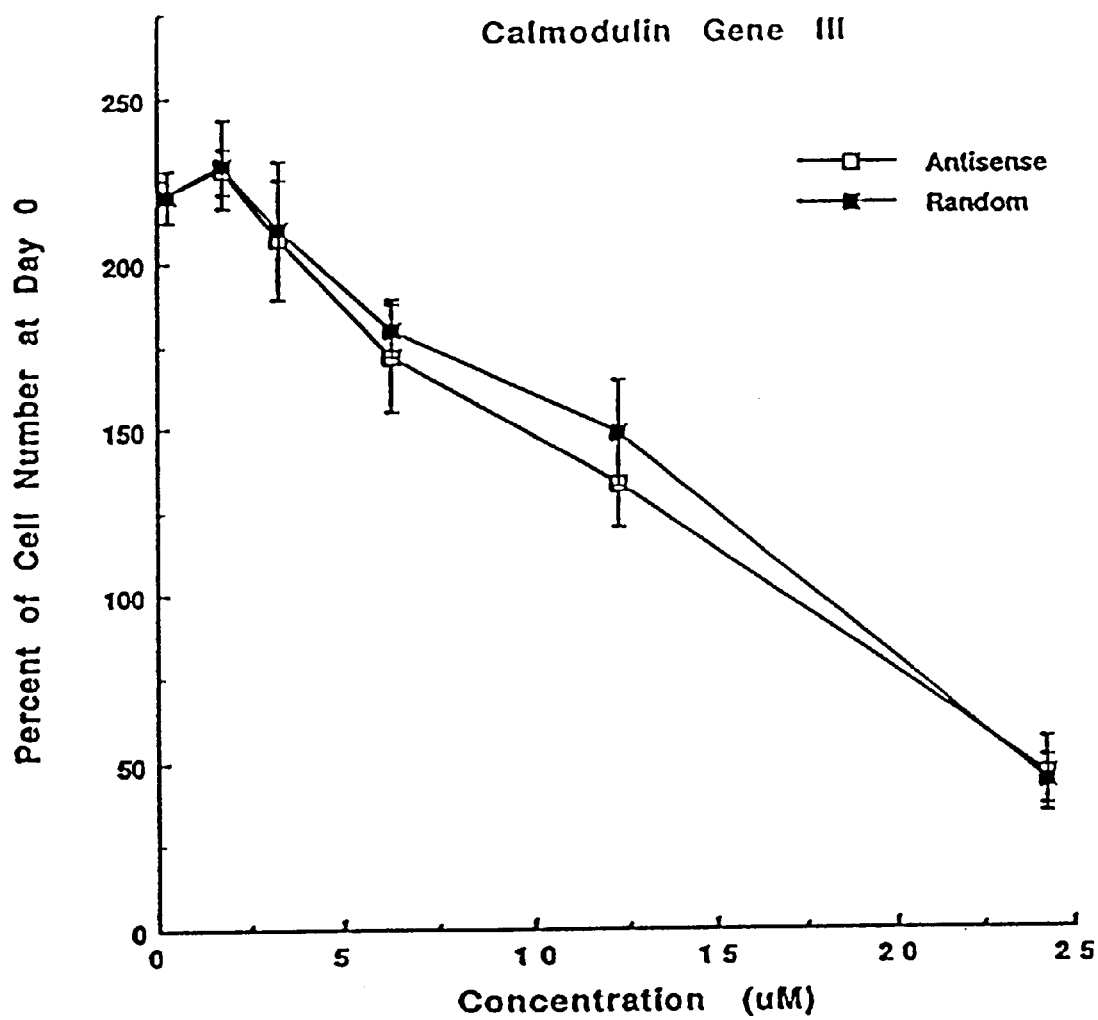

PC12 cells were incubated with DMEM containing 1.6 μM insulin and 0.5 mg/ml BSA. Vehicle (DMEM), random oligo, or calmodulin antisense oligos were added to the media at the concentrations indicated. Cell proliferation was determined by counting the number of cells in pre-designated areas of the microscopic field at various times after adding the oligomers. The data presented are expressed as the number of cells at a given time interval as percentage of the number of cells at day 0. As the three calmodulin antisense oligos were used in combination, the indicated concentrations of calmodulin antisense denote the total combined concentration (FIGS. 8 and 9). In additional experiments the calmodulin antisense oligomers were applied to PC12 cells separately (FIG. 11 and Table III).

Statistical analyses

The results were evaluated using one-way or two-way analysis of variance (ANOVA), as appropriate, followed by post-hoc multiple comparisons using the Student-Newman-Keuls Method.

Uptake of calmodulin constructs in glioblastoma cell lines

The glioblastoma cell lines, (U-87 MG and U-118 MG) and normal glial cells (CHII) will be used to assess the inhibitory properties of the calmodulin constructs in neoplastic cells. First, the efficiency of DNA delivery by means of antibody-liposome-DNA complexes will be determined in vitro (the DNA will be either antisense oligodeoxynucleotides or an antisense expression vector). For this purpose, antibody-liposome-DNA complexes will be prepared with FITC-labeled oligodeoxyoucleotides or a β-galactosidase reporter vector. The complexes will then be added to the glioblastoma and normal glial cells. Normal glial cells do not express the MoAb 425 reactive antigen and, therefore, are not expected to take up the antibody-liposome-DNA complexes. The degree of uptake will be compared between glioblastoma cells with very high (U-87 MG) and almost undetectable (U-118 MG) levels of the EGF receptor. The uptake of the FITC-labelled oligodeoxynucleotides will be determined using an immunocytochemical fluorescent assay. The penetration and expression of the vector in cells will be assessed using an in situ β-galactosidase histochemical assay to detect the expression of the reporter gene. Using these reporter systems, the conditions will be optimized for delivering the antibody-liposome-DNA complexes. Controls for the specificity of delivery will be performed by preincubating cells with free MoAb 425, or free isotype-matched MoAb with irrelevant specificity, and determining whether either treatment abolishes the binding (and therefore the fluorescent or histochemical β-galactosidase signals) of the antibody-liposome-DNA complex.

Antibody-liposome-DNA complexes will be prepared using the individual calmodulin antisense oligodeoxynucleotides or antisense vectors. The effects of inhibiting the individual calmodulin mRNAs in the different cell lines will be assessed by measuring cell proliferation (direct cell counting; MTT calorimetric assay; synthesis of DNA) and evaluating the appearance of differentiation (morphological evaluation; immunocytochemical determination of the presence of the differentiation marker GFAP). The levels of the calmodulin mRNAs will be measured using Northern blot analysis of total cellular RNA as described earlier, and the levels of calmodulin will be measured using immunoblot analysis of SDS-lysates from the cells. In case the cell number is insufficient for immunoblot (due to inhibition of cell proliferation), determination of changes in the levels of calmodulin will be performed immunocytochemically with a FITC-labelled or horseradish-peroxidase labelled anti-calmodulin MoAb, as performed previously in this laboratory[45]. The controls described earlier (empty cloning vector, random oligodeoxynucleotides) will also be included in these studies. These experiments will yield information about the significance of antigen density for the uptake of the antibody-liposome-DNA complexes and for the anti-tumor activity of the different calmodulin antisense agents.

Purification of antibodies

Mouse MoAb 425 (specific for the epidermal growth factor receptor) will be supplied by Dr. Ulrich Rodeck (The Wistar Institute) in the form of ascites obtained from pristane-primed hybridoma-bearing mice. The monoclonal antibody will be purified on a Protein A-Sepharose column[117].

Preparation and administration of antibody-liposome-DNA complexes

Complexes will be prepared that contain two types of DNA, either antisense oligodeoxynucleotide or plasmid expression vectors.

a. Preparation of antibody-liposome-DNA complexes. Liposomes containing DNA and covalently coupled with a purified monoclonal antibody 425 on the outer surface will be prepared as described[123,126,127]. Since the lipid composition is critical for efficient delivery of liposomes[128], the ratio of the lipids used to form the liposomes will be varied in order to achieve optimal delivery.

Transfection of antibody-liposome-DNA complexes in vitro will also be assessed. Logarithmically growing cells will be placed onto culture plates and incubated with the antibody-liposome-DNA complexes[125]. In the initial experiments, the amount of vector and oligodeoxynucleotides and their ratio to the liposome-forming lipids will be optimized.

The specificity of delivery using the monoclonal antibody approach will also be assessed. The specificity of delivery will be demonstrated in two ways. Glioblastoma cells bearing the MoAb 425 reactive antigen (the EGF receptor) will initially be incubated with increasing concentrations of uncomplexed MoAb 425. The MoAb-liposome-DNA complexes will then be added, and the reduction in the transfection efficiency by preincubation with the free MoAb will be determined using a β-galactosidase reporter vector. Other tests of specificity will be provided by performing similar experiments with an isotype-matched (IgG2a) MoAb H24B5. This antibody is specific for an antigen on the influenza virus and does not cross-react with the MoAb 425 epitope. Also glial cells that do not express the antigen for MoAb 425 (CH II) will be assessed for uptake of antibody-liposome-DNA complexes.

Efficiency of antibody-liposome-oligodeoxynucleotide uptake in glioblastoma cells The efficiency by which the oligodeoxynucleotides encapsulated in antibody-coated liposomes are taken up into the cells will be determined using an immunocytochemical fluorescent assay of calmodulin antisense oligodeoxynucleotides, labelled at the 3' end with fluorescein isothiocyanate (FITC) and detected with a Leitz Diaplan fluorescent microscope. This method of labeling and detecting the uptake of oligodeoxynucleotides has been chosen since it has already been successfully employed to study the uptake of other antisense oligodeoxynucleotides in mouse brain[18]. Cells which do not express the MoAb 425 target antigen (CHII) will be used as a control for nonspecific binding. The subcellular distribution of the FITC-labeled oligodeoxynucleotides will be determined using confocal microscopy imaging[115].

The delivery of the vector DNA encapsulated by the antibody-coated liposomes to cells will also be evaluated using an in situ histochemical assay for *E. coli* β-galactosidase. This assay will be performed in cultured cells and in vivo in mouse tissue. Antibody-coated liposomes complexed with the reporter vector CMV-β-gal (gift of Dr. Frank Rauscher III, The Wistar Institute, Philadelphia) will be used. The expression of β-galactosidase will be assayed by a histochemical procedure using the substrate X-Gal (5-bromo-4chloro-3-indolyl-β-D-galactopyranoside) as described by MacGregor et al[36]. Cells transfected with vector lacking the reporter gene will serve as controls for endogenous galactosidase activity.

Preparation of expression vectors with the GPAP promoter

The construction of the reporter and calmodulin expression vectors will be performed using standard molecular cloning techniques[135]. A β-galactosidase reporter vector will be constructed as follows. The human GFAP promoter (the entire 5' region which contains GFAP sequences from bp −2163 to +47, where the RNA start site is +1) will be obtained from plasmid pGfaCAT-2[130]. The promoter will also contain the region downstream of the RNA start site which is critical for efficient transcription[130]. The GFAP promoter will be used to replace the metallothionein promoter in vector pMT-CB6+ (the MT-I promoter will be excised using EcoRI). The *E.coli* β-galactosidase (LacZ) gene will be excised from the vector pSV-β-galactosidase (Promega) by digestion with HindIII and BamHI and inserted into the HindIII and Bam HI polylinker sites of pMT-CB6+. The final recombinant vector (recombinant vector 1) will contain the LacZ gene driven by the GFAP promoter. Its composition will be ascertained by restriction enzyme analysis and nucleic acid sequencing.

A vector containing an antisense sequence to the dominant calmodulin transcripts in U-87 MG cells, under the control of the human GFAP promoter, will be constructed using standard molecular cloning methodology as follows. The antisense vector described in the Methods section will be used. The recombinant pCR3 vector (Invitrogen), which contains the antisense sequence to the dominant calmodulin antisense transcript in U 87 MG cells, will be the source of the antisense sequence. The antisense sequence will be excised using appropriate restriction enzymes. It will then be subcloned into the polylinker site of pMT-CB6+. Finally, the GFAP promoter described for the construction of the reporter vector will replace the metallothionein promoter. The success of the subcloning procedures will be confirmed by nucleic acid sequencing and restriction enzyme analysis.

Transfection of cell lines with the expression vector

Transfections of the glioblastoma cell lines with the calmodulin antisense constructs will be performed using lipofectin (Gibco BRL) as described for PC12 cells in Examples I and II. β-galactosidase expression will be detected as previously described. The controls for endogenous β-galactosidase activity will be derived from cells not transfected with the LacZ plasmid.

The promoter activity will be determined in extracts from transfected cells using a spectrophotometric β-galactosidase assay and the substrate ONPG (o-nitrophenyl- β-D-galactopyranoside) and a kit from Promega. Since previous studies have shown that the activity of the GFAP promoter increases with the increase in cell density[130], the cells will be transfected at approximately 80–90% confluency.

Inoculation of nude mice with human glioma cells followed by administration of antibody-lipid-plasmid conjugates Transplantation of the human glioma cell line U-87 MG into mouse brain will be performed as described by Yagi et al.[114]. Briefly, six-week-old female nude mice (BALB/c-nu/nu) will be anesthetized by intraperitoneal injection of Nembutal. A 2 μl aliquot of U-87 MG cell suspension will be injected stereotactically into the corpus striatum. In preliminary studies, the survival times of mice injected with varying amounts of tumor cells ($1 \times 10^5$ cells, $3.3 \times 10^5$ cells, $1 \times 10^6$ cells in DMEM per mouse), will be assessed to determine the number of cells which results in a 30 day survival time in 50% of the inoculated mice. To examine the effects of the calmodulin antisense expression vectors, seven days after the intrastriatal transplantation of the glioma cells, the monoclonal antibody-liposome-plasmid LacZ or calmodulin antisense) will be injected into the striatum. Control animals will be injected with the same plasmid but lacking the calmodulin antisense-generating DNA sequence.

Evaluation of anti-tumor effects in vivo

Tumor growth will be assessed as follows. The mice will be weighed daily after the injection of tumor cells. At various times after the injection (up to 60 days), the experiments will be terminated and the tissues preserved by intracardial perfusion with 4% paraformaldehyde. At necropsy, the body and tumor weights will be recorded, and the size of the excised tumors will be ascertained by macroscopic observation (followed by histological analysis of hematoxylin and eosin-stained sections). The excised tumors will be prepared for β-galactosidase histochemistry (animals injected with a reporter vector) or fixed in 10% neutral-buffered formalin, embedded in paraffin, and prepared for routine histological staining (hematoxylin and eosin). The anti-tumor response will be determined by an increase in the survival rate and a decrease in the tumor size of the mice receiving the calmodulin antisense vector in comparison with that of tumor-bearing mice receiving the various controls (empty or promoterless vector, monoclonal antibody liposomes without a vector) or no therapy. The tumor sizes will be quantitated from photographs of the brain histological sections using the DUMAS image analyzer The calmodulin constructs of the present invention may also be used to advantage for the treatment of breast cancer. Preparation of expression vectors with the c-erbB2 promoter.

This promoter has been chosen as it has been demonstrated that the c-erbB2 gene product is overexpressed in certain types of breast cancer with poor prognosis.

The construction of the reporter and calmodulin expression vectors will be performed using standard molecular cloning techniques[135].

a) Generation of a β-galactosidase reporter vector. The c-erb B2 promoter will be amplified by PCR from human MBL100 genomic DNA[154]. The 1067 bp promoter sequence will be inserted by PCR cloning in the vector pCR3 (Invitrogen), and the resulting recombinant vector (recombinant vector 1) will be sequenced to confirm the correct nucleic acid sequence orientation. Subsequently, this vector will be used to generate expression vectors (reporter β-galactosidase and calmodulin antisense vectors) according to standard molecular cloning procedures[135]. The general outline of the cloning procedure for the reporter vector is as follows. The c-erbB2 promoter (from recombinant vector 1) will be subcloned into a pSV-β-galactosidase reporter plasmid vector (Promega) containing the E. coli β-galactosidase (LacZ) gene under the control of SV40 promoter/enhancer elements. The SV40 promoter/enhancer elements of pSV-β-galatosidase will be excised using the restriction enzymes EcoRI and HindIII, followed by insertion of the c-erb B2 promoter (excised from recombinant vector 1 using appropriate restriction enzymes). The structure of the constructed plasmid (recombinant vector 2) will be ascertained by restriction enzyme analysis and nucleic acid sequencing.

b) Generation of vectors expressing calmodulin antisense RNA sequences. Vectors containing RNA sequences antisense to the transcripts from the three individual calmodulin genes, placed under the control of the c-erb B2 promoter, will be constructed as follows. The calmodulin antisense vectors will be obtained by PCR cloning as previously described. These vectors express the individual antisense sequences under the control of human cytomegalovirus (CMV) promoter. The CMV promoter from these vectors will be excised using appropriate restriction enzymes. The recombinant pCR3 vector that was described earlier (recombinant vector 1) will be the source of the c-erbB2 promoter. The c-erbB2 promoter will be excised from this vector using appropriate restriction enzymes and inserted in the correct orientation into the vectors carrying the individual calmodulin antisense sequences (recombinant vector 3). The success of subcloning procedure will be confirmed by nucleic acid sequencing and restriction enzyme analysis.

c) Determination of the activity of the reporter vector using a β-galactosidase reporter assay. The promoter activity will be determined in extracts from transfected cells using a spectrophotometric β-galactosidase assay and the substrate ONPG (0-nitrophenyl-β-galactopyranoside) in a kit from Promega.

Assessment of cell differentiation

Two histological methods will be used to evaluate the induction of differentiation of human breast cancer cells. These include both morphological evaluation and immunocytochemical staining for the expression of the differentiation marker, human milk fat globule antigen (HMFG). MCF7 cells are a suitable model to study the differentiation induced by the calmodulin antisense compounds, as these cells differentiate in response to stimulation with other agents, such as 12-0-tetradecanoylphorbol-13-acetate (TPA)[148].

Transfected cells will be observed by light microscopy and the differentiation will be judged by the acquisition of characteristics typical of the mature phenotype. In particular, changes of cell volume, the cytoplasmic and nuclear morphology, and increased synthesis of milk components (increased lipid content is typical for the more differentiated state)[143,148] will be assessed. Treated and untreated cells will be plated onto multi-chamber slides (NUNC) and fixed for 30 minutes at room temperature in PBS, pH 7.4, containing 3% paraformaldehyde (PFA). The differentiation of breast tumor cells is characterized by an increase in the expression of human milk fat globule antigens [132,148,182]. The expression of a human milk fat globule antigen will be determined in an immunoperoxidase assay using primary mouse monoclonal antibody NCL-HMFG1 (Novacastra Laboratories). Immunocytochemistry will be performed on fixed cells using a DAKO immunoperoxidase detection system, which utilizes a biotinylated secondary antibody, a streptavidinbiotin-peroxidase complex, and the substrate 3,3'-diaminobenzidine, according to the manufacturer's instructions. The cell samples will be mounted using GelMount medium for immunocytochemistry (Biomeda Corporation) and will be observed with a Leitz Diaplan microscope. The specificity of the staining will be demonstrated by using controls in which the primary or secondary antibodies are omitted, and a control in which the primary antibody is substituted with normal mouse serum.

Inoculation of breast cancer cells into nude mice.

Four- to eight-week-old female nude mice (BALB/c-nu/nu) will be anesthetized with pentobarbital. SKBr3 cells ($5 \times 10^6$ in 0.05 ml culture medium) will be injected into on of the intramammary fat pads, as described previously[171].

EXAMPLE 1

Establishment and characterization of stable PC12 transfectants containing calmodulin antisense or calmodulin sense RNA.

To determine the effects of altering calmodulin levels on the growth and differentiation of PC12 cells, cultures were stably transfected with calmodulin antisense and calmodulin sense constructs. In order to control for nonspecific effects of the expression vector, cells were also transfected with control vector (vector without insert). Cells transfected with the calmodulin antisense and calmodulin sense constructs evidenced marked differences in the number of colonies and in the time at which the Geneticin-resistant colonies formed. Stable colonies from the cells transfected with control vector or with calmodulin sense vector appeared approximately 12–14 days after the start of Geneticin selection, whereas calmodulin antisense colonies began to appear after 27–30 days. The antisense transfected colonies were smaller in size and significantly fewer in number than the colonies from cells transfected with control vector or calmodulin sense construct (FIG. 2, and Table I). The cells from the calmodulin antisense colonies also had a distinct morphology (discussed below).

TABLE I

Effect of Transfecting PC12 Cells with Calmodulin Sense and Calmodulin Antisense Containing Plasmids on the Number of Geneticin-Resistant Colonies

| Control Vector | Calmodulin Sense Vector | Calmodulin Anti-Sense Vector |
|---|---|---|
| 133 ± 4 | 138 ± 15 | 16 ± 4 |

Because the differences in the number of antibiotic-resistant colonies could be due to differences in the uptake of the various expression vectors, the efficiency of uptake of the vectors was estimated by cotransfecting them with a β-galactosidase reporter plasmid and then assaying for β-galactosidase activity with a histochemical assay. The efficiencies by which the different vectors were taken up, expressed as the percentage of cells positive for β-galactosidase, were as follows: control, 43±2%; sense, 41±2%; and antisense, 43±2%. Thus the differences in the number of the resulting stable colonies were not due to differences in the uptake of the different vectors.

These studies utilized an expression vector with a $Zn^{2+}$-inducible metallothionein promoter in order to permit conditional induction of the calmodulin antisense and calmodulin sense genes that were stably transfected into the PC12 cells. Treatment of the antisense transfected clones with 80 μM $Zn_2SO_4$, a concentration which was nontoxic to control PC12 cells (data not shown), but which is reported to strongly induce the metallothionein promoter[73], resulted in the death of virtually all of the cells in the culture within 24–48 hours. Therefore, the subsequent assays of cell number, neurite outgrowth and calmodulin levels in the calmodulin antisense transfected clones were performed without $Zn^{2+}$ induction.

Nineteen stable clones were obtained after transfection with the calmodulin sense vector. Sixteen clones were obtained with the calmodulin antisense vector. Two representative clones from each of the cultures stably transfected with the control vector, calmodulin sense or calmodulin antisense constructs were selected for detailed characterization.

Changes in calmodulin levels in the calmodulin antisense and calmodulin sense transfectants.

Due to the limited yield of stable colonies and the slow growth of the cells transfected with the calmodulin antisense clones, the effect of transfecting the various constructs on the levels of calmodulin was assayed by indirect immunofluorescence. The immunostaining for calmodulin in the clones stably transfected with the calmodulin sense gene was found in the cytoplasm and the nucleus (data not shown). The average immunofluorescent signal for calmodulin in these calmodulin sense transfectants was significantly higher than that of clones containing control vector or that of parental PC12 cells (Table II). The immunofluorescent staining for calmodulin in the clones stably transfected with the calmodulin antisense sequence was localized predominantly in the cytoplasm and the neurites; a very weak signal was detected in the nucleus. A quantitative analysis of the signal intensities showed that there were significantly lower average intracellular levels of calmodulin in the calmodulin antisense transfectants than in the parental PC12 cells or in cells transfected with the cloning vector or the calmodulin sense sequence (Table II).

TABLE II

Quantitative Analysis of the Calmodulin Levels in PC12 Cells Transfected with Calmodulin Sense and Antisense Containing Vectors*

| Cell Sample | CaM/Unit Cell Area (OD Value) | Total CaM/Cell (OD Value) |
|---|---|---|
| Parental PC12 Cells | 0.26 ± 0.01 | 79 ± 2 |
| Control Vector in PC12 Cells | 0.28 ± 0.01 | 79 ± 2 |
| CaM Sense Vector in PC12 Cells | 0.45 ± 0.05[#] | 255 ± 12[#] |
| CaM Anti-Sense Vector in PC12 Cells | 0.12 ± 0.02[#] | 64 ± 2 |

*The calmodulin (CaM) levels in individual cells were determined from PC12 cells transfected with control vector or with the CaM sense of CaM antisense vectors with an immunofluorescent assay using a primary mouse anti-CaM monoclonal antibody and a secondary rabbit anti-mouse FITC antibody according to the procedure described in the Methods. Photographs of the immunofluorescently stained samples were made on black and white negative film and were subsequently used to quantify the levels of CaM using the Drexel University Image Analysis System. A series of ISO transmission density standards (Kodak) were used to generate a calibration curve of optical density (OD) value as a function of gray level, and the relative OD values were derived from calibration of the gray levels of the individual samples. The OD values for all samples were in the linear range of the calibration curve. A total of 180 cells obtained from two different stable lines from each construct were assayed The results are presented as the means ± SEM. Analysis of variance was performed with a one-way ANOVA, followed by pairwise multiple comparisons using the Student-Newman-Keuls test.
[#]$p < 0.01$ compared with the corresponding values from parental PC12 cells or PC12 cells stably transfected with the control expression vector.

* The calmodulin (CaM) levels in individual cells were determined from PC12 cells transfected with control vector or with the CaM sense or CaM antisense vectors with an immunofluorescent assay using a primary mouse anti-CaM monoclonal antibody and a secondary rabbit anti-mouse FITC antibody according to the procedure described in the Methods. Photographs of the immunofluorescently stained samples were made on black and white negative film and were subsequently used to quantify the levels of CaM using the Drexel University Image Analysis System. A series of ISO transmission density standards (Kodak) were used to generate a calibration curve of optical density (OD) value as a function of gray level, and the relative OD values were derived from calibration of the gray levels of the individual samples. The OD values for all samples were in the linear range of the calibration curve. A total of 180 cells obtained from two different stable lines from each construct were assayed The results are presented as the means ±SEM. Analysis of variance was performed with a one-way ANOVA, followed by pairwise multiple comparisons using the Student-Newman-Keuls test.
$p<0.01$ compared with the corresponding values from parental PC12 cells or PC12 cells stably transfected with the control expression vector.

Since the cells stably transfected with calmodulin antisense sequences were larger than the untransfected PC12 cells or the cells transfected with the calmodulin sense gene, the question arose as to whether the calmodulin antisense transfectants had lower signal intensities because of a redistribution of calmodulin throughout a larger cell area. Accordingly, the calmodulin levels per total cell area were calculated. The results of this analysis showed that the levels of calmodulin per total cell area in the stable sense transfectants were significantly higher ($p<0.05$) than those of parental PC12 cells or cells transfected with control vector, whereas the levels of calmodulin per total cell area in the stable antisense transfectants were significantly lower ($p<0.05$) than those of the control cells (Table II). These data showed that the transfection with calmodulin sense vector caused an increase, whereas transfection with the calmodulin antisense expression vector caused a decrease, in the levels of calmodulin. These changes were apparent both when the total amount of calmodulin per PC12 cell was assessed or when the levels of calmodulin per unit cell area were determined.

Changes in calmodulin mRNA Levels in the calmodulin sense transfectants.

Figure 3A:
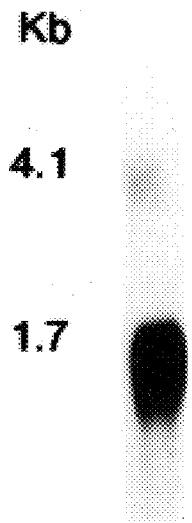
FIGS. 3A–3B: Effect of transfection with a calmodulin gene I expression vector on the levels of calmodulin gene I mRNA in PC12 cells.

FIG. 3 shows that the effect of transfection of PC12 cells with the calmodulin gene I expression vector on the levels of calmodulin were paralleled by changes in the levels of calmodulin gene I mRNA, as determined by slot-blot analysis, using a calmodulin gene I digoxigenin-labeled oligonucleotide probe. The specificity of this probe was ascertained by both Northern and slot-blot analyses. A Northern blot analysis (FIG. 3A) shows that hybridization of total cellular RNA with the calmodulin gene I oligonucleotide probe (25 pmol/ml) gave rise to two distinct bands, corresponding to the 1.7 and 4.1 kb calmodulin gene I transcripts found in PC12 cells[4]. In a slot-blot analysis, the hybridization signal was eliminated when total cellular RNA from untransfected PC12 cells was hybridized simultaneously with the digoxigenin-labeled calmodulin gene I oligonucleotide probe (25 pmol/ml) and 100-fold excess of unlabeled calmodulin gene I probe but was not abolished when the samples were incubated with a digoxigenin-labeled calmodulin gene I oligonucleotide probe in the presence of 100-fold excess of unlabeled calmodulin gene II oligonucleotide (data not shown).

Figure 3B:
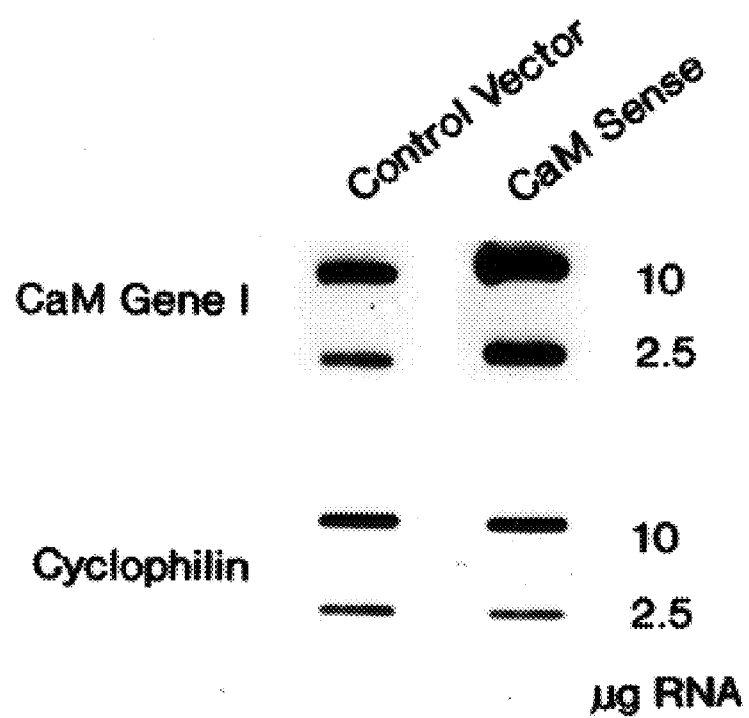

FIG. 3B, the results of a slot-blot analysis, demonstrate that the transfection of PC12 cells with the calmodulin gene I expression vector increased the levels of calmodulin gene I mRNA, whereas the level of cyclophilin mRNA, included as a control, was unaltered in the calmodulin sense transfectants. Densitometric analysis of the autoradiograms using DUMAS showed that the relative amount of calmodulin gene I mRNA in the calmodulin sense transfectants was 4.7±0.8 (mean ±SEM; n=3) times that found in the control vector transfected cells, when the values were normalized to the respective cyclophilin mRNA signals.

Altered expression of calmodulin changes the rate of proliferation of PC12 cells.

Figure 4:
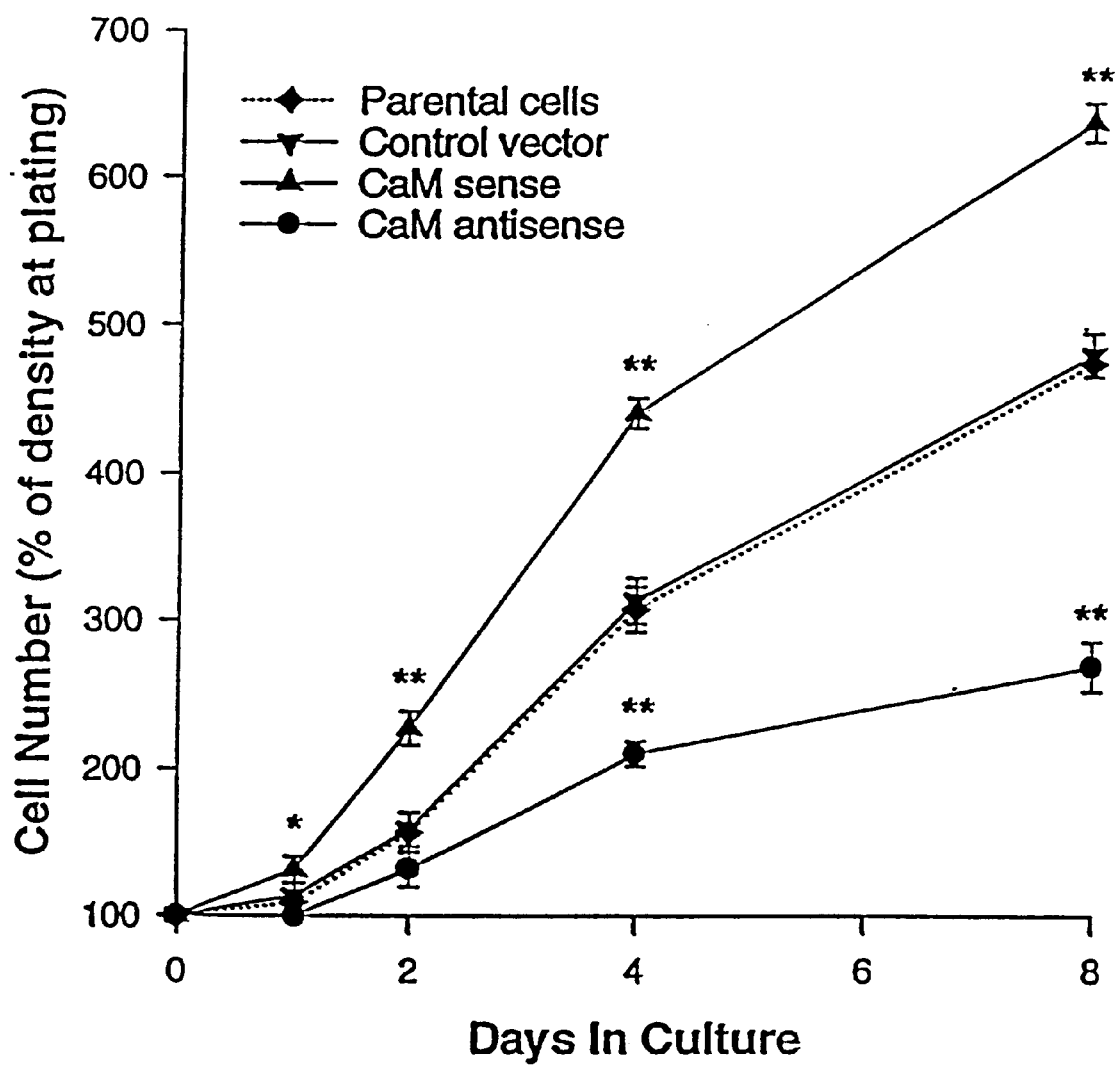
FIG. 4: Effect of overexpression and underexpression of calmodulin on the growth of PC12 cells. Untransfected parental PC12 cells and cells transfected with control vector, the calmodulin gene I sense or antisense constructs were plated (5×10$^4$ cells/cm$^2$) onto collagen-coated 24-well plates at day 0. The cell numbers were determined by direct counting at days 1, 2, 4 and 8. The data presented are the mean values±SEM from three experiments with two independent clones from each construct. *p<0.05; **p<0.01 compared with the values obtained from parental cells or cells transfected with control vector at the corresponding time points.

The marked differences in the sizes of the stable colonies obtained after transfection with calmodulin sense and calmodulin antisense-containing vectors indicated that the rates of proliferation of the PC12 transfectants were different. To quantify the proliferation rates of the different transfectants, the growth of subcultured clones was assessed by direct cell counting. FIG. 4 shows that the rates at which the calmodulin sense transfectants proliferated were significantly higher than those of the parental PC12 cells or control vector transfected cells. Conversely, the rates of proliferation of the calmodulin antisense transfectants were significantly lower than the values obtained for cells containing control vector or for those of calmodulin sense transfectants. The differences in cell proliferation were not due to nonspecific effects of the cloning vector, because the numbers of cells found at each time point for cells transfected with control vector were not significantly different from that of parental PC12 cells.

Expression of calmodulin antisense RNA alters PC12 cell morphology.

PC12 cells carrying the calmodulin antisense full-length construct not only showed a reduced rate of proliferation when compared with that of cells transfected with the calmodulin sense vector or control vector, but also acquired a distinct morphology (FIG. 2D). In 14 of the 16 colonies, the cells transfected with the calmodulin antisense vector were larger and more polygonally shaped, and nearly all of the cells (>90%) extended neuritic processes. The outgrowth of neurites, which was evident early in the period in which the colonies were forming during the selection process, was not due to nonspecific effects of the vector, because extensive outgrowth was not evident in any of the colonies giving rise to the stable cell lines containing the control vector (FIG. 2B) or the calmodulin sense vector (FIG. 2C). The neurite outgrowth was also not a result of the selection of an unique subpopulation of PC12 cells, because none of the stable cell lines obtained on transfection with control vector displayed neurite outgrowth. The cells in 2 of the 16 calmodulin antisense stable colonies were flat and closely apposed to each other, giving the impression of multinucleated cells (data not shown). The stable calmodulin sense transfectants were morphologically similar to the parental PC12 and control vector-bearing cells.

Figure 5:
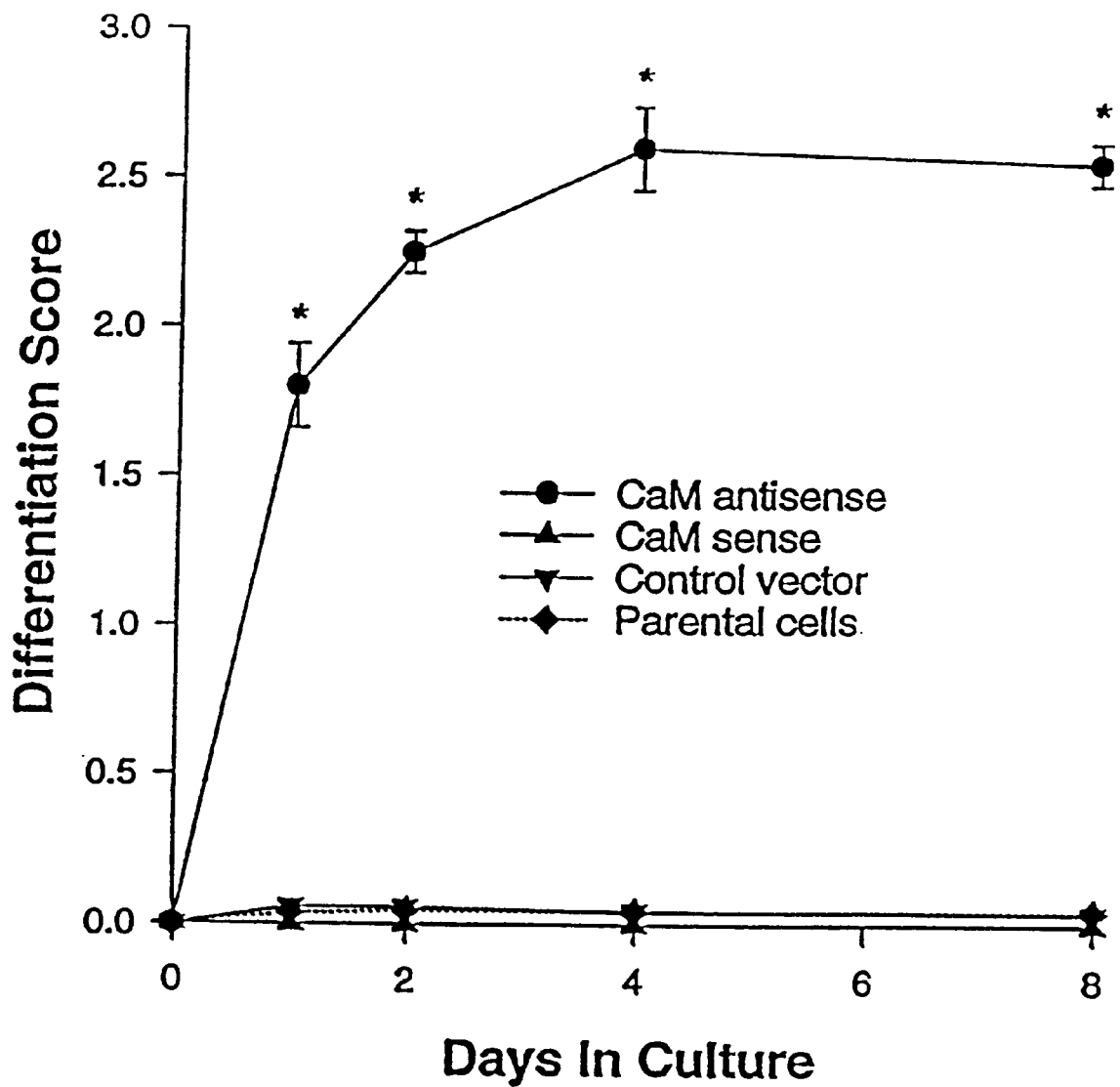
FIG. 5: Quantitative analysis of neurite regeneration from PC12 cells transfected with a calmodulin antisense vector.

To quantify the spontaneous neurite outgrowth, the transfected clones were replated in order to remove pre-existing neuritic processes, and the outgrowth of regenerated neurites was determined. The results are illustrated in FIG. 5. Parental PC12 cells, control vector and calmodulin sense transfected cells evidenced little if any neurite outgrowth. By contrast, the stable antisense transfectants regenerated neurites within one day of replating, with the extent of outgrowth reaching a plateau differentiation score of 2.5 by day four. The calmodulin sense transfectants did not show any significant degree of differentiation.

Expression of calmodulin sense RNA alters the response of PC12 cells to differentiation with nerve growth factor Addition of NGF to PC12 cells inhibits their rate of proliferation and induces characteristic changes in the cell morphology, marked by neurite outgrowth. In these experiments we determined whether altered levels of calmodulin in PC12 cell transfectants change their response to NGF. The parental PC12 cells and cells transfected with control vector displayed a marked inhibition of cell growth after treatment with NGF. By contrast, the cells stably expressing the calmodulin sense RNA continued to proliferate in the presence of NGF at significantly higher rates than parental PC12 cells or cells transfected with control vector. Furthermore, the cell numbers scored for the stable calmodulin sense transfectants after 4 and 8 days in culture in the presence of 50 nM NGF were not significantly different from the cell numbers of NGF-untreated stable calmodulin sense transfectants (FIG. 6).

The expression of the calmodulin sense RNA also resulted in a diminished ability of the PC12 cells to extend neuritic processes in response to treatment with NGF (FIG. 7). After 1 and 2 days of NGF treatment, the cells stably transfected with the calmodulin sense construct exhibited outgrowth of neurites which was similar to that of parental PC12 cells or cells stably transfected with the control vector (FIG. 7). However, by 8 days of culture in the presence of NGF, the neurites formed by the cells stably transfected with the sense calmodulin vector were significantly shorter than those of parental cells or of cells transfected with control vector.

The calmodulin insert employed in example I was a full-length cDNA from the 1.7 kb calmodulin gene I transcript. Since this transcript differed only by 15–18% in nucleotide sequence in the 0.48 kb coding region when compared with the other calmodulin transcripts[49], and since previous studies have shown that complete identity between an antisense RNA and the targeted endogenous RNA sequence is not required to inhibit gene function[25,33], it would be anticipated that in addition to the 1.7 kb calmodulin mRNA, the function of the other four calmodulin transcripts might also have been reduced, yielding a substantial decrease in calmodulin levels. To define more precisely the relative roles the individual calmodulin mRNAs play in the growth and differentiation of PC12 cells, experimental studies on the effects of antisense encoding oligomers targeted to the 5' untranslated regions, where marked differences in the nucleotide sequences of the various calmodulin mRNAs are found, were performed as described in example II.

One curious finding in the present study was the markedly (approximately 9-fold) fewer number of colonies resulting from the transfection with the calmodulin antisense sequence when compared to control vector or to calmodulin sense transfection. The assays described above illustrate that the differences in the number of colonies were not due to differences in the cellular uptake of the sense and antisense vector constructs, and also could not be due to differences in cellular proliferation (which were reflected in the sizes of the colonies), the possibility arose that the reduced levels of calmodulin in the cells transfected with the calmodulin antisense vector led to cell death. This possibility is supported by the finding that enhanced induction of the calmodulin antisense by the addition of $Zn^{2+}$ resulted in the death of all of the calmodulin antisense transfectants. Calcium-activated cleavage of nuclear DNA by endonucleases has been postulated to play a role in the programmed cell death (apoptosis) of neurons and PC12 cells[39,46], and as calmodulin is the major mediator of calcium-regulated processes in many cell types, lowering the levels of calmodulin may trigger apoptosis in PC12 cells.

In addition to having a greater rate of proliferation, PC12 cells transfected with the calmodulin sense gene also showed a reduced response to NGF. NGF-unresponsive PC12 cell subclones and subclones which continue to proliferate and form neurites in the presence of NGF have been reported[22]. It is unlikely that these experiments selected for such subclones, because upon NGF treatment, the rates of proliferation of cells transfected with the control vector were inhibited, and the cells extended long neurites. Furthermore, the calmodulin sense transfectants did display neurite outgrowth in response to NGF, albeit at a reduced level, equivalent to that observed with the control cells by day 2 of NGF treatment. One possible explanation for the unusual response of the stable sense transfectants to NGF is that abnormally high levels of calmodulin interfere with microtubule assembly during neurite formation[14,25,38,71]. As noted previously, this effect of calmodulin on the cytoskeleton could be mediated by the action of calmodulin-dependant protein kinase II on cytoskeletal proteins, namely tubulin, vimentin, and the microtubule-associated proteins MAP-2 and tau[55].

This apparent reciprocal relationship between cell proliferation and differentiation, which is the result of crosstalk or overlap between the regulatory signal transduction pathways[16a], may explain why PC12 cells stably transfected with the calmodulin sense vector exhibited a reduced response to NGF in extending neuritic processes. Whether this was a direct effect of increased calmodulin levels on the differentiation process or was an effect secondary to the effect of increased calmodulin levels on cell proliferation is not known.

EXAMPLE II

Oligodeoxynucleotides antisense to calmodulin mRNAs inhibit the proliferation of PC12 cells.

As previously noted, calmodulin is involved in numerous biological processes, including regulation of the cell cycle and cell differentiation. Although all of the calmodulin genes expressed in PC12 cells are highly homologous to one another (and to calmodulin genes of other species) earlier studies have demonstrated that the three genes are differentially localized in the cell and are expressed at different stages of the cell cycle[3,4]. Additional studies indicate that neurite outgrowth in PC12 cells was associated with increased levels of calmodulin and certain calmodulin mRNAs. Our recent immunocytochemical and in situ hybridization analyses have demonstrated that calmodulin and the calmodulin mRNAs are present not only in cell bodies but also in neurites of PC12 cells differentiated with NGF[74]. In order to address the roles of the three different calmodulin genes in PC12 cells, effects of antisense phosphorothioate oligodeoxyribonucleotides (oligomers) targeted to the initiation sites of calmodulin mRNAs transcribed from the three calmodulin genes were investigated. The 20-mers were designed according to the published sequences of the three genes and are set forth below in Sequence I.D. Nos. 1–10.

```
CalmodulinGeneImRNAantisense20-mers
Sequence I.D. No. 1:  (-8 to +12)   5'-CTGATCAGCCATGGTGCGAG-3';

Sequence I.D. No. 2:  (-18 to +2)   5'-ATGGTGCGAGCGAAGGAAGG-3';

CalmodulinGeneIImRNAantisense20-mers
Sequence I.D. No. 3:  (-8 to +12)   5'-TTGGTCAGCCATGCTGCAAG-3';

Sequence I.D. No. 4:  (-15 to +5)   5'-GCCATGCTGCAAGGGCTACC-3';

CalmodulinGeneIIImRNAantisense20-mers
Sequence I.D. No. 5:  (-8 to +12)   5'-CTGGTCAGCCATGGCGAGGC-3';
Sequence I.D. No. 6:  (-15 to +5)   5'-GCCATGGCGAGGCACGTATC-3';

RandomOligonucleotideSequence20-mers
Sequence I.D. No. 7:                5'-GCCGAATTCCATGAGGCTTA-3';

Sequence I.D. No. 8:  (CaM I):      5'-GCAAGGACAGGGAGGGTTAG-3';

Sequence I.D. No. 9:  (CaM II):     5'-CTCTATCACGGGAGCACCGG-3';

Sequence I.D. No. 10 (CaM III):     5'-GACAGGCGAGTCCAGTCGTC-3'.
```

Uptake of the oligos was assessed by incubating PC12 cells with a FITC-labeled oligo antisense to calmodulin gene I mRNA. Confocal microscopy revealed that the FITC-labeled oligonucleotide was taken up into the cytoplasm and nuclei (data not shown). The addition of all three oligos antisense to the mRNAs encoded by the three calmodulin genes inhibited the proliferation of PC12 cells relative to vehicle (DMEM) only (FIG. 8). FIG. 9 demonstrates that this inhibition of proliferation was due to the specific sequence of nucleotides in the calmodulin antisense oligomers. Calmodulin antisense oligos significantly inhibited the proliferation of PC12 cells on days 6 and 8. The random calmodulin oligomer did not have any obvious effect on the proliferation of cells before day 6; however, on day 8 a slight inhibition of the proliferation of PC12 cells was observed. In the figure, each point represents the mean value from quadruplicate samples. The data were analyzed by a two-way ANOVA.

Applying the three oligomers antisense to calmodulin genes I, II and III in combination produced a dose-dependent inhibition of the proliferation of the PC12 cells (FIG. 10). To more accurately assess the roles each of the calmodulin genes were playing in the inhibition of PC12 cell proliferation, antisense oligomers were synthesized that hybridize to the translation initiation sites of each of the three individual calmodulin genes. In FIG. 11, A, B, C, each point represents the mean value from quadruplicate samples. The data were analyzed by a two-way ANOVA. Calmodulin gene I, (FIG. 11 A) and calmodulin gene II (FIG. 11 B) antisense oligomers significantly inhibited the proliferation of PC12 cells on day 4 compared with the values for the corresponding random oligodeoxynucleotides, while there was no significant difference in the inhibition of the proliferation of PC12 cells between the calmodulin gene III antisense and its corresponding random oligomer (FIG. 11 C & Table III).

TABLE III

Effect of Individual Calmodulin Gene Antisense Oligodeoxynucleotides on the Proliferation of PC12 Cells $IC_{50}$ ($\mu$M)

| Treatment     | CaM Gene I | CaM Gene II | CaM Gene III |
|---------------|------------|-------------|--------------|
| Antisense     | 4.1*       | 4.7*        | 8.2          |
| Random Oligo  | 15.7       | 14.3        | 10.3         |

*$p < 0.05$ compared with values from corresponding random oligomers.

Levels of calmodulin in hippocampal cells in culture

Figure 12A:
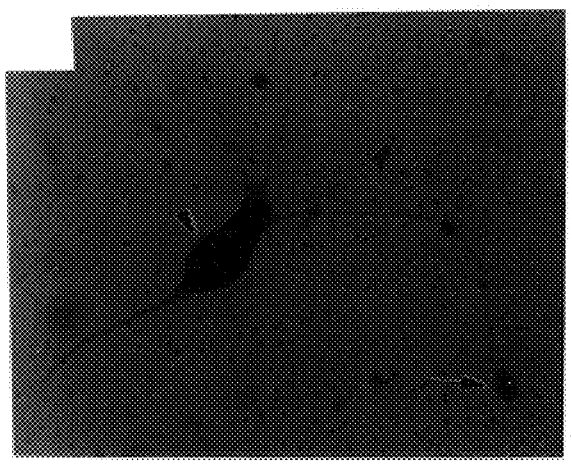
Figure 12B:
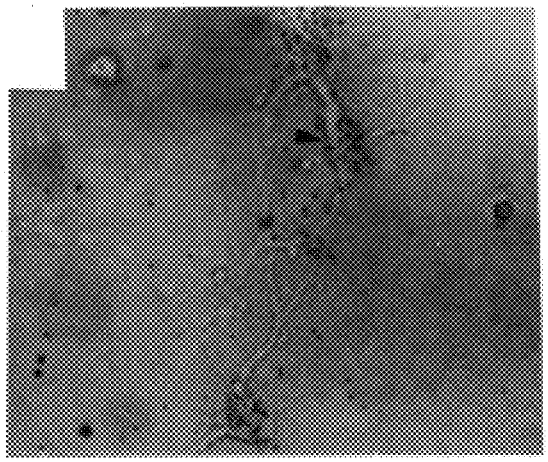
Figure 12C:
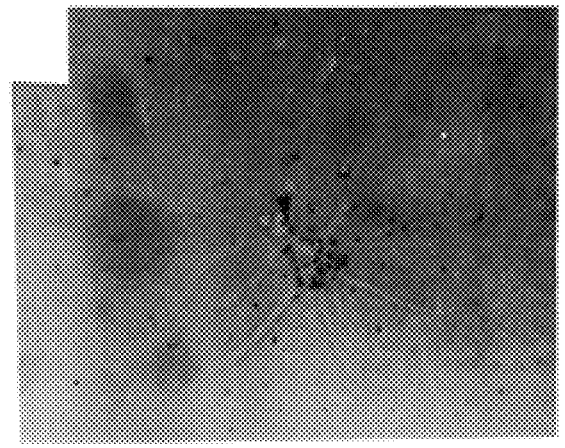
Figure 12D:
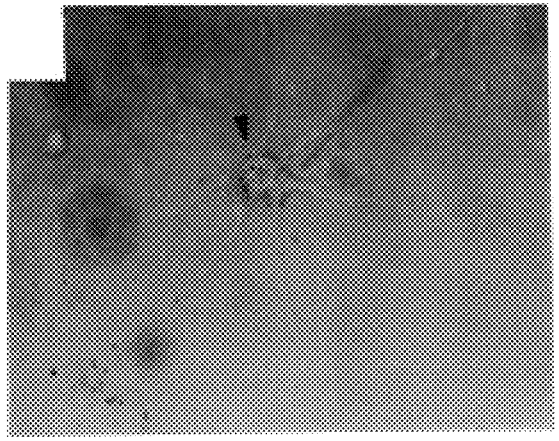

To determine the extent to which the findings on the role of calmodulin in PC12 cells apply to primary neuronal cells, the following experiments were performed. Using immunoperoxidase cytochemistry, it has been demonstrated that, similar to the localization of calmodulin in PC12 cells, calmodulin is abundantly localized both in the cell bodies and the neurites of primary cultures of hippocampal cells (FIG. 12a). Calmodulin was also found in varicosity-like structures and growth cones. In situ hybridization histochemistry, demonstrated that the transcripts for calmodulin were expressed at varying degrees, the most abundant being the transcripts derived from calmodulin genes I and II (compare FIGS. 12B, 12C and 12D). Two possible explanations may account for this apparently different distribution of the calmodulin transcripts between PC12 cells and hippocampal neurons. Either the levels of the calmodulin transcripts in the neurites of hippocampal cells are well below the detection limits of the in situ hybridization assay, or alternatively, calmodulin is synthesized in the cell bodies and transported to the neurites.

Conclusion

Specific alterations of the levels of calmodulin in PC12 cells have been produced by means of calmodulin antisense and calmodulin sense-expressing vectors. These alterations affected the proliferation and differentiation of stably transfected cells. Higher levels of calmodulin caused an increase in the proliferation of PC12 cells and a reduction in NGF-induced neurite outgrowth, whereas lower levels resulted in a decreased cellular proliferation and the appearance of morphological differentiation. Thus calmodulin plays a key role in cellular division and differentiation. An important issue that arises from this study is the possible relationship between cellular proliferation and differentiation, particularly as they relate to the properties of neoplastically transformed cells. Prominent features of transformed cells are the capacity for unlimited growth in vitro and dedifferentiation. It has been previously shown that many transformed and tumor cells express elevated levels of calmodulin when compared with normal cells and tissues[12,32,66,69]. For example, immunocytochemical and biochemical studies on cultured C6 glioma cells have suggested that differentiation of glioma cells is accompanied by a decrease in calmodulin levels[30]. Similarly, differentiation of mouse myoblast BC3H1 cells is accompanied by decreased levels of all of the calmodulin transcripts[10]. Furthermore, calmodulin antagonists have been shown to induce the expression of normal differentiation markers in HL-60 human promyelocytic cells[67]. However, calmodulin antagonists have numerous non-specific actions as they interact with targets other than calmodulin[61]. As set forth in the following examples, the calmodulin antisense constructs described herein may be used to suppress proliferation and induce differentiation in tumor-derived cells by reducing the levels of calmodulin. This approach would be especially suitable for neoplastic hematopoietic cells which can be genetically manipulated ex vivo.

Finally, the availability of antisense oligonucleotide vectors to each of the three calmodulin genes expressed in PC12 cells facilitates the elucidation of the precise morphological control mechanisms mediated by differential expression of calmodulin in the proliferation and differentiation of neuronal cells.

EXAMPLE III

Use of calmodulin antisense oligonucleotides and vectors in neoplastic glial cells Gliomas are one the most therapeutically challenging tumors of the brain[86]. The calmodulin antisense constructs of the present invention may be used to advantage in the treatment of gliomas. The glioma group of primary brain tumors is complex with the astrocytic variants of gliomas (comprising astrocytoma, anaplastic astrocytoma, and glioblastoma) being the most common group of these tumors in adults[87]. Malignant gliomas comprise 65% of all primary brain tumors and affect 15,000 to 17,000 Americans every year[88]. At the time of diagnosis, most of these tumors are glioblastomas (astrocytoma grade IV) or anaplastic astrocytomas (astrocytoma grade III)[89]. Despite aggressive surgical, chemo- and radiotherapy, the prognosis for patients with either tumor remains poor. Median survival of patients with glioblastomas is 11 months and that of patients with anaplastic astrocytomas is about 3 to 5 years after diagnosis.

Because of the significant heterogeneity in the phenotype and biologic behavior of gliomas, different therapeutic approaches have been explored. Unfortunately, there are several problems associated with the current forms of treatment. These include the infiltrative patterns of these tumors which make complete surgical resection impossible, the toxicity of the chemo and radiotherapy, and the inability of many chemotherapeutic drugs to cross the blood brain barrier[84]. In an attempt to solve these problems, various immunotherapeutic, and more recently, gene therapeutic approaches have been attempted. These treatments have targeted growth factors, cytokines, oncogenes, and tumor antigens expressed on glioma cells. Each of these treatments has been shown to be at least partially effective in controlling a particular subset of gliomas[88,91–97]. Even though these studies have yielded promising results, the goal of producing effective and selective therapeutic agents for these devastating tumors has not yet been fulfilled.

Viral vectors (based on retroviruses, herpes simplex viruses or adenoviruses) have been shown to be potentially effective as vehicles for gene delivery to glioma cells[97–103]. For example, an interesting approach entails the genetic modification of glioma cells to produce the herpes simplex virus thymidine kinase (HSV-tk) gene thereby conferring cellular sensitivity to nucleotide analogues such as ganciclovir[98,100,102,104,106]. Viral vectors, however, have several disadvantages, including the danger of pathogenicity even with supposedly non-replicative viral stocks, problems arising from integration into the host genome, and difficulties in mass production of high viral titers. Some of these problems may be overcome by the use of plasmid-based vectors if efficient strategies for the delivery of plasmid vectors are devised.

The use of an antisense strategy as described in Examples I and II, to inhibit gene expression is a particularly attractive alternative approach to the inhibition of calmodulin with pharmacological compounds. Indeed, antisense oligodeoxynucleotides and antisense RNA have already been employed in vitro and in vivo in attempts to limit tumor growth in the central nervous system[91,107–108]. Application of antisense oligodeoxynucleotides to N-myc, which is expressed in tumors of neuroectodermal origin (e.g. neuroblastoma, retinoblastoma and small cell lung carcinoma), inhibited the growth and induced morphological differentiation of neuroblastoma cells and neuroectodermal cell lines[108]. Growth of transformed human astrocytes was inhibited by an antisense molecule to the basic fibroblast growth factor[91]. An antisense to the insulin-like growth factor-1 (IGF-I) using a gene transfer approach has also been employed in rat glioblastoma cells[109–111,96]. However, the targeting of these factors might lead to significant effects in normal as well as in cancer cells. The strategy proposed in this application, i.e., targeting one of the several calmodulin transcripts, provides a relatively high degree of specificity and has several advantages over conventional chemotherapy. These advantages include: 1) a high degree of target specificity[112]; 2) ligand-mediated selective delivery of the antisense compounds to tumor cells[166,114]; 3) the control of timing and degree of vector-generated antisense RNA expression using tissue-specific and inducible promoters[178]; and 4) substantially less potential for toxicity. As long-lasting expression of vectors injected into gliomas has been observed for other proteins[166,114] it is anticipated that the selective targeting of key calmodulin transcripts by introducing specific antisense-generating vectors into tumors will result in a substantial and long-lived reduction in tumor growth.

Although there is evidence showing changes in levels of calmodulin in gliomas, at present the main evidence for a role of calmodulin in the proliferation of gliomas is derived from studies using calmodulin antagonists in vitro on glioma cell lines[81,83] and in vivo on patients[150]. Pharmacological agents that reduce calmodulin activity have also been effective in inhibiting in vitro the proliferation of several other types of malignant cells, including breast and leukemic cells. Calmodulin antagonists have augmented the antiproliferative and cytotoxic effects of antineoplastic compounds[7,150,161]. In addition to the antiproliferative effects on malignant cells, drugs with anti-calmodulin activity have induced differentiation in glioma and leukemic cells[78,67] and have inhibited the attachment of human breast and melanoma cells to extracellular matrix proteins[160]. For example, in T9 glioma cells, calmodulin antagonists, besides inhibiting cell growth, induced morphological changes, including clustering of the cells, spreading of the cytoplasm, and development of lamellopodium-like protrusions[78]. Unfortunately, the currently available calmodulin antagonists display numerous non-selective effects because they interact with several intracellular targets other than calmodulin[61].

In summary, the major role calmodulin plays in cell proliferation and differentiation and the elevated levels of calmodulin in glial tumors implicate calmodulin as a suitable target for anti-tumor therapy of high-grade gliomas. The antiproliferative and differentiation-inducing effects of drugs with anti-calmodulin activity further support this observation. However, although there is no question that calmodulin plays a vital role in cell division, its very importance and ubiquitous distribution raise serious targeting issues for the safe delivery of the calmodulin constructs of the present invention. The biological machinery involved in synthesizing calmodulin is extremely complex, and this complex machinery varies with the cell type. As noted previously, calmodulin is formed by 5 distinct transcripts, which are differentially regulated and whose relative abundance varies widely among cells. By administering antisense oligodeoxynucleotides or antisense RNA directed to the specific calmodulin transcripts found in high abundance in the target cells, selective inhibition of proliferation may be obtained. By packaging the calmodulin antisense oligodeoxynucleotides or RNA expression vectors in liposomes carrying antibodies directed to cell-specific antigens on cancer cells, selective targeting may be further enhanced. Finally, by incorporating an inducible, cell type-specific promoter into the vector carrying the calmodulin antisense RNA, calmodulin antisense RNA may be selectively expressed in those target cells capable of activating the promoter. This overall strategy, therefore, provides more selective targeting and a higher degree of expression of an antiproliferative agent in certain cell types than is currently achievable with conventional pharmacotherapy.

The relative abundance of the individual calmodulin transcripts in human glioblastoma cell lines and in normal human glial cells will be determined. Based on this information, neoplastic glial cells will be treated with antisense compounds (antisense oligodeoxynucleotides or antisense RNA produced by an expression vector) targeted to the dominant calmodulin mRNA found in those cells. Following treatment, the effects of suppressing the dominant calmodulin MRNA on the rate of cellular proliferation and the degree of differentiation of the glioma cells will be assessed. Changes in cell proliferation will be evaluated by measuring cell number and the rate of incorporation of [$^3$H]-thymidine into DNA. Differentiation will be assessed by the appearance of typical morphological changes and by an increase in glial fibrillary acidic protein (GFAP). The changes in phenotype will be correlated with changes in the levels of calmodulin and the calmodulin mRNAs.

To achieve cell type specific delivery, the oligodeoxynucleotides or expression vector will be encapsulated in liposomes which in turn, will be coated with a monoclonal antibody directed to the epidermal growth factor (EGF) receptor. EGF receptor is overexpressed in high-grade gliomas when compared to normal glia. Additionally, glioma derived cell lines are available that have high and low expression of the EGF receptor. Initially, the selectivity and efficiency of delivery of the antibody-coated liposomes to glioma cells will be assessed. The nonspecific uptake of liposomes containing either fluorescently-labeled oligodeoxynucleotides or a β-galactosidase reporter gene will be compared in cell lines that have high and low expression the EGF receptor and normal glial cells, which lack the EGF receptor. Subsequently, the glioma cells will be treated with antibody-coated liposomes containing antisense oligodeoxynucleotides and antisense RNA expression vectors, both targeted to the dominant calmodulin transcript found in these cells. The biological consequences of selectively delivering the calmodulin antisense compounds to the tumor cells will be assessed by measuring their effects on cellular proliferation and degree of differentiation and on the levels of calmodulin and the calmodulin transcripts.

In order to selectively express the antisense RNA in cells of glial origin, but not in neurons, the calmodulin antisense RNA expression vector will be designed to contain a promoter sequence specifically active in glial cells, the GFAP promoter. The activity of the promoter will be assessed in GFAP-positive and GFAP-negative glioblastoma cell lines and in a GFAP-negative human cortical neuron cell line. Initially, the ability of the GFAP promoter to direct cell-type specific expression of a β-galactosidase reporter gene in glioma cells will be evaluated in cells which express GFAP in comparison to cells which do not express GFAP. Subsequently, the calmodulin antisense RNA expression vector will be engineered to contain the cell-specific GFAP promoter sequence, the effectiveness of the promoter being assessed by PCR using primers for the calmodulin antisense sequence. Cellular proliferation, differentiation, levels of calmodulin and levels of calmodulin transcripts will be determined in cells expressing calmodulin antisense constructs driven under the GFAP promoter.

The anti-tumor effects of calmodulin antisense compounds will also be assessed in vivo. These experiments are designed to selectively inhibit the calmodulin transcripts in human glioma cells in vivo. Following delivery, the biological consequences of reducing calmodulin levels in these cells will be examined. To accomplish this, human glioma cells will be xenotransplanted intracranially into nude mice. The specific calmodulin antisense oligodeoxynucleotide or RNA expression vector, identified from the studies outlined in the previous examples, will be tested for their ability to inhibit tumor growth. These phenotypic changes will be correlated with changes in the levels of calmodulin and the calmodulin transcripts.

Delivery, uptake and expression of antisense constructs is feasible. Supporting this observation are recent studies from this laboratory. A vector was prepared (pCR3, Invitrogen; this same plasmid will be used as an expression vector for the calmodulin antisense RNA sequences) containing a 322 bp cDNA sequence antisense to a portion of the $D_2$ dopamine receptor transcript. The resulting vector, pCR3 $D_2$AS, was complexed with the cationic lipid 1,2-dioleoyl-3-trimethylammonium-propane (DOTAP, Avanti Polar Lipids) and injected into the corpus striatum of mice. The control animals received injections of DOTAP alone or injections of an empty pCR3 vector complexed with DOTAP.

Six days later total cellular DNA was isolated from the injected striata and subjected to PCR with primers specific for the SP6 and T7 promoters which flank the vector polylinker. The results of these studies demonstrated the presence of a PCR product corresponding in size of the $D_2$ antisense insert plus the polylinker sequences. A PCR product, corresponding in size to the vector polylinker, was also detected in DNA from mice injected with the control empty pCR3 vector. These PCR products were not detected in the DNA samples isolated from mice injected with DOTAP alone. The identity of the PCR product corresponding to the $D_2$ antisense was confirmed by restriction analysis with SacI, which recognizes unique sites in the dopamine antisense sequence and in the polylinker. See FIG. 13.

The biological consequences and the duration of action of this $D_2$ antisense plasmid expression vector in mice was also assessed. The results showed that a single intrastriatal injection of pCR3 $D_2$AS in mice caused a statistically significant inhibition of behaviors induced by a $D_2$ dopamine agonist when compared with the values from control animals injected with the empty vector pCR3. See FIG. 14. The antisense effect lasted up to one month after the injection. This effect was specific for the $D_2$ subtype of dopamine receptors, because the $D_2$ antisense expression vector did not inhibit behavioral responses to challenge injections with a dopamine receptor agonist.

These data, illustrating that expression of a $D_2$ antisense RNA in vivo produces specific, long-term inhibition of $D_2$ receptor function, provide support for using a similar approach to express a specific calmodulin antisense RNA in vivo and inhibit the functions that calmodulin subserves.

Reduced levels of calmodulin in glioma cells inhibit the rate of cellular proliferation.

Rat C6 glioma cells were transiently transfected with the same calmodulin antisense or sense expression vectors employed in the PC12 cell studies (described in Examples I and II), and the levels of calmodulin and the calmodulin transcripts were determined. The results showed that within six hours after inducing the expression of the calmodulin antisense RNA by adding $Zn^{2+}$ there was a reduction of the 1.7 kb transcript from calmodulin gene I in the antisense transfectants compared with that of the empty vector transfected cells (compare lane f with lane c). See FIG. 15. Unlike PC12 cells, $Zn^{2+}$ induction merely reduced the proliferation rate of the glioma cells, cell death was not observed. This was paralleled by reduced levels of calmodulin (18 hours after the induction) (compare M1 with M2 in FIG. 16) and an approximately 50% inhibition of cell proliferation (determined by counting the cell numbers and estimating the doubling time using a Coulter Channelyser 956 instrument). The doubling time was 11±1 hours for the control cells and 20±2 hours for the calmodulin antisense transfectants. In the calmodulin sense transfectants, there were increased levels of calmodulin RNA, FIG. 15, and protein, FIG. 16, and approximately a 50% increase in the rate of cell proliferation (the doubling time was 7±1 hours for the calmodulin sense transfectants). These studies demonstrate that it is feasible to inhibit the proliferation of glioma cells by inhibiting the expression of calmodulin using an antisense RNA expression vector. Additional studies will use expression vectors that generate antisense RNA directed to only the dominant calmodulin transcript found in these cells.

Increased levels of calmodulin MRNA in experimental glioma tumors in rat brain

Further studies have revealed that the total levels of the calmodulin transcripts are elevated in rat C6 glioma tumor cells grown intracerebrally in Fisher rats. Glioma cells were implanted into the corpus striatum of rats, and 30 days later the brains were sectioned and subjected to in situ hybridization histochemistry using a radiolabelled probe for the calmodulin MRNA[11]. FIG. 17 shows that the total levels of the calmodulin transcripts are significantly higher in the tumor cells in comparison with the surrounding normal brain tissue or with the other striatum. Even though it is possible that the higher signal for the calmodulin mRNA in the tumor may have been due to the higher cell density, the higher abundance of the calmodulin mRNA in C6 cells, cultured in vitro, suggests that there is higher expression of calmodulin in glial tumors.

Total cellular RNA was isolated from a variety of cultured human glioblastoma cell lines, T98G, U-87 MG, U- 373 MG and U-138 MG using Trireagent. See FIG. 18. The results showed that the human glioblastoma cell line T98G expressed the 4.1 kb transcript from calmodulin gene I, the 1.4 kb transcript from calmodulin gene II and the 2.3 kb transcript from calmodulin gene III. The U-87 MG cells expressed the 1.4 kb transcript and a very faint band at 1.4 kb. U-138 cells expressed 4.1 and 1.4 kb calmodulin transcripts. These results, showing that each glioblastoma cell line expressed a characteristic pattern of calmodulin transcripts, facilitate the selective targeting of dominant calmodulin transcripts to selectively inhibit cellular proliferation.

Monoclonal antibody specific for an antigen on glioma cells.

The rationale of using a monoclonal antibody-liposome approach to selectively deliver calmodulin antisense compounds to glioma cells is based on earlier studies. A monoclonal antibody (MoAb) 425 has been obtained which is specific for a peptide epitope on the human EGF receptor. The production and binding characteristics of this antibody have been published previously[165,117,118]. MoAb 425 is suitable for selective targeting of gliomas for the following reasons. The EGF receptor is overexpressed on a subset of high grade gliomas with poor prognosis, and it has a putative role in glioma cell proliferation[119–121]. [13]I-labeled F(ab')2 fragments of this MoAb have been injected into nude mice grafted with U-87 MG glioma cells and the fragments have preferentially localized in tumor tissue compared to normal mouse tissues[122]. FIGS. 19 A–D demonstrate that MoAb 425 specifically binds to U-87 MG glioblastoma cells. A431 cells were also stained as a positive control since these cells were utilized as an antigen source for the generation of MoAb 425. In subsequent studies other glioma cell lines will be assessed for reactivity with MoAb 425. Cell lines with demonstrably high and low binding will be used to further characterize the selective delivery of MoAb 425-liposome-DNA complexes, generating calmodulin antisense RNA.

Data provided herein demonstrate that calmodulin is involved in controlling the rate of proliferation of gliomas, and that calmodulin mRNA levels are elevated in gliomas. Transfection of these cells with a calmodulin antisense-bearing vector reduced the levels of calmodulin and the calmodulin transcripts and also inhibited cell growth. To show the feasibility of administering and expressing an antisense RNA vector in vivo in brain, preliminary experiments have been described showing that specific biological effects are produced in mice following the injection of a plasmid vector containing a DNA sequence that expresses an antisense RNA to one of the dopamine receptors. In addition, selective delivery and expression of the calmodulin antisense sequences of the invention will be enhanced through the use of monoclonal antibody 425, which is specific for the human epidermal growth factor receptor which is overexpressed in high-grade gliomas. Finally, a tissue-specific promoter (GFAP) will be utilized to express the calmodulin antisense RNA specifically in glia-derived cells.

EXAMPLE IV

Treatment of breast cancer with calmodulin antisense constructs

Breast cancer is the leading form of cancer found in the United States, and the incidence of new cases has increased throughout much of the last decade[174]. In countries such as Japan, where rates are substantially lower than in the United States, there have been dramatic increases in rates in recent years; thus breast cancer is also becoming an increasingly important problem in previously low-risk countries[143,144]. Because of the high incidence of breast cancer, diverse therapeutic approaches have been developed. These include surgical, hormonal, and chemo- and radiotherapy[158,175]. However, there are major drawbacks of the conventional forms of therapy, such as toxicity of the existing radiopharmaceutical and chemotherapeutic drugs, and the lack of effective therapies for the management of metastatic breast cancer[140,164,169]. Therefore, new biological and gene therapeutic approaches are being explored[152,158]. Different antigens, enzymes, growth factors and oncogenes expressed by breast cancer cells have been targeted. While these approaches have been shown to be effective, extensive laboratory and clinical studies suggest that the most effective control of breast cancer cell growth will be achieved by combining several approaches. One particularly suitable cell regulator to target for the inhibition of breast cancer cell growth is the ubiquitous $Ca^{2+}$- binding protein calmodulin.

Pharmacological agents that reduce calmodulin activity have been effective in in vitro inhibition of the proliferation of breast[151,172], leukemic[153,163], glioma[155], and astrocytoma cells, and in vivo in patients with gliomas[155]. Calmodulin antagonists have also been effective in augmenting the antiproliferative and cytotoxic effects of antineoplastic compounds[7,150,161]. In addition to the antiproliferative effects on malignant cells, drugs with anti-calmodulin activity were found to induce differentiation in leukemic cells[67] and inhibit the attachment of human breast and melanoma cells to extracellular matrix proteins[160]. Unfortunately, these drugs display numerous non-selective effects because they interact with several intracellular targets other than calmodulin[61].

The use of an antisense strategy to inhibit gene expression is a particularly attractive alternative approach to the inhibition of calmodulin with pharmacological compounds. Indeed, antisense oligodeoxynucleotides and antisense RNA have already been employed in vitro and in vivo in attempts to limit tumor growth[139–157,168]. For example, antisense oligodeoxynucleotides to DNA polymerase α elicited an antiproliferative effect in vitro on breast cancer cells[133]. Antisense inhibition of the expression of c-myc using oligodeoxynucleotides reduced the proliferation of thyroid carcinoma cell lines[138] and induced monocytic differentiation of HL-60 leukemic cells[180]. Application of antisense oligodeoxynucleotides to N-myc, which is expressed in tumors of neuroectodermal origin (e.g. neuroblastoma, retinoblastoma and small cell lung carcinoma), inhibited the growth and induced morphologic differentiation of neuroectodermal cell lines[167]. In a number of studies, antisense oligodeoxynucleotides to the c-myb oncogene have been shown to inhibit the proliferation of malignant hematopoietic cells[134,147,177]. However, targeting early- or delayed-response genes may lead to significant effects in normal as well as in cancer cells. The strategy proposed in this application, i.e., targeting one of the several calmodulin transcripts expressed in breast cancer cells, may provide a higher degree of specificity than targeting the early-response genes, or perhaps even oncogenes, and has several advantages over conventional chemotherapy. These advantages include: 1) high degree of target specificity[167]; 2) ligand-mediated selective delivery of the antisense compounds to tumor cells[146,173]; 3) the control of the timing and degree of vector-generated antisense RNA expression using tissue-specific and inducible promoters[178]; and 4) substantially less potential for toxicity. As long-lasting expression of vectors injected into tumors has been observed for other Proteins[166,162], it is anticipated that the selective targeting of key calmodulin transcripts by introducing specific antisense vectors into tumors will result in a substantial and long-lived reduction in tumor growth.

In summary, the major role calmodulin plays in cell proliferation and differentiation and the elevated levels of calmodulin in mammary tumors suggest that calmodulin may be a suitable target for anti-tumor therapy of breast cancer. The antiproliferative and differentiation-inducing effects of drugs with anticalmodulin activity also support the premise of the present invention.

Determination of the dominant calmodulin transcript expressed by breast cancer cells will result in the identification of a suitable target for the antisense constructs of the invention. By packaging the calmodulin antisense oligodeoxynucleotides or RNA expression vectors in liposomes carrying antibodies directed to cell-specific antigens on the breast cancer cells, one may achieve further selectivity of action. Finally, by incorporating an inducible promoter that is expressed in the tumor cell into the vector carrying the calmodulin antisense RNA, selective expression of the calmodulin antisense RNA may be achieved in those target cells. This overall strategy, therefore, should provide a higher degree of selective targeting and expression of an antiproliferative agent to certain cell types than could currently be achieved with conventional pharmacotherapy. Further, information provided in this program regarding the technology of specifically increasing the uptake of antisense RNA expression vectors in breast cancer cells and of expressing certain DNA sequences specifically in these cells could also be used to selectively target and express other types of anticancer agents to breast cancer cells, such as antisense RNA directed to transcripts encoded by breast cancer-specific genes that have recently been identified[179].

The feasibility of using a monoclonal antibody-liposome approach to selectively deliver calmodulin antisense vectors or oligodeoxynucleotides to breast cancer cells is based earlier studies. Monoclonal antibodies, 15-16A and 425 to breast tumor antigens have been obtained and characterized. The production and binding profiles of these antibodies have been published previously[165].

The presence and relative abundance of the individual transcripts from calmodulin genes I, II and III has been determined in total RNA isolated from normal human breast tissue (Clontech) and from breast cancer cell lines (MCF7, SKBr3) using Northern analyses. See FIG. 20. The results show that there is a different pattern of calmodulin transcripts expressed in normal breast tissue as compared with that of in the breast cancer cell lines. The normal human breast tissue strongly expressed the 4.1 kb transcript from calmodulin gene I and the 1.4 kb transcript from calmodulin gene II. The breast adenocarcinoma cell lines (MCF7 and SkBr3) in addition to expressing the 4.1 and 1.4 kb transcripts, also expressed the 1.7 kb transcript from calmodulin gene I. This transcript was not detected in normal breast tissue. Because inhibiting the expression of calmodulin has been shown to reduce cellular proliferation, these data suggest that it may be possible to inhibit the rate of proliferation of the adenocarcinoma MCF7 and SkBr3 cells but not that of normal tissue, by transfecting them with an antisense vector to the 1.7 kb transcript from calmodulin gene I.

These transcripts may be targeted with either antisense oligodeoxynucleotides or polyribonucleotides (RNA) produced by an expression vector. Both antisense approaches have potential advantages and disadvantages. Experiments using antisense oligodeoxynucleotides are relatively easy to design and perform. The oligodeoxynucleotides penetrate into cells fairly easily[181] and have already been shown to have selective actions in inhibiting the rate of proliferation of PC12 cells, see Examples I and II above. However, they have a relatively short duration of action, even when modified with phosphorothioate substitutions. Furthermore, phosphorothioates have been reported to have some nonselective actions[149]. Experiments using antisense RNA expression vectors are more complicated and time-consuming to perform, but have the potential for providing a longer duration of action, inducibility, and greater selectivity towards a particular tissue and target mRNA. Therefore, they should have greater clinical applicability. Accordingly, the experimental strategy of the present invention is to use the antisense oligodeoxynucleotides for the selective inhibition of the dominant form of calmodulin mRNA found in breast tumor cells and thereby inhibit their rate of proliferation. Targeting of the antisense calmodulin constructs of the invention will be further enhanced by encapsulating them in antibody-coated liposomes.

Initially, dose-response and time-course studies will be performed. A given breast cancer cell line will be targeted with calmodulin antisense oligodeoxynucleotides specific for calmodulin genes I, II and III, administered together or separately. As negative controls, random oligodeoxynucleotides will be used. It is anticipated that the greatest inhibitory effects on the proliferation and/or differentiation of a given breast cancer cell line will be achieved using an individual calmodulin antisense oligodeoxynucleotide specific for the dominant calmodulin transcript present in that cell. An important issue which will be addressed will be the frequency of addition and the period of time required to obtain inhibition of cell proliferation.

The methods using antisense RNA expression vectors will be similar to those for the oligodeoxynucleotides in regards to the breast cancer cell lines used and the choice of specific calmodulin antisense vector. Initially, a vector containing a sequence that will inhibit the transcripts from all calmodulin genes will be transfected into a given breast cancer cell line. Additionally, vectors containing antisense sequences to the individual calmodulin transcripts will be administered. Again, it is anticipated that the greatest inhibitory effect will be observed with vectors expressing the calmodulin antisense RNA specific for the dominant calmodulin mRNA present in the particular cell line.

The oligodeoxynucleotides and RNA expression vectors will be assessed for their effects on cell proliferation as measured by direct cell counting and measurement of DNA synthesis. Any effects on differentiation, such as the production of human milk fat globule antigen will also be determined. Any changes in the levels of the calmodulin transcripts will be detected by Northern blot, and changes in the levels of calmodulin protein will be evaluated using immunocytochemistry and/or Western blot. It should be noted that although there might be a biological effect of the antisense compounds, changes in the levels of the mRNAs might not be detected, particularly in the case of antisense oligodeoxynucleotides, because the action of the antisense compounds may be largely at the level of translation[176].

Since our ultimate goal is to use the calmodulin antisense vectors to selectively target and specifically inhibit the growth of breast tumors in patients, in vivo studies will be performed to determine the anti-tumor effects of the calmodulin antisense RNA expression vector in SKBr3 tumor cells xenotransplanted into nude mice. The in vivo approach will incorporate the information regarding the selective targeting and expression of the dominant calmodulin mRNA found in breast tumor cells that was obtained from preliminary studies. The SKBr3 cells have been chosen for the following reasons. They overexpress c-erbB2 and, therefore, will be suitable to examiner in vivo the selective expression of calmodulin antisense RNA from vectors bearing a c-erbB2 promoter. They also expresses the monoclonal antibody 15-6A-reactive antigen and will, therefore, be suitable to test in vivo the selective delivery of the calmodulin antisense vector in the form of a monoclonal antibody-liposome-DNA complex. Only the calmodulin transcript that is most abundantly expressed in SKBr3 cells will be targeted using the antisense vector. The particular transcript to target will be determined by Northern blot analysis. The monoclonal antibody 15-6A- liposome-calmodulin antisense vector complexes will be administered by direct intratumoral injection. Direct in vivo injection of liposome-DNA complexes into tumor nodules in situ has already been successfully performed[137,159]. As a control, mice injected with an expression vector bearing a c-erbB2 promoter, but lacking the calmodulin antisense gene (empty vector) will also be examined.

In pilot experiments the efficiency by which the expression vectors deliver the constructs and the duration of their expression in tumors will be determined using a β-galactosidase (LacZ) reporter vector. Antibody-liposome-reporter vector complexes will be injected into tumors arising from breast tumor cells transplanted into nude mice. At different time points (e.g., 24, 48, 72, 96 hours) after intratumor injection of the complexes, the mice will be killed, and the expression of the LacZ gene will be assayed in the tumors using a histochemical β-galactosidase assay. These initial experiments will provide information concerning the percent of tumor cells which take up and express the vector.

Following these studies, the individual calmodulin antisense vector, carrying the c-erbB2 promoter will be administered intratumorally in the form of an antibody-liposome-vector complex. The dose of antibody-coated liposomes, the dose of the vector and the frequency of administering of the antisense vector will be varied, and the anti-tumor effects (tumor regression) will be determined by recording the tumor volumes and tumor weight at various points after administering the antisense. The presence of the vector and the extent to which the vector spreads will be determined in samples of DNA isolated from tumor and normal organ tissues using PCR with primers specific for the vector.

Two of the major constraints of plasmid vector-mediated gene transfer are the transient nature of the expression and the inability of the injected DNA to penetrate into all tumor cells[142,156]. Therefore, initial studies will be performed to determine whether single or, most likely, multiple injections are necessary to induce anti-tumor effects. They will also provide information concerning the possible in vivo toxicity of the antibody-liposome-vector complexes. The toxicity in mice will be assessed by comparing the body weights, temperature, and behaviors of mice injected with the vector complex with that of control animals.

Evaluation of anti-tumor effects in vivo.

a) Assessment of tumor growth. The mice will be weighed and the inoculation site palpated at weekly intervals. When the tumors become palpable (after about 3–4 weeks), their maximum and perpendicular diameters will be measured with a vernier caliper and the surface area will be calculated[110]. The experiments will be terminated 12 weeks after the tumor cell injections. At necropsy, the body and tumor weights will be recorded and the occurrence of metastases will be ascertained by macroscopic observation (followed by histological analysis of hematoxylin and eosin stained sections). The primary tumors will be excised and prepared for β-galactosidase histochemistry (animal injected with a reporter vector) or fixed in 10% neutral-buffered formalin, embedded in paraffin, and prepared for routine histological staining (hematoxylin and eosin).

b) In situ β-galactosidase histochemistry. The histochemical assay used for cells in cultures, with minor modifications, will be used to determine the efficiency by which the reporter plasmid is taken up in vivo. The tumors will be excised, fixed immediately with 4% paraformaldehyde in PBS, pH 7.1, containing 2 MM $MgCl_2$, and stored overnight at 4° C. Subsequently the tumor tissue will be cryoprotected by incubation overnight in 30% sucrose in PBS, pH 7.1, containing 2 mM $MgCl_2$. The tissues will then be frozen at 80° C., and crytostat sections (15–30 $\mu$M) will be made and mounted onto gelatinized slides. The histochemical staining for β-galactosidase will then be performed as described for the cultured cells. The controls for endogenous β-galactosidase activity will consist of tumor tissue injected with the antibody-coated liposomes lacking the vector.

Single statistical comparisons of an experimental group with its control will be performed using a paired or unpaired independent Student's t-tests as appropriate. Multiple comparison procedures among the means of three or more treatment groups will be performed using one or two-way analysis of variance (ANOVA) as appropriate, followed post-hoc by the Student-Newman-Keuls procedure. In experiments in which correlative analyses are performed, regression analyses will be conducted using data analysis software.

In summary, the major role calmodulin plays in cell proliferation and differentiation and the elevated levels of calmodulin in mammary tumors suggest that calmodulin may be a suitable target for anti-tumor therapy of breast cancer. The methodology described herein should provide a higher degree of selective targeting and expression of the calmodulin based antiproliferative agents in tumors of the breast than is currently achievable with conventional pharmacotherapy.

REFERENCES

1. Andrews G. K. (1990) Regulation of metallothionein gene expression. *Progr.Food Nutr.Sci.* 14, 193–258.

2. Anraku Y., Ohya Y. and Iida Y. (1991) Cell cycle control by calcium and calmodulin in *Saccharomyces cerevisiae*. *Biochim.Biophys.Acta* 1093, 169–177.

3. Bai G., Nichols R. and Weiss B. (1992) Cyclic AMP selectively up-regulates calmodulin genes I and II in PC12 cells. *Biochim.Biophys.Acta* 1130, 189–196.

4. Bai G. and Weiss B. (1991) The increase of calmodulin in PC12 cells induced by NGF is caused by differential expression of multiple mRNAs for calmodulin. *J.Cell.Physiol.* 149, 414–421.

5. Barbacid M. (1995) Neurotrophic factors and their receptors. *Curr. Opin. Cell Biology* 7, 148–155.

6. Chafouleas J., Bolton W. E., Hidaka H., Boyd A. E. and Means A. R. (1982) Calmodulin and the cell cycle: involvement in regulation of cell cycle progression. *Cell* 28, 41–50.

7. Chafouleas J. G., Lagace L., Bolton W. E., Boyd III A. E. and Means A. R. (1984) Changes in calmodulin and its mRNA accompany reentry of quiescent (Go) cells into the cell cycle. *Cell* 36, 73–81.

8. Cheung W. Y. (1982) Calmodulin: an overview. *Fedn.Proc.* 41, 2253–2257.

9. Chomczynski P. and Sacchi N. (1987) Single-step method of RNA isolation by the acid guanidinium thiocyanate-phenol-chlorophorm extraction. *Anal.Biochem.* 162, 156–159.

10. Christenson M. and Means A. (1993) Coordinate regulation of mRNAs from multiple calmodulin genes during myoblast differentiation in vitro. *J.Cell.Physiol.* 154, 343–349.

11. Cimino M., Chen J. and Weiss B. (1990) Ontogenetic development of calmodulin mRNA in rat brain using in situ hybridization histochemistry. *Dev.Brain.Res.* 54, 43–49.

12. Colomer J., Agell N., Engel P. and Bachs O. (1994) Expression of calmodulin and calmodulin binding proteins in lymphoblastoid cells. *J.Cell.Physiol.* 159, 542–550.

13. Davis T., Urdea M., Masiarz F. and Thorner J. (1986) Isolation of the yeast calmodulin gene: calmodulin is an essential protein. *Cell* 47, 423–431.

14. Dinsmore J. and Sloboda R. (1988) Calcium and calmodulin-dependent phosphorylation of a 62 kd protein induces microtubule depolymerization in sea urchin mitotic apparatuses. *Cell* 53, 769–780.

15. Eilam Y. and Chernichovsky D. (1988) Low concentrations of trifluoperazine arrest the cell division cycle of *Saccharomyces cerevisiae* at two specific stages. *J.Gen.Microbiol.* 134, 1063–1069.

16a. Enrietto, P. and Beug, H. (1994) Oncogenes and differentiation. *Semin. Cancer Biology.* 5, 91–94.

16. Feingold E., Seshadri S. B. and Tretiak O. (1987) Hardware and software design consideration in engineering an image processing workstation: autoradiographic analysis with DUMAS and the brain autoradiography analysis software package. In *Functional Mapping in Biology and Medicine. Experimental Biology and Medicine* (ed. McEachron I.), pp.175–203. Karger, Basel.

17. Filmore H. L., Mainardi C. L. and Hasty K. A. (1992) Differentiation of PC12 cells with nerve growth factor is associated with transin synthesis and release. *J.Neuroscience Res.* 31, 662–669.

18. Gannon M. and McEwen B. (1994) Distribution and regulation of calmodulin mRNAs in rat brain. *Mol.Brain Res.* 22, 186–192.

19. Gnegy M. E. (1993) Calmodulin in neurotransmitter and hormone action. *Annu.Rev.Pharmacol.Toxicol.* 32, 45–70.

20. Greene L., Burstein D. and Black M. M. (1982) The role of transcription-dependent priming in nerve growth factor promoted neurite outgrowth. *Dev.Biol.* 91, 305–316.

21. Greene L. A. and Tischler A. S. (1976) Establishment of a noradrenergic clonal line of rat adrenal pheochromocytoma cells which respond to nerve growth factor. *Proc.Natl.Acad.Sci.USA* 73, 2424–2428.

22. Guroff G. (1985) PC12 cells as a model of neuronal differentiation. *In Cell Culture In the Neuroscience* (eds. Bottenstein J. and Sato G.), pp.245–272. Plenum Press, New York.

23. Hager L. J. and Palmiter R. D. (1981) Transcriptional regulation of mouse liver metallothionein-1 gene by glucocorticoids. *Nature* 291, 340–342.

24. Hait W. N. (1987) Targeting calmodulin for the development of novel cancer chemotherapeutic agents. *Anti-Cancer Drug Des.* 2, 139–149.

25. Holt J. T., Gopal V., Moulton A. D. and Nienhuis A. W. (1986) Inducible production of c-fos antisense RNA inhibits 3T3 cell proliferation. *Proc.Natl.Acad.Sci.USA* 83, 4794–4798.

26. Job D., Fischer E. and Margolis R. (1981) Rapid dissasembly of cold-stable microtubules by calmodulin. *Proc.Natl.Acad.Sci.USA* 78, 4679–4682.

27. Karin M., Imbra R. J., Heguy A. and Wong G. (1985) Interleukin-1 regulates human metallothionein gene expression. *Mol.Cell.Biol.* 5, 2866–2869.

28. Keegan K. and Halegoua S. (1993) Signal transduction pathways in neuronal differentiation. *Curr.Opin.Neurobiol.* 3, 14–19.

29. Keith C., DiPaola M., Maxfield F. and Shelanski M. (1983) Microinjection of Ca2+-calmodulin causes a localized depolymerization of microtubules. *J.Biol.Chem.* 97, 1918–1924.

30. Kitajima S., Sano M., Kato K., Seto-Oshima A. and Mizutani A. (1986) Changes of calmodulin and S-100 protein in C6 glioma cells as a result of cellular differentiation induced by forskolin. *Acta Histochem.Cytochem.* 19, 365–369.

31. Klee C. B. and Vanaman T. C. (1982) Calmodulin. *Adv.Prot.Chem.* 35, 213–231.

32. Klug M., Blum J., Ye Q. and Berchtold M. (1994) Intracellular Ca2+ and Ca2+- binding proteins in chemically transformed rat fibroblasts. *Exptl.Cell Res.* 213, 313–318.

33. Leibbrandt M., Khokla R. and Koropatnick J. (1994) Antisense down-regulation of metallothionein in a human monocytic cell line alters adherence, invasion, and the respiratory burst. *Cell Growth Differ.* 5, 17–25.

34. Liu T., Williams J. and Clarke M. (1992) Inducible expression of calmodulin antisense RNA in Dictyostelium cells inhibits the completion of cytokinesis. *Mol.Biol.of the Cell* 3, 1403–1413.

35. Lu K. P., Osmani S., Osmani A. and Means A. R. (1993) Essential roles for calcium and calmodulin in G2/M progression in *Aspergillus nidulans. J.Cell Biol.* 121, 621–630.

36. MacGregor G., Nolan G., Fiering S., Roederer M. and Herzenberg L. (1991) Use of *E. coli* lacZ as a reporter gene. *Meth.Mol.Biol.* 7, 217–235.

37. Mann D. A., Doherty P. and Walsh F. S. (1989) Increased intracellular cyclic AMP differentially modulates nerve growth factor induction of three neuronal recognition molecules involved in neurite outgrowth. *J.Neurochem.* 53, 1581–1588.

38. Marcum M., Dedman J., Brinkley B. R. and Means A. (1978) Control of microtubule assembly-disassembly by calcium-dependent regulator protein. *Proc.Natl.Acad-.Sci.USA* 75, 3771–3775.

39. Mariggio M. A., Fulle S., Calissano P., Nicoletti I. and Fano G. (1994) The brain protein S-100ab induces apoptosis in PC12 cells. *Neuroscience* 60, 29–35.

40. Mather J. (1990) Optimizing cell and culture environment for production of recombinant proteins. *Meth.Enzymol.* 185, 567–587.

41. Means A. R. (1988) Molecular mechanisms of action of calmodulin. *Rec.Prog.Hor.Res.* 44, 223–261.

42. Means A. R. and Rasmussen C. D. (1988) Calcium, calmodulin and cell proliferation. *Cell Calcium* 9, 313–319.

43. Means A. R., Van Berkum M. F. A., Bagchi I., Lu K. B. and Rasmussen C. D. (1991) Regulatory functions of calmodulin. *Pharmac.Ther.* 50, 255–270.

44. Muller S., Sullivan P., Clegg D. and Feinstein S. (1990) Efficient transfection and expression of heterologous genes in PC12 cells. *DNA and Cell Biology* 9, 221–229.

45. Natsukari N., Zhang S.-P., Nichols R. A. and Weiss B. (1995) Immunocytochemical localization of calmodulin in PC12 cells and its possible interaction with histones. *Neurochem.Int.* 26, 465–476.

46. Nicotera P., Zhivotovsky B. and Orrenius S. (1994) Nuclear calcium transport and the role of calcium in apoptosis. *Cell Calcium* 16, 279–288.

47. Nojima H. (1989) Structural organization of multiple rat calmodulin genes. *J.Mol.Biol.* 208, 269–282.

48. Nojima H., Kishi K. and Sokabe H. (1987) Multiple calmodulin mRNA species are derived from two distinct genes. *Mol.Cell.Biol.* 7, 1873–1880.

49. Nojima H. and Sokabe H. (1987) Structure of a gene for rat calmodulin. *J.Mol.Biol.* 193, 439–445.

50. Nojima H. and Sokabe H. (1989) Structural organization of calmodulin genes in the rat genome. In *Calcium Protein Signaling* (eds. Hidaka H., Carafoli E., Means A. R. and Tanaka T.), pp.223–232. Plenum Publ. Corp., New York.

51. Ohya Y. and Anraku Y. (1989) A galactose depndent cmd1 mutant of *Saccaromyces cerevisiae:* involvement of yeast calmodulin in nuclear division. *Curr.Genet.* 15, 113–120.

52. Peterson G., Hannan D. and Mercer J. (1988) The sheep metallothionein gene family. Structure, sequence and evolutionary relationship of five linked genes. *Eur.J.Biochem.* 174, 417–424.

53. Rasmussen C. and Means A. (1987) Calmodulin is involved in regulation of cell proliferation. *EMBO* 6, 3961–3968.

54. Rasmussen C. and Means A. (1989) Calmodulin is required for cell-cycle progression during G1 and mitosis. *EMBO* 8, 73–82.

55. Rasmussen C. and Means A. (1992) Increased calmodulin affects cell morphology and mRNA levels of cytoskeletal protein genes. *Cell Motil.Cytoskel.* 21, 45–57.

56. Roberts-Lewis J., Cimino M., Krause II R. G., Tyrell Jr D. F., Davis L. G., Weiss B. and Lewis M. (1990) Anatomical localization of calmodulin mRNA in the rat brain with cloned cDNA and synthetic oligonucleotide probes. *Synapse* 5, 247–254.

57. Rossino P., Gavazzi I., Timpl R., Aumailley M., Abbadini M., Giancotti F., Silengo L., Marchisio P. C. and Tarone G. (1990) Nerve growth factor induces increased expression of a laminin-binding integrin in rat pheochromocytoma PC12 cells. *Exptl.Cell Res.* 189, 100–108.

58. Sahyoun N., LeVine III H., McDonald B. and Cuatrecasas P. (1986) Specific postsynaptic density proteins bind tubulin and calmodulin-dependent protein kinase type II. *J.Biol.Chem.* 261, 12339–12344.

59. Sambrook J., Fritsch E. F. and Maniatis T. (1989). *Molecular Cloning: A Laboratory Manual.* Cold Spring Harbor Press, New York.

60. Sasaki Y. and Hidaka H. (1982) Calmodulin and cell proliferation. *Biochem.Biophys.Res.Comm.* 104, 451–456.

61. Schatzman R. C., Raynor R. L. and Kuo J. F. (1983) N-(6-Aminohexyl)-5-chloro-1-naphthalenesulfonamide(W-7), a calmodulin antagonist, also inhibits phospholipid-sensitive calcium-dependent protein kinase. *Biochim.Biophys.Acta* 755, 144–147.

62. Schroeder J. J. and Cousins R. J. (1990) Interleukin-6 regulates metallothionein gene expression and zinc metabolism in hepatocyte monolayer cultures. *Proc.Natl.Acad-.Sci.USA* 81, 3137–3141.

63. Sherbany A. A., Parent A. S. and Brosius J. (1987) Rat calmodulin cDNA. *DNA* 6, 267–272.

64. Spaete R. and Mocarski E. (1985) Regulation of cytomegalovirus gene expression: a and b promoters are trans activated by viral functions in permissive human fibroblasts. *J.Virol.* 56, 135–143.

65. Takeda T. and Yamamoto M. (1987) Analysis and in vivo disruption of the gene encoding for calmodulin in Schizosaccharomyces pombe. *Proc.Natl.Acad.Sci.USA* 84, 3580–3584.

66. Takemoto D. and Jilka K. (1983) Increased content of calmodulin in human leukemic cells. *Leukemia Res.* 7, 97–100.

67. Veigl M., Sedwick D., Niedel J. and Branch M (1986) Induction of myeloid differentiation of HL-60 cells with naphthalene sulfonamide calmodulin antagonists. *Cancer Res.* 46, 2300–2305.

68. Wandosell F., Serrano L., Hernandez M. and Avila J. (1986) Phosphorylation of tubulin by a calmodulin-dependent protein kinase. *J.Biol.Chem.* 261, 10332–10339.

69. Wei J.-W. and Hickie R. A. (1981) Increased content of calmodulin in Morris hepatoma 5123 t.c. (h). *Biochem-.Biophys.Res.Comm.* 256, 1562–1563.

70. Weinman J., Gaspera B. D., Dautigny A., Dinh D. P., Wang J., Nojima H. and Weinman S. (1991) Developmental regulation of calmodulin gene expression in rat brain and skeletal muscle. *Cell Regul.* 2, 819–826.

71. Weisenberg R. (1972) Microtubule formation in vitro in solutions containing low calcium concentrations. *Science* 177, 1104–1105.

72. Weiss B., Prozialeck W. C., Cimino M., Barnette M. S. and Wallace T. C. (1980) Calmodulin and cell functions. *Ann.NY Acad.Sci.* 356, 319–345.

73. Yagle M. and Palmiter R. (1985) Coordinate regulation of mouse metallothionein I and II genes by heavy metals and glucocorticoids. *Mol.Cell.Biol.* 5, 291–294.

74. Zhang S.-P., Natsukari N., Bai G., Nichols R. and Weiss B. (1993) Localization of the multiple calmodulin messenger RNAs in differentiated PC12 cells. *Neuroscience* 55, 571–582.

75. Zhou L.-W., Moyer J. A., Muth E. A., Clark B., Palkovits M. and Weiss B. (1985) Regional distribution of calmodulin activity in rat brain. *J.Neurochem.* 44, 1657–1662.

76. Simons et al., (1992) Antisense c-myb oligonucleotides inhibit intimal atrerial smooth muschle cell accumulation in vivo. *Nature* 359, 67–70.

77. Burch, R. M. and Mahan, L. C. (1991) Oligonucleotides antisense to the Interleukin 1 receptor mRNA block the effects of Interleukin 1 in cultured murine and human fibroblasts and in mice. *J. Clin. Invest.* 88, 1190–1196.

78. Marushige, Y., Marushige, K. and Koestner, A. (1989): Chemical control of growth and morphological characteristics of anaplastic glioma cells. *Anticanc. Res.,* 9:1729–1735.

79. Ito, J-L., Kato, T., and Tanaka, R. (1990): Cytoskeletal regulation of normal rat glioblasts differentiated by glia maturation factor. *Neurochem. Int.,* 16: 1330140.

80. Means., A. R. (19940: Calcium, calmodulin and cell cycle regulations *FEBS Lett,* 347:1–4.

81. Hait, W. N., and Lee, G. L. (1985); Characterization of the cytotoxic effects of the phenothiazine class of calmodulin antagonists. *Biochem. Pharm.,* 34: 3973–3878.

82. Suzuki, N., Kanno, T., Nagata, Y., and Kato, T. (1986); Inhibition of proliferative growth in glioma cells by calmodulin atagonists *J. Neurosurg.,* 65:74–79.

83. Hait, W. N. and Gesmonde, J. (1989): Effect of antipsychotics on bleomycin cytotoxicity. *Proc. Am. Assoc. Cancer Res.,* 30: 570.

84. Hait. W., Bryne, T., Peipmeier, J., Durviage, H. J., Choudhury, S., Davis, C., and Gates, J. (1990): The effect of calmodulin inhibitors with bleomycin on the treatment of patiens with high grade gliomas. *Cancer Res.,* 50: 6636–6640.

85. Hait, W. N., Grais, L., Benz, C., and Chadman, E. (1985): Inhibition of leukemic cell growth by inhibition of calmodulin. *Cancer Chemother. Pharmacol.,* 14:202–205.

86. Wiestler, O. and Cavenee, W. (1995): Gliomas. Foreward. *GLIA,* 15: 209–219.

87. Walker, A. E., Robbins, M., and Weinfield, F. D. (1985): Epidemiolgy of brain tumors: the national survey of intracranial neoplasms. *Neurology,* 35: 219–226.

88. Kurpad, S. M., Zhao, X.-G., Wikstrand, C. J., Batra, S., McLendon, R., and Bigner, D. (1995): Tumor antigens in astocytic gliomas. *GLIA,* 15, 224–256.

89. Daumas-Duport, C., Scheithauer, B. W., O'Fallon, J., and Kelly, P. J. (1988): Grading of astrocytomas: a simple and reproducible method. *Cancer.* 62:2152–2165.

90. Sullivan, F. J., Hershcer, L. L., Cook, J. A., Smith. J., Steinberg, S. M., Epstein, A. H., Oldfield, A. J., Goffman, T. E., Kinsella, T. J., Mitchell, J. B., and Glatstein, E. (1994): National Cancer Institute (Phase II) study of high grade glioma treated with hyperfractionated radiation and iododeoxyuridine: results in anaplastic astrocytoma. *Int. J. Rad. Onc. Biol. Phys.,* 30:583–590.

91. Morrison, R. S. (1991): Supression of basic fibroblast growth factor expression by antisense deoxyribonucleotides inhibits the growth of transformed human astocytes. *J. Biol. Chem.,* 266: 728–734.

92. Papanastassiou, V., Pizer, B. L., Coakham, H. B., Bullimore, J., Zananiri, T., and Kemshead, J. T. (1993): Treatment of recurrent and cystic malignant gliomas by a single intracavitary injection of $^{131}$I monoclonal antibody: feasibility, pharmacokinetics and dosimetry. *Br.J. Cancer,* 67: 144–151.

93. Nitta, T., and Sato, K. (1994): Specific inhibition of c-sis protein synthesis and cell proliferation with antisense oligodeoxynucleotides in human glioma cells. *Neurosurgery,* 34:309–314.

94. Westphal. M., Hamel, W., Zirkel, D., Hermann, H. D., Bilzer, T., Reinfenberger, G., Schober, R., Wechsler, W., Albert, F. K. and Behnke, J. (1994): Epidermal growth factor receptor expression in human malignant glioma: in vitro and in vivo effects of application of monoclonal antibodies to the epidermal growth factor receptor. *Rec. Res. Cancer Res.,* 135: 171–184.

95. Davico Bonino, L., De Monte, L. B., Spagnoli, G. C., Vola, R., Mairani, M., Barone, D., Moro, A. M., Riva, P., Nicotra, M. R., and Natali, P. G. (1995) Bispecific monoclonal antibody anti-CD3×anti-tenascin: an immunotherapeutic agent of human glioma. *Int.J. Cancer,* 61:509–515.

96. Trojan, J., and Ilan, J. (1995): Antisense IGF-I gene transfer and immunotherapy of glioblastoma.*Restor. Neurol. Neurosc.,* 8:77–79.

97. Kramm, K., Sena-Esteves, M., Barnett, F., Rainov, N., Schuback, D., Yu, J., Pechan, P., Paulus, W., Chiocca, E. A., and Breakfield, X. (1995): Gene therapy for brain tumors. *Brain Pathol.,* 5:345–381.

98. Takamiya, Y., Short, M. P. Ezzedine, Z. D., Moolten, F. L., Breakfield, X. O., and Martuza, R. L. (1992): Gene therapy of malignant brain tumors: a rat glioma line bearing the herpes simplex virus type 1-thymidine kinase gene and wild type retrovirus kills other tumor cells. *J. Nueroscience Res.* 33: 493–503.

99. Yamada, M., Shimizu, J., Miyao, Y., Hayakawa, T., Ikenaka, K., Nakahira, K., Nakajima, K., Kagawa, T., and Mikoshiba, K. (1992): Retrovirus-mediated gene transfer targeted to malignant glioma cells in murine brain. Japan *J. Cancer Res.,* 83:1244–1247.

100. Moolten, F. L. and Wells, J. M. (1990): Curability of tumors bearing herpes thymidine kinase genes transferred by retroviral vectors. *J.Natl. Cancer Inst.,* 82: 297–300.

101. Chen, S. H., Shine, H. D., Goodman, J. C., Grossman, R. G., and Woo, S. L. (1994): Gene therapy for brain tumors: regression of experimental gliomas by adenovirus-mediated gene transfer in vivo. *Proc. Natl. Acad. Sci. USA,* 91:3054–3057.

102. Perez-Curet, M. J., Trask, T. W., Chen, S. H., Goodman, J. C., Woo, S. L. C., Grossman, R. G., and Shine, H. D. (1994): Adenovirus-mediated gene therapy of experimental gliomas. *J. Neuroscience Res.,* 39:506–511.

103. Ridet, J. L., and Privat, A. (1995): Gene therapy in the central nervous system: direct versus indirect gene delivery. *J. Neuroscience Res.,* 42:287–293.

104. Moolton, F. L. (1986): Tumor chemosensitivity conferred by inserted herpes thymidine kinase genes: Paradigm for a prospective cancer control strategy. *Cancer Res.,* 46:5276–5281.

105. Culver, K. W., Ram, Z., Walbridge, S. Ishii, H., Oldfield, E. H., and Blaese, R. M. (1992); In vivo gene transfer with retroviral vecotr-producer cells for treatment of experimental brain tumors. *Science,* 256: 1550–1552.

106. Barba, D., Hardin, J., Ray, J., and Gage, F (1993): Thymidine kinase-mediated killing of rat brain tumors. *J. Neurosurg.,* 79:729–735.

107. Whitesell, L., Rosolen, S., and Neckers, L. M. (1991): Episome-generated N-myc antisense RNA restricts the differentiation potential of primitive neuroectodermal cell lines. *Mol. Cell. Biol.,* 11:1360–1371.

108. Neckers, L. M. Rosolen, A., and Whitesell, L. (1992): Antisense inhibition of gene expression: a tool for studying the role of NMYC in the growth and differentiation of neuroectoderm derived cells. *J. Immunother.,* 12:162–166.

109. Trojan, J., Blossey, B. K., Johnson, T.r., Rudin, S. D., Tyjkocinski, M., Ilan, J. U., and Ilan, J. (1992): Loss of tumorigenicity of rat glioblastoma directed by episome-based antisense cDNA transcription of insulin-like growth factor I. *Proc. Natl. Acad. Sci. USA,* 89:4874–4878.

110. Trojan, J., Johnson, R. T., Rudin, S. D. Ilan, J. U., Tykocinski, M., and Ilan, J. (1993): Treatment and prevention of rat glioblastoma directed by immunogenic antisense IGRF-1 tumor transfectants. *Science,* 259:94–97.

111. Resnikoff, M., Sell, C., Rubini, M., Coppola, D., Ambrose, D., Baserga, R., and Rubin, R. (1994): Rat glioblastoma cells expressing an antisense RNA to the insulin-like growth factor-1 (IGF-1) receptor are nontumorigenic and induce regression of wild-type tumors. *Cancer Res.,* 54:2218–2222.

112. Neckers, L, and Whitesell, L. (1993): Antisense technology: biological utility and practical considerations. *Amer. J. Physiol.* 265:L1–L12

113. Russel, S. J., Hawkins, R. E., and Winter, G. (1993): Retroviral vectors displaying functional antiboby fragments. *Nucl. Acids. Res.,* 21:1081–1085.

114. Yagi, K., Hayaski, Y., Ishida, N., Ohbayaski, M., Ohishi, N., Mizuno, M., and Yoshida, J. (1994): Interferon-beta endogenously produced by intratumoral injection of cationic liposome-encapsulated gene: cytocidal effect on glioma transplanted into nude mouse brain. *Biochem. Molec. Biol. Internat.,* 32:167–171.

115. Zhang, S. P., Nichols, R. A., and Weiss, B. (1994): Oligodeoxynucleotide antisense to calmodulin mRNAs inhibit proliferation and NGF-induced differentiation of PC12 cells. *Soc. Neurosc.,* 20:2316.

116. Davidkova, G., Zhang, S. P., Nichols, R. A., and Weiss, B. (1996): Reduced level of calmodulin in PC12 cells induced by stable expression of calmodulin antisense RNA inhibits cell growth and induces neurite outgrowth. *Neuroscience, in press.*

117. Rodeck, U., Herlyn, M., Herlyn, D., Molthoff, C., Atikison, B., Varello, M., Stephlewski, Z., and Koprowski, H. (1987): Tumor growth modulation by a monoclonal antibody to the epidermal growth factor receptor: immunologically mediated and effector cell-independent effects. *Cancer Res.,* 47: 3692–3696.

118. Murthy, U., Reiman, D. J., and Rodeck, U. (1990): Inhibition of TGF α-induced second messengers by anti-EGF receptor antibody-425. *Biochem. Biophys. Res. Comm.,* 172:471–476.

119. Arita, N., Hayakawa, T., Izumoto, S., Taki, T., Ohnishi, T., Yamamoto, H., Bitoh, S., and Mogami, H. (1989): Epidermal growth factor receptor in himan glioma. *J. Neurosurg.,* 70:916–919.

120. Ekstrand, A. J., James, C. D., Cavenee, W. K., Seigler, B., Petterson, R. F., and Collins, V. P. (1991); Genes for epidermal growth factor receptor, transforming growth factor alpha and epidermal growth factor and their expression in human gliomas in vivo. *Cancer Res.,* 51: 2164–2172.

121. Hoi Sang, U., Espiritu, O. D., Kelley, P. Y., Klauber, M. R., and Hatton, J. D., 1995): The role of the epidermal growth factor receptor in human gliomas: I. The control of cell growth. *J. Neurosurg.,* 82:841–846.

122. Takahaski, H., Herlyn, D., Atkison, B., Powe, J., Rodeck, U., U., Alavi, A., Bruce, D.A., and Koprowski, H. (1987): Radioimmunodetection of humal glioma xenografts by monoclonal: antibody to epidermal growth factor receptor. *Cancer Res.,* 47: 3847–3850.

118. Theirry, A., Rahman, A., and Dritschilo, A. 1992): Liposomal Delivery as a New Approach to Transport Antisense Oligonucleotides In *:Gene Regulation: Biology of Antisense RNA and DNA,* edited by R. P. Erickson, et al, pp. 147–160. Raven Press, Ltd., New York.

124. Solomon, S., Palazzo, M. R., Smoake, J. A., and Raghow, R. S. (1995); Insulin-stimulated calmodulin gene expression in rat H-411E cells can be selectively blocked by antisense oligonucleotides. *Biochem. Biophys. Res. Comm.,* 210:921–930.

125. Holmberg, E. G. Reuer, Q. R., Giesert E. E., and Ownens, J. L. (1994) Delivery of plasmid DNA to glial cells using pH sensitive immunoliposomes. *Biochem. Biophys. Res. Comm.* 210:888–893.

126. Lesserman, L. D., Barbet, J., and Dourilsky, F., (1980) Targeting to cells of flourescent liposomes covalently coupled with monoclonal antibody or protein A. *Nature* 288:602–604.

127. New, R. C., (1994) Liposomes: A practical approach. IRL Press, Oxford.

128. Maruyama, K., Kennel, D., and Huang, L. (1990) Lipid composition is important for highly efficieint target binding and retention of immunoliposomes. *Proc. Natl. Acad. Sci. USA* 87:5744–5748.

129. Weiss, B., Davidkova, G., and Zhang, S. P., (1996): Antisense strategies in neurobiology. *Neurochem. Internat.,* in press.

130. Besnard, F., Brenner, M., Nakatani, Y., Chao, R., Purohit, R., and Freese, E. (1991): Multiple interacting sites regulate astrocyte-specific transcription of the human gene for glial fibrillary acidic protein. *J. Biol. Chem.,* 266: 18877–18883.

131. Myers, R. L., Chedid, M., Tronick, S. R., and Chie, I. M. (1995) Different fibrobalsgt growth factor 1 (FGF1) transcripts in nerual tissues, glioblastomas and kidney carcinoma cell lines *Oncog.* 11:785–789.

132. Abe, M. and Kufe, D. W.1984.Sodium butyrate induction of milk related antigens in human MCF-7 breast carcinoma cells. *Cancer Res.* 44:4574–4577.

133. Alama, A., Meazza, R., Barbieri, F., Biassoni, R., Mazzei, M. and Nicolin, A. 1993.Antiproliferative effect of DNA polymerase a antisense oligodeoxynucleotides on breast cancer cells. *Exptl.Cell Res.* 206:318–322.

134. Anfossi. G., Gewire, A. M. and Calabretta, B. 1989.An oligomer complementary to c-myb-encoded mRNA inhibits proliferation of human myeloid leukemia. *Proc.Natl.Acad.Sci. USA* 86:3379–3383.

135. Ausubel. F. M., Brent, R., Kingston, R. E., Moore, D., Seidman, J., Smith, J. and Struhl, K. Short Protocols in Molecular Biology, New York:John Witey & Sons, 1994. Ed. 2ed 136. Bai, G., Nichols, R. and Weiss, B. 1992.Cyclic AMP selectivity up-regulates carmodulin genes I and II in PC12 cells. *Biochim.Biophys.Acta* 1130: 189–196.

137. Calvez, V., Rixie, O., Wang, P., Mouawad, R., Soubrane, C., Ghoumari, A.,Verola, O., Khayat, D. and Colbere-Garapin, F. 1996. Virus-free transfer of the herpes simplex virus thymidine kinase gene followed by ganciclovir treatment induces tumor cell death. *Clin. CancerRes.* 2:47–51.

138. Cerutti, J., Trapasso, F., Battaglia, C., Zhang, L., Martelli, M. L. and Visconti, R. 1996.Block of c-myc expression by antisense oligodeoxynucleotides inhibits proliferation of human thyroid carcinoma cell lines. *Clin.CancerRes.* 2:119–126.

139. Chakrabarty, S., Rajagopal, S. and Huang, S. 1995.Expression of antisense epidermal growth factor receptor RNA downmodulates the malignant behavior of human colon cancer cells. *Clin.Exp.Metastis*13:191–195.

140. Chang, A. Y. and Garrow, G. C. 1995.Pilot study of vinorelbine (Navelbine) and paclitaxel (Taxol) in patients with refractory breast cancer and lung cancer. *Semin.Oncol.* 22:66–70.

141. Chen, J. and Weiss, B. 1991.Ontogenetic expression of D2 dopamine receptor mRNA in rat corpus striatum. *Dev. Brain.Res.* 63:95–104.

142. Crystal, R. G. 1995.Transfer of genes to humans: early. lessons and obstacles to success. *Science* 270:404–410.

143. Doll, R. Cancer Incidence in Five Continents. Vol. V, Lyon:WHO *International Agency for Research on Cancer*, 1987.

144. Doll, R., Muir, C. and Waterhouse, J. Cancer Incidence in Five Continents, Vol. II, New York: Springer-Verlag, 1970.

145. Elstner, E., linker-Israeli, M., Said, J., Umiel, T., devos, S., Shintaku, I. P. and Heber, D. 1995.20-epi-vitamin D3 analogues: a novel class of potent inhibitors of proliferation and inducers of differentiation of human breast cancer cell lines *Cancer Res.* 55:2822–2830.

146. Etienne-Julan, M., Roux, P., Carillo, S., Jeanteur, P. and Piechaczyk, M. 1992.The efficiency of cell targeting by recombinant retroviruses depends on the nature of the receptor and the composition of the artificial cell-virus linker. . *Gen. Virol.* 73:3251–3255.

147. Gewirtz, A. M.1993.Therapeutic application of antisense DNA in the treatment of human leukemia. *ProcAm.Assoc.Cancer Res.* 34:595–597.

148. Guilbaud, N., Gas, N., Dupont, M. A. and Valette, A. 1990.Effects of differentiation-inducing agents on maturation of human MCF-7 breast cancer cells.*J.Cell-Physiol.*145:162–172.

149. Gura, T. 1995.Antisense has growing pains. *Science* 270:575–577.

150. Hait, W. N.,Gesmonde, J. and Lazo, J. 1994.Effect of anti calmodulin drugs on the growth and sensitivity of C6 rat glioma cells to bleomycin. *Anticanc.Res.* 14:1711–1722.

151. Hardcastle, I. R.,Rowlands, M. G.,Houghton, J.,Parr, I.,Potter, G. A. and Jarman, M. 1995.Rationally designed analogues of tamoxifen with improved calmodulin antagonism. *J.Med.Chem.* 38:241–248.

152. Harris, A. L.,Fox, S., Bicknell, R., Leek, R., Relf, M., LeJeune, S. and Kakamanis, L. 1994.Gene therapy through signal transduction pathways and angiogenic growth factors as therapeutic targets in breast cancer. *Cancer* 74:1021–1025.

153. Hickie, R. A., Graham M. J., Buekmeier, J. A. and Meyskens, F.L.Jr.1992.Comparison of calmodulin gene expression in human neonatal melanocytes and metastic melanoma cell lines. *J.Invest.Dermatol.*99:764 773.

154. Hollywood, D. P. and Hurst, H. C. 1993.A novel transcription factor, OB2-1, is required for overexpression of the proto-oncogene c-erbB2 in mammary tumor cell lines. *EMBO* 12:2360–2375.

155. Lazo, J. S., CHen, E. L., Gallichio, V. S, and Hait, W. N. (1986) Increased lethality of calmodulin antagonists and bleomycin to human bone marrow and bleomycin resistant malignant cells. *Cancer Res.* 46:2236–2240.

156. Ledley, F. (1995) Nonviral gene therapy: the promise of genes as pharmaceutical products. *Human Gene Therapy* 6:1129–1144.

157. Li, T and Hightower, L., (1995) Effects of dexamethasone, heat shock and serum responses on the inhibition of Hsc70 synthesis by antisense RNA in NIH 3T3 cells. *J. Cell. Physiol.* 164:344–355.

158. Lippman, M. E. (1993) The development of biological therapies for breast cancer. *Science* 259:631–632.

159. Lu, D., Benjamin, R., Kim, M., Conry, R. M, and Curiel, D. T. (1994) Optimization of methods to achieve mRNA-mediated transfection of tumor cells in vitro and in vivo employing cationic liposome vectors. *Cancer Gene Ther.* 1:245–252.

160. MacNeil, S., Wagner, M., and Rennie, I. G. (1994) Tamoxifen inhibition of ocular cell melanoma attachment to matrix protiens. *Pigment Cell Res.* 7:222–226.

161. Maeda, O., Terasawa, M., Ishikawa, T., Oguchi, M., Mizuno, K., Kawai, M., and Kikkawa, F. (1993) A newly synthesized bifunctional inhibitor, W-77, enhances adriamycin activity againsgt human ovarian carcinoma cells. *Cancer Res.* 53:2051–2056.

162. Mahendroo, M. S., Mendelson, C. R. and Simpson, E. R. 1993.Tissue-specific and hormonally-controlled alternative promoters regulate aromatase cytochrome P450 gene expression in human adipose tissue. *J.Biol. Chem.* 268: 19463–19470.

163. Minami, H., Inoue, S. and Hidaka, H. 1994.The effect of KN-62, Ca2+/calmodulin dependent protein kinase II inhibitor on cell cycle. *Biochem.Biophys.Res.Comm.* 199:241–248.

164. Morelli, D., Menard, S.,Pozi, B., Balsari, A. and Colnagi, M. I.1994.Effect of a bifunctional monoclonal antibody directed against a tumor marker and doxorubicin on the growth of epidermoid vulvar carcinoma grafted in athymic mice. *Cell Biophys.* 4:119–126.

165. Murthy, U., Basu, U.-, Rodeck, U., Herlyn, M., Ross, A. H. and Das, M. 1987.Binding of an antagonistic monoclonal antibody to an intact and fragmented EGF-receptor polypeptide. *Arch Biochem.Biophys.* 252:549–560.

166. Nabel, G. J., Nabel, E. G., Yang, Z. Y., Fox, B., Plautz, G. E., Gao, X., Huang, L., Shu, S., Gordon, D. and Chang, A. E. 1993.Direct gene transfer with DNA-liposome complexes in melanoma expression, biologic activity, and lack of toxicity in humans. *Proc.Natl.Acad-.Sci.USA*90:11307–11311.

167. Neckers, L. and Whitesell, L. 1993.Antisense technology: biological utility and practical considerations. *Amer.J.PhysioL* 265:LI-L12.

168. Pierga, J.-Y. and Magdelenat, H. 1994.Applications of antisense oligonucleotides in oncology. *Cell Mol.Biol.* 40:237–261.

169. Robinson, R. G., Preston, D. R., Schiefelbein, M., and Baxter, K. G. (1995) Strontium 89 therapy for the palliation of pain due to osseous metastases. *JAMA* 274:420–424.

170. Rockwell, S. C., Kallman, R. F. and Fajardo, L. F. (1972) Characteristics of a serially transplanted mouse mammary tumor and its tissue-culture adapted derivative. *J. Natl. Cancer. Inst.* 49:739–749.

171. Rose, D. P., Connolly, J. M. and Liu, X.-H. 1994.Effects of linoleic acid on the growth and metastasis of two human breast cancer cell lines in nude mice and the invasive capacity of these cell lines in vitro. *CancerRes.* 54:6557–6562.

172. Rowlands, M. G., Parr, I. B., McCague, R., Jarman, M. and Goddard, P. (1990) Variation of the inhibition of calmodulin dependent cyclic AMP phosphodiesterase amongst analogues of tamoxifen; correlations with cytotoxicity. *Biochem. Pharm.* 40:283–289.

173. Russel, S. J., Hawkins, R. E. and Winter, G. (1993) Retroviral vectors displaying functional antibody fragments. *Nucl. Acids Res.* 21:1081–1085.

174. Sondik, Ph. D. 1994. Breast cancer trends. Incidence, mortality, and survival. *Cancer* 74:995–999.

175. Swain, S. M. and Lippman, M. E. 1989. Systemic therapy of locally advanced breast cancer: review and guidelines. *Oncol.* 3:21–28.

176. Uhlmann, E., and Peyman, A. 1990. Antisense oligonucleotides: a new therapeutic principle. *Chemical Rev.* 90:544–579.

177. Venturelli, D., Mariano, M. T., Szcylik, C., Valtieri, M., Lange, B., Crist, W. and Link, M. 1990. Down-regulated c-myb expression inhibits DNA synthesis of T-leukemia cells in most patients. *Cancer Res.* 50:7371–7375.

178. Vile, R. G., and Hart, I. R. 1993. In vitro and in vivo targeting of gene expression to melanoma cells. *Cancer Res.* 53:962–967.

179. Weber, B., Abel, K., Brody, L., Flejter, W. and Chandrasekharappa, S. 1994. Familial breast cancer. *Cancer* 74:1013–1020.

180. Wickstrom, E. L., Bacon, T., Gonzalez, A., Lyman, H. and Wickstrom, E. 1989. Anti c-myc DNA increases differentiation and decreases colony formation by HL-60 cells. In Vitro Cell Dev. Biol. 24:297–302.

181. Zhang, S. P., Zhou, L. W., Morobito, M., Lin, R. C. S. and Weiss, B. 1996. Uptake and distribution of fluorescein-labeled $D_2$ dopamine antisense oligodeoxynucleotide in mouse brain. *J. Mol. Neurosci*, submitted for publ.

182. Zugmaier, G., and Lippman, M. E. 1990. Effects of TGF beta on normal and malignant mammary epithelium. *Ann. NY Acad. Sci.* 593:272–275.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A DNA construct encoding a sequence antisense to an mRNA molecule of a predetermined calmodulin gene which is endogenously expressed in a mammalian cell, said construct consisting essentially of:
   a) a 5' promoter element;
   b) a DNA segment, said DNA segment encoding an antisense oligonucleotide between 15 and 30 nucleotides in length, said antisense oligonucleotide hybridizing to a translational start site on an mRNA molecule located within a cell which produces said calmodulin, said segment consisting essentially of a sequence selected from the group of sequences consisting of SEQ ID NOS: 1–4, said DNA segment being operably linked to said 5' promoter element such that expression of said DNA segment is controlled by said 5' promoter element; and
   c) a 3' polyadenylation signal sequence, said 3' polyadenylation sequence being selected from the group of sequences consisting of SV40 polydenylation sequences, human growth hormone polyadenylation signal sequence and thymidine kinase polyadenylation signal sequences and operably linked to said DNA segment thereby promoting stability of sequences encoded by said DNA segment.

2. A vector comprising a DNA construct according to claim 1.

3. The DNA construct as claimed in claim 1, wherein said 5' promoter element is selected from the group consisting of cytomegalovirus promoter element, metallothionein promoter element, SV40 promoter element, glial fibrillary acid protein element and heat shock promoter element.

4. The DNA construct as claimed in claim 1, further comprising at least one selectable marker gene, said at least one selectable marker gene being inserted within said construct so as not to disrupt expression of said DNA segment and encoding a protein conferring resistance to a selection agent.

5. The DNA construct as claimed in claim 4, wherein said selectable marker gene confers resistance to a selection agent selected from the group consisting of hygromycin, neomycin, ampicillin, spectinomycin or streptomycin.

6. A recombinant vector encoding an antisense molecule to a predetermined calmodulin gene, said vector comprising:
   a) at least one selectable marker gene, said at least one selectable marker gene encoding a protein conferring resistance to a selection agent, said selectable marker gene being inserted within the vector so as not to interfere with production of said antisense molecule;
   b) a 5' promoter element;
   c) a DNA segment, said DNA segment encoding an antisense oligonucleotide between 15 and 30 nucleotides in length, said antisense oligonucleotide binding a translational start site on an mRNA molecule located within a cell, said mRNA molecule encoding said predetermined calmodulin molecule; said DNA segment being operably- linked to said 5' promoter element such that expression of said DNA segment is regulated by said 5' promoter element, said antisense oligonucleotide consisting essentially of a sequence selected from the group consisting of SEQ ID NO:1, SEQ ID NO:2, SEQ ID NO:3, SEQ ID NO: 4;
   d) a 3' polyadenylation signal sequence, said 3' polyadenylation signal sequence being operably linked to said DNA segment and being selected from the group of sequences consisting of SV40 polyadenylating sequences human growth hormone polyadenylation signal sequence and thymidine kinase polyadenylation signal sequences and thereby promoting stability of sequences encoded by said DNA segment; and
   e) an E. coli origin of replication element, ColE1, said ColE1 element facilitating replication, maintenance, and high copy number in E. coli; and
   f) a PSV40/ori element, said PSV40/ori element facilitating episomal replication in mammalian cells expressing SV40 large T antigen.

7. An olicionucleotide between 15 and 30 nucleotides in length consisting essentially of a sequence selected from the group of sequences encoded by SEQ ID No:1 and SEQ ID NO:2, said sequences having binding affinity for a translational start site of a nucleic acid sequence encoding a mammalian type I calmodulin gene, specific binding of said oligonucleotide to said start site inhibiting expression of said calmodulin gene.

8. The oligonucleotide of claim 7, which is an oligonucleotide analog.

9. The oligonucleotide of claim 7, which is phosphorothioate modified.

10. A composition comprising the oligonucleotide of claim 7 suspended in a biologically compatible medium.

11. A composition as claimed in claim 7 which further comprises at least one agent for improving membrane permeability.

12. An oligonucleotide between 15 and 30 nucleotides in length consisting essentially of a sequence selected from the group of sequences encoded by SEQ ID NO:3 and SEQ ID NO:4, said sequences having binding affinity for a translational start site of a nucleic acid sequence encoding a mammalian type II calmodulin gene, specific binding of said oligonucleotide to said start site inhibiting expression of said calmodulin gene.

13. The oligonucleotide of claim 12, which is an oligonucleotide analog.

14. The oligonucleotide of claim 12, which is phosphorothioate modified.

15. A composition comprising the oligonucleotide of claim 12 suspended in a biologically compatible medium.

16. A composition as claimed in claim 12 which further comprises at least one agent for improving membrane permeability.

17. A method for inhibiting expression of a mammalian type I calmodulin gene in a mammalian cell in vitro, said method comprising:
   a) providing an oligonucleotide consisting essentially of a sequence selected from the group of sequences encoding SEQ ID NO: 1 and SEQ ID NO: 2; and
   b) administering said oligonucleotide to said cells under conditions whereby said antisense oligonucleotide enters cells expressing said type I calmodulin gene and binds specifically to said translational start site of said calmodulin gene in an amount sufficient to inhibit expression of said calmodulin type I gene.

18. A method as claimed in claim 17, wherein said mammalian cell is a neuronal cell and inhibition of expression of said calmodulin gene induces a differentiation phenotype.

19. A method for inhibiting expression of a mammalian type II calmodulin gene in a mammalian cell in vitro, said method comprising:
   a) providing an oligonucleotide consisting essentially of a sequence selected from the group of sequences containing SEQ ID NO: 3 and SEQ ID NO: 4; and
   b) administering said oligonucleotide to said cells under conditions whereby said antisense oligonucleotide enters calls expressing said type II calmodulin gene and binds specifically to said translational start site of said calmodulin gene in an amount sufficient to inhibit expression of said calmodulin type II gene.

* * * * *